(12) United States Patent
Crooke et al.

(10) Patent No.: US 9,540,641 B2
(45) Date of Patent: Jan. 10, 2017

(54) CANCER TREATMENT

(71) Applicant: IONIS PHARMACEUTICALS, INC., Carlsbad, CA (US)

(72) Inventors: Stanley T. Crooke, Carlsbad, CA (US); Mason Yamashita, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/439,363

(22) PCT Filed: Oct. 30, 2013

(86) PCT No.: PCT/US2013/067469
§ 371 (c)(1),
(2) Date: Apr. 29, 2015

(87) PCT Pub. No.: WO2014/070868
PCT Pub. Date: May 8, 2014

(65) Prior Publication Data
US 2016/0002625 A1  Jan. 7, 2016

Related U.S. Application Data

(60) Provisional application No. 61/720,939, filed on Oct. 31, 2012, provisional application No. 61/777,875, filed on Mar. 12, 2013.

(51) Int. Cl.
*A61K 48/00* (2006.01)
*C12N 15/113* (2010.01)
*C07K 14/47* (2006.01)

(52) U.S. Cl.
CPC ......... *C12N 15/113* (2013.01); *C07K 14/4718* (2013.01); *C12N 2310/11* (2013.01); *C12N 2310/111* (2013.01); *C12N 2310/315* (2013.01); *C12N 2310/3231* (2013.01); *C12N 2310/3233* (2013.01); *C12N 2310/3341* (2013.01); *C12N 2310/341* (2013.01); *C12N 2310/346* (2013.01); *C12N 2320/35* (2013.01)

(58) Field of Classification Search
CPC .................................................. A61K 48/00
See application file for complete search history.

(56) References Cited

U.S. PATENT DOCUMENTS

| | | | |
|---|---|---|---|
| 6,784,290 B1 * | 8/2004 | Monia | C07K 14/82 435/6.11 |
| 7,611,839 B2 | 11/2009 | Twine et al. | |
| 8,816,056 B2 | 8/2014 | Swayze et al. | |
| 9,359,608 B2 | 6/2016 | Swayze et al. | |
| 2007/0213288 A1 * | 9/2007 | Haura | C07K 14/4705 514/44 A |
| 2010/0298409 A1 | 11/2010 | Xie et al. | |
| 2011/0054003 A1 | 3/2011 | Karras | |
| 2012/0065125 A1 | 3/2012 | Yu et al. | |
| 2012/0202874 A1 | 8/2012 | Karras | |

FOREIGN PATENT DOCUMENTS

| | | |
|---|---|---|
| WO | 00/61602 A1 | 10/2000 |
| WO | 2005/083124 A1 | 9/2005 |
| WO | 2008/109494 A1 | 12/2008 |
| WO | 2012/135736 A2 | 4/2012 |

OTHER PUBLICATIONS

Ding et al. (Blood 2008, 111:1515-1523).*
Blakey; AZD9150, A Next Generation Antisense Oligonucleotide Targeting Stat 3, Preclinical and Early Clinical Experience, SMI Conference on RNA Therapeutics, London Jun. 5-6, 2013.
Blakey; Advances in novel technologies to tackle intractable intracellular targets, Next generation antisense oligonucleotides (ASOs), 13th Tumour Microenvironment Workshop, Miami, May 2-4, 2013.
Darnell et al; Jak-STAT Pathways and Transcriptional Activation in Response to IFNs and Other Extracellular Signaling Proteins, Science, New Series, vol. 264, No. 5164 (Jun. 3, 1994), pp. 1415-1421.
Fukada et al; Two signals are necessary for cell proliferation induced by a cytokine receptor gp130: involvement of STAT3 in Anti-Apoptosis; Immunity, vol. 5, Nov. 1996, pp. 449-460.
Gough et al; Mitochonridal Stat3 supports Ras-dependent Oncogenic Transofomration; Science. Jun. 26, 2009; 324(5935): pp. 1713-1716.
Hong et al; A Phase 1 Dose Escalation, Pharmacokinetic and Pharmacodynamic Evaluation of eLF-4E Antisense Oligonucleotide LY2275796 in patients with advanced cancer; Clin Cancer Res, 17(20), Oct. 15, 2011, pp. 6582-6591.
International Search Report dated Feb. 26, 2014 and Written Opinion dated Feb. 26, 2014 for PCT/US2013/067469 (12 pages).
Jain et al; Repression of Stat3 Activity by activation of mitogenactivated protein kinase (MAPK), Oncogene, 1998, 17, pp. 3157-3167.
Monia; Development of anti-sense drugs for cancer, 8th Annual OTS Meeting, Oct. 31, 2012.
Woessner et al; AZD9150, a new generation antisense molecule targeting STAT3, with potent pre-clinical pharmacodynamic and tumour growth inhibition activity, and early signs of clinical activity in large B-cell lymphoma, 2nd FEBS Special Meeting on JAK-STAT Signalling: Model Organisms and Beyond, Sep. 12-15, 2013 in Nottingham UK.

(Continued)

Primary Examiner — Kimberly Chong
(74) Attorney, Agent, or Firm — Scott A. Williams

(57) ABSTRACT

In certain embodiments, methods, compounds, and compositions for treating B-cell lymphoma or hepatocellular carcinoma by inhibiting expression of STAT3 mRNA or protein in an animal are provided herein. Such methods, compounds, and compositions are useful to treat, prevent, or ameliorate B-cell lymphoma or hepatocellular carcinoma. The STAT (signal transducers and activators of transcription) family of proteins are DNA-binding proteins that play a dual role in signal transduction and activation of transcription.

8 Claims, No Drawings

(56) References Cited

OTHER PUBLICATIONS

Yang et al; STAT3 complements defects in an interferon-resistant cell line: Evidence for an essential role for STAT3 in interferon signaling and biological activities; Proc Natl Acad Sci, USA, Cell Biology, vol. 95, May 1998, pp. 5568-5572.

Zhong et al; Stat3 and Stat4: Members of the family of signal transducers and activators of transcription, Procl Natl Acad Sci, USA, vol. 91, May 1994, Biochemistry, pp. 4806-4810.

Callies et al., 'Integrated Analysis of Preclinical Data to Support the Design of the First in Man Study of LY2181308, a Second Generation Antisense Oligonucleotide', British Journal of Clinical Pharmacology (2011); vol. 71; No. 3; 416-428.

Chiarle et al., 'Stat3 is Required for ALK-mediated Lymphomagenesis and Provides a Possible Therapeutic Target', Nature Medicine (2005); vol. 11; No. 6; 623-629.

Ding et al., 'Constitutively Activated STAT3 Promotes Cell Proliferation and Survival in the Activated B-cell Subtype of Diffuse Large B-cell Lymphomas', Blood Journal (2008); vol. 111; No. 3; 1515-1523.

Extended European Search Report for European Patent Application No. 13850047.5; mailed May 30, 2016 (comprises supplementary European search report and European search opinion).

Geary et al., 'Pharmacokinetics of a Tumor Necrosis Factor-α Phosphorothioate 2'-O-(2-methoxyethyl) Modified Antisense Oligonucleotide: Comparison Across Species', Drug Metabolism & Disposition (2003); vol. 31; No. 11; 1419-1428.

Hong et al., 'AZD9150, a Next-generation Antisense Oligonucleotide Inhibitor of *STAT3* with Early Evidence of Clinical Activity in Lymphoma and Lung Cancer', Science Translational Medicine (2005); vol. 7; Issue 314; 1-12.

Li et al , 'Inhibition of Growth and Metastasis of Human Hepatocellular Carcinoma by Antisense Oligonucleotide Targeting Signal Transducer and Activator of Transcription 3', Clinical Cancer Research (2006); vol. 12; No. 23; 7140-7148.

Su et al., 'Advances in Understanding the Role of STAT3 in the Pathogenesis of Hepatocellular Carcinoma', World Chinese Journal of Digestology (2010); vol. 18; No. 21; 2240-2246 (English Abstract only).

Yu et al., 'Cross-Species Pharmacokinetic Comparison from Mouse to Man of a Second-generation Antisense Oligonucleotide, ISIS 301012, Targeting Human Apolipoprotein B-100', Drug Metabolism & Disposition (2007); vol. 35; No. 3; 460-468.

Wu Zhuli et al., 'Expression of STAT3 in Diffuse Large B Cell Lymphoma and the Prognosis Significance', Essay Collection of The 11th Chinese Conference on Malignant Lymphoma, CACA (2009); pp. .

Wu Zhuli et al., 'Expression of STAT3 in Diffuse Large B Cell Lymphoma and the Prognosis Significance', Essay Collection of The 11th Chinese Conference on Malignant Lymphoma, CACA (2009); p. 442.

* cited by examiner

SEQUENCE LISTING

<160> NUMBER OF SEQ ID NOS: 129

<210> SEQ ID NO 1
<211> LENGTH: 4978
<212> TYPE: DNA
<213> ORGANISM: Homo sapiens

<400> SEQUENCE: 1

| | | | | | | |
|---|---|---|---|---|---|---|
| ggtttccgga | gctgcggcgg | cgcagactgg | gagggggagc | cggggggttcc | gacgtcgcag | 60 |
| ccgagggaac | aagccccaac | cggatcctgg | acaggcaccc | cggcttggcg | ctgtctctcc | 120 |
| ccctcggctc | ggagaggccc | ttcggcctga | gggagcctcg | ccgcccgtcc | ccggcacacg | 180 |
| cgcagcccg | gcctctcggc | ctctgccgga | gaaacagttg | ggaccccctga | ttttagcagg | 240 |
| atggcccaat | ggaatcagct | acagcagctt | gacacacggt | acctggagca | gctccatcag | 300 |
| ctctacagtg | acagcttccc | aatggagctg | cggcagtttc | tggccccttg | gattgagagt | 360 |
| caagattggg | catatgcggc | cagcaaagaa | tcacatgcca | ctttggtgtt | tcataatctc | 420 |
| ctgggagaga | ttgaccagca | gtatagccgc | ttcctgcaag | agtcgaatgt | tctctatcag | 480 |
| cacaatctac | gaagaatcaa | gcagtttctt | cagagcaggg | atcttgagaa | gccaatggag | 540 |
| attgcccgga | ttgtggcccg | gtgcctgtgg | gaagaatcac | gccttctaca | gactgcagcc | 600 |
| actgcggccc | agcaaggggg | ccaggccaac | caccccacag | cagccgtggt | gacggagaag | 660 |
| cagcagatgc | tggagcagca | ccttcaggat | gtccggaaga | gagtgcagga | tctagaacag | 720 |
| aaaatgaaag | tggtagagaa | tctccaggat | gactttgatt | tcaactataa | aaccctcaag | 780 |
| agtcaaggag | acatgcaaga | tctgaatgga | aacaaccagt | cagtgaccag | gcagaagatg | 840 |
| cagcagctgg | aacagatgct | cactgcgctg | gaccagatgc | ggagaagcat | cgtgagtgag | 900 |
| ctggcggggc | ttttgtcagc | gatggagtac | gtgcagaaaa | ctctcacgga | cgaggagctg | 960 |
| gctgactgga | gaggcggca | acagattgcc | tgcattggag | gcccgcccaa | catctgccta | 1020 |
| gatcggctag | aaaactggat | aacgtcatta | gcagaatctc | aacttcagac | ccgtcaacaa | 1080 |
| attaagaaac | tggaggagtt | gcagcaaaaa | gtttcctaca | aggggaccc | cattgtacag | 1140 |
| caccggccga | tgctggagga | gagaatcgtg | gagctgttta | gaaacttaat | gaaaagtgcc | 1200 |
| tttgtggtgg | agcggcagcc | ctgcatgccc | atgcatcctg | accggccccc | cgtcatcaag | 1260 |
| accggcgtcc | agttcactac | taaagtcagg | ttgctggtca | aattccctga | gttgaattat | 1320 |
| cagcttaaaa | ttaaagtgtg | cattgacaaa | gactctgggg | acgttgcagc | tctcagagga | 1380 |
| tcccggaaat | ttaacattct | gggcacaaac | acaaaagtga | tgaacatgga | agaatccaac | 1440 |
| aacggcagcc | tctctgcaga | attcaaacac | ttgacccctga | gggagcagag | atgtgggaat | 1500 |
| gggggccgag | ccaattgtga | tgcttccctg | attgtgactg | aggagctgca | cctgatcacc | 1560 |
| tttgagaccg | aggtgtatca | ccaaggcctc | aagattgacc | tagagaccca | ctccttgcca | 1620 |
| gttgtggtga | tctccaacat | ctgtcagatg | ccaaatgcct | gggcgtccat | cctgtggtac | 1680 |
| aacatgctga | ccaacaatcc | caagaatgta | actttttta | ccaagccccc | aattggaacc | 1740 |
| tgggatcaag | tggccgaggt | cctgagctgg | cagttctcct | ccaccaccaa | gcgaggactg | 1800 |
| agcatcgagc | agctgactac | actggcagag | aaactcttgg | gacctggtgt | gaattattca | 1860 |
| gggtgtcaga | tcacatgggc | taaattttgc | aaagaaaaca | tggctggcaa | gggcttctcc | 1920 |
| ttctgggtct | ggctggacaa | tatcattgac | cttgtgaaaa | agtacatcct | ggcccttggg | 1980 |
| aacgaagggt | acatcatggg | ctttatcagt | aaggagcggg | agcgggccat | cttgagcact | 2040 |
| aagcctccag | gcaccttcct | gctaagattc | agtgaaagca | gcaagaagg | aggcgtcact | 2100 |

```
ttcacttggg tggagaagga catcagcggt aagacccaga tccagtccgt ggaaccatac    2160
acaaagcagc agctgaacaa catgtcattt gctgaaatca tcatgggcta taagatcatg    2220
gatgctacca atatcctggt gtctccactg gtctatctct atcctgacat tcccaaggag    2280
gaggcattcg gaaagtattg tcggccagag agccaggagc atcctgaagc tgacccaggt    2340
agcgctgccc catacctgaa gaccaagttt atctgtgtga caccaacgac ctgcagcaat    2400
accattgacc tgccgatgtc cccccgcact ttagattcat tgatgcagtt tggaaataat    2460
ggtgaaggtg ctgaaccctc agcaggaggg cagtttgagt ccctcacctt tgacatggag    2520
ttgacctcgg agtgcgctac ctcccccatg tgaggagctg agaacggaag ctgcagaaag    2580
atacgactga ggcgcctacc tgcattctgc caccccctcac acagccaaac cccagatcat    2640
ctgaaactac taactttgtg gttccagatt ttttttaatc tcctacttct gctatctttg    2700
agcaatctgg gcacttttaa aaatagagaa atgagtgaat gtgggtgatc tgcttttatc    2760
taaatgcaaa taaggatgtg ttctctgaga cccatgatca ggggatgtgg cgggggggtgg   2820 ctagagggag aaaaaggaaa tgtcttgtgt tgttttgttc ccctgccctc ctttctcagc    2880 agcttttttgt tattgttgtt gttgttctta gacaagtgcc tcctggtgcc tgcggcatcc   2940
ttctgcctgt ttctgtaagc aaatgccaca ggccacctat agctacatac tcctggcatt    3000 gcactttttta accttgctga catccaaata gaagatagga ctatctaagc cctaggtttc    3060
tttttaaatt aagaaataat aacaattaaa gggcaaaaaa cactgtatca gcatagcctt    3120
tctgtattta agaaacttaa gcagccgggc atggtggctc acgcctgtaa tcccagcact    3180
ttgggaggcc gaggcggatc ataaggtcag gagatcaaga ccatcctggc taacacggtg    3240
aaacccctgc tctactaaaa gtacaaaaaa ttagctgggt gtggtggtgg gcgcctgtag    3300
tcccagctac tcgggaggct gaggcaggag aatcgcttga acctgagagg cggaggttgc    3360
agtgagccaa aattgcacca ctgcacactg cactccatcc tgggcgacag tctgagactc    3420
tgtctcaaaa aaaaaaaaaa aaaaagaaa cttcagttaa cagcctcctt ggtgctttaa     3480
gcattcagct tccttcaggc tggtaattta tataatccct gaaacgggct tcaggtcaaa    3540
cccttaagac atctgaagct gcaacctggc ctttggtgtt gaaataggaa ggtttaagga    3600
gaatctaagc attttagact ttttttttata aatagactta ttttcctttg taatgtattg    3660
gccttttagt gagtaaggct gggcagaggg tgcttacaac cttgactccc tttctccctg    3720
gacttgatct gctgtttcag aggctaggtt gtttctgtgg gtgccttatc agggctggga    3780
tacttctgat tctggcttcc ttcctgcccc accctcccga ccccagtccc cctgatcctg    3840
ctagaggcat gtctccttgc gtgtctaaag gtccctcatc ctgtttgttt taggaatcct    3900
ggtctcagga cctcatggaa gaagaggggg agagagttac aggttggaca tgatgcacac    3960 tatgggccc cagcgacgtg tctggttgag ctcaggaat atggttctta gccagtttct     4020
tggtgatatc cagtggcact tgtaatgcg tcttcattca gttcatgcag gcaaaggct     4080 tactgataaa cttgagtctg ccctcgtatg agggtgtata cctggcctcc ctctgaggct    4140
ggtgactcct ccctgctggg gccccacagg tgaggcagaa cagctagagg gcctccccgc    4200
ctgcccgcct tggctggcta gctcgcctct cctgtgcgta tgggaacacc tagcacgtgc    4260
tggatgggct gcctctgact cagaggcatg gccggatttg gcaactcaaa accaccttgc    4320
ctcagctgat cagagtttct gtggaattct gtttgttaaa tcaaattagc tggtctctga    4380
attaaggggg agacgacctt ctctaagatg aacagggttc gccccagtcc tcctgcctgg    4440
```

| | | | | | |
|---|---|---|---|---|---|
| agacagttga | tgtgtcatgc | agagctctta | cttctccagc | aacactcttc | agtacataat | 4500 |
| aagcttaact | gataaacaga | atatttagaa | aggtgagact | tgggcttacc | attgggttta | 4560 |
| aatcataggg | acctagggcg | agggttcagg | gcttctctgg | agcagatatt | gtcaagttca | 4620 |
| tggccttagg | tagcatgtat | ctggtcttaa | ctctgattgt | agcaaaagtt | ctgagaggag | 4680 |
| ctgagccctg | ttgtggccca | ttaaagaaca | gggtcctcag | gccctgcccg | cttcctgtcc | 4740 |
| actgcccct | ccccatcccc | agcccagccg | agggaatccc | gtgggttgct | tacctaccta | 4800 |
| taaggtggtt | tataagctgc | tgtcctggcc | actgcattca | aattccaatg | tgtacttcat | 4860 |
| agtgtaaaaa | tttatattat | tgtgaggttt | tttgtctttt | tttttttttt | tttttttgg | 4920 |
| tatattgctg | tatctacttt | aacttccaga | aataaacgtt | atataggaac | cgtaaaaa | 4978 |

<210> SEQ ID NO 2
<211> LENGTH: 79001
<212> TYPE: DNA
<213> ORGANISM: Homo sapiens

<400> SEQUENCE: 2

| | | | | | |
|---|---|---|---|---|---|
| ataaaaatta | aaaccctga | tagtatcagc | acatacacag | aaatcactcc | attatgcaaa | 60 |
| gttcatcctc | tattatgaaa | ggcaaaatgt | ctacatttcc | tatcaaccac | tggcttcaat | 120 |
| tcagtaaaac | ttgcatacca | agtaggcaag | gtggaaaaga | aaaggcaga | acatttcatg | 180 |
| tatttcaatt | cagacgcata | aaaatgtcaa | gccctacacg | ttatcagctt | tcgtatacac | 240 |
| cgtcttctgc | attcgcctgt | acgggccaat | gggctagctg | gtcggcgttt | gatgcttgaa | 300 |
| gtgatggaac | ggagtacggg | gttaaatcca | ctaccctctc | cccacgcact | ctagtaatta | 360 |
| ctctatttcc | acgtcatgtt | tccgggtgtg | tgtgtccctg | ctcacgcaga | aactgaagtt | 420 |
| caaagcaggc | ggagtcaccc | atgttctttt | tgttgtcccc | agaacccaat | tcaggagttg | 480 |
| ggtccccaga | ggatctggag | atacctgggg | actatctaac | tagctgattc | ccgcgtggta | 540 |
| agaggctctc | aacctcgcca | ccacgtggtg | ccaaggccg | ggaaaaggga | gagcgggcag | 600 |
| gagggagctg | tatcaggggc | atttaaagtg | ccttgacgtc | acgcactgcc | aggaactcag | 660 |
| ctgagttttc | agcaggacat | tccggtcatc | ttccctccct | ccccccgggc | ttctgtgccc | 720 |
| aagtcctcgg | ctcttccctc | gctgtggcgg | agggaggagc | accgaactgt | cggaacagcc | 780 |
| agcacagggg | cgtatcagtc | tcctcttggc | tccgcccttt | ctcctagctg | ctctcctcat | 840 |
| tggtcagtgg | gcggggcttc | ggctgtaccg | cacacgcact | gggacctctg | ggtggccgaa | 900 |
| cgagctggcc | tttcatgaat | tatgcatgac | ggcgtgcctc | ggccaggctg | gggctgggcg | 960 |
| aggattggct | gaaggggctg | taattcagcg | gtttccggag | ctgcggcggc | gcagactggg | 1020 |
| aggggagcc | gggggttccg | acgtcgcagc | cgagggaaca | agcccaacc | ggatcctgga | 1080 |
| caggcaccc | ggcttggcgc | tgtctctccc | cctcggctcg | gagaggccct | tcggcctgag | 1140 |
| ggagcctcgc | cgcccgtccc | cggcacacg | gcagccccgg | cctctcggcc | tctgccggag | 1200 |
| aaacaggtga | aggggtgca | gggtggggcc | gttggggagg | cctggggacc | cggggctcc | 1260 |
| gcagcggcag | ggggcctctg | ggaccttggg | gatgttgtga | tggacgctgc | agtggggccg | 1320 |
| ggagagatga | agagacgcgg | agggtcgccc | tgagggaaga | ctcttcggga | tgacaggagc | 1380 |
| gggcctcgga | agggactcgg | ggcgctggag | ggaagtttcg | ttcttcggag | aaacagaacg | 1440 |
| cgctcgaggg | ggcaccgtgg | ggcgagggcg | cactcggttg | cggcggcagg | agtgagggac | 1500 |
| agtcccccga | tttcctgctc | cctggggccc | tgggacgtt | ccggccaccg | gagcgactgt | 1560 |
| cacgccgacg | gggatcaccg | gcgcgagtgg | ggggtcggaa | agcgcctcct | ccccgcccgg | 1620 |

```
tcggcggctc ccgctgagcc acttcctccg cttgccctgt tcccgctcct tcaggagaca     1680
gctgtgccct tttggaggca ggaataggtg tgtctgtcgc ctgcagcctt acgggctggc     1740
tggtcgtggg taggctttat tgcataagaa tcaagtttcc tgtagggaaa ttgacagacc     1800
ggtactcttt ctaaattccc tcgcatcttt ttctaggtta aattatgctc cccccacgtc     1860
cccgccttgt aaaaagaga aaaaagaca aaataaaatc cccatcaacc cgtcaagcca       1920
gctctagaga gagaaataaa cctcttgaca ttgtccttt ccaaatacct ggtaaagtcg      1980
gccagaagat aaataattga gccattgcat ttactggatt gtggtgttgc ttaattgcat     2040
aggacggaat gaaccaattg agagtgggag ttttctgtct cagagccaag atcttgggta     2100
aatgcagagg agagggaaac aaagacaggc tggccttgaa aaaccatgt gtgcaaactt      2160 tacatgcatt tgggggtgt ggttgcactg aagttaacaa gattcaaacc gtcgcccaag      2220
ttggtatttc catgtttggt acacatcact ctgtgccata tcaggtcgtt gttaagtgtg     2280
gtgacaaaat cagtggttag tcattttttt aattaaaaat gtgtatagtg tgtacctgct     2340
ggtcttactg tatgtgcaac taaaggttta catagtctgt gtatgggttg taaattttg      2400 gctggctgtg ctgataaagc attgggcttg aataaagcaa agcagaaaat catctcaatc     2460
ttttatatgt ggatttagac tgtgttatga cttggttcag ccagttttct atcttatttt     2520
atattaaata tgtctgtgtt ctctgagtca gcacatttat ttccttatta catgttccag     2580
acaggagtgc tagcccagtt tttgttcagt ttgcacagtg ggatggggaa acaagtctgg     2640
aatttaaaaa aaaatgtttt agaggttgga gccttgattt tagtctctat attagcacat     2700
ccatcacaaa gaaccattag taaattcatg aatcttttgt tttttatgta gttcatttga     2760
gaagaataat cacttagaaa tatccacagt gccaggcatg gtggtgcaca cctctgatcc     2820
cagctaattg aaggctgagg tgggaggatt ccttgagtcc aggagttgag tctggtctgg     2880
gcaacatggt gagaggccag gaattgggtc tagagtctag tctaagcacc ataatgagaa     2940 cccatctta agaaagaaag aaaggaaagg aggaagaaag gaaagaaaaa gaaatacccca    3000 cagcacagtt atgaattaac ccacaaagga cttgtgaggt gggtagttca cataacaatt     3060
accctaatat cgtagataag aaaattgagg ccaaaggatc aagacacttg gccaacgcag     3120
cagagtgcca tagtggtgga atttgtgcct ccttctgtat attttgtgaa aagtatcagt     3180
gaaattcttt tttttttttt ttttgagtca gagtcttgct ctgttgccca ggctagagtg     3240
cagtggcgca atcttggctc actgcaacct ctgcctcctg ggttcaagcg attctcctgc     3300
ctcagcctcc caagtagctg ggactacagg cgtgcgccac cacgcccagc taattttgt     3360 attttagta gagaccgggg ttttaccata ttggccaggc tggtcttgaa ctcctgacct     3420
tgtgatttgc ccacctctat ctcccaaagt gctgggatta caggtgtgag ccaccgcgcc     3480
cagtaagtat cagtgaaatt ctaacatata tctgaacagt aaaataccac caataggctg     3540
aaagacttca tgggaggtaa atattcaata aacaggtgaa aaaagaaata caaatggagc     3600
ttgcttagat tattttttcta attgctatgt ctaacttggg aagtgaggaa ctgttttgg     3660 tcagcataat ttaccatcag aatttagcta tttactaatg aaaagaaata ctaatctagg     3720
tttgttttag attaaggaca gtcatgacct aaatgtcatt taaaccagag tgcattgtgg     3780
cttgatcagt ggtcatttct gtctctagaa agttgcttta acttctctgc ctctacgtgt     3840
ctcttgacat tcagatatga ggtgggtag aggtggtgac caactttcca gacgcctgag     3900
tccaaacctt cttagcttat ggttttctta ggtgatgtgc aaatcaacaa atatatactt     3960
```

```
tttttttttt tttttttgagt tggagttgca ctctatcacc caggctggag tgcagtggca    4020
tgatcgtggc tcactgcaac ctcctcctcc cgggttcaag tgattctcgc acctcagcct    4080
cctgagtagc tgggattaca ggtgcccgcc actacgcccg gctaattttt gtatttttag    4140
tagagataag gtttcactat attgaccagg ctggtctcaa actcctgacc tcaagagatc    4200
tgcccacctc agcctcccaa agtgctggga ttacaggcgt gaaccacctt gcctggccaa    4260
catatatata cctttgcaa cttttgtcaga gttgctatga agaataagtt gtatcttgtt     4320
cacagaaatt gcagtctact gggggagctg ataaatgttt taaccatcca atgtaacatg    4380
ttgtcatcaa agagatggtg agactttaca cttgtgctaa caaggtagct gttctacata    4440
aaagaacata cagtacagat gtagaacttt tctgttatca tagaacgttc tattggacag    4500
tgctaggctg aatgctacag atcttcagag aaaggagagg ttatgaggcc tggagttgtc    4560
tagaaagtct ttttgccaaa gagggatttc aactgggtcc caaataatgg gtggaatttg    4620
ataggtgtaa agaatttgcg gtggtttatg cctgtaatcc cagcactttg ggaggctgag    4680
gcaggaggat tgcttgagcc caggagtttg agaccagctt gggcaacgtg gtaaaactcc    4740
ctctccccta aaaataaaaa aaattagcca ggcctggtgg cgtggacctg tagtcccagc    4800
tactggtgag actaaggtgg gaggatcacc caagccccgg gggttaaggc tgcagtgagc    4860
cgtgatcccg ccaccgcact ccagcctggg tgacagagtg agaccctgtc tccaaaaaaa    4920
aaaaaaattc ctggtagccc ggtagactag gagggtaagt aggggagaag tgattactta    4980
caaaagacat tgaatacagg accaaggaat ttcagttctg ttcttttgta ggggaagctt    5040
ttaaaacttt cggggcgccg ggcgcggtgg ctcacgcctg taatcccagc actttgggag    5100
gcccagacgc gcggatcacg aggccaggag atcgagacca tcctggctaa cacggtgaaa    5160
ccccatctct actaaaaata caaaaaaaag tagccgggcg ttgtggcggg cgtctgtagt    5220
cccagctact cgggaggctg aggcaggaga agagcgtgaa ctcgggaggc ggagcttgca    5280
gtgagccgat atcgcaccac tgcactccag cctgggcgac agagcgagac tccgtctcaa    5340 aaaaaaaaa aataaataaa taaataaata aataaaactt tggagccgaa gcactgatgt    5400
ttaatcatag agtgcttact atgtgttagg cacaggcctg attgcctgat gctggttaat    5460
ttgtacaaag taaatcagtg catatgccct ctgccctagg ggagttatta actggagtct    5520
gacattgtac aaaggtaggt atcctgacta gtttgatttg gtactttggg tgaaaaaagt    5580
atagtgtgct taagtgcaga agtgtttttt gaggattttt gattggatac aaaccaccac    5640
tcatatttta tgtctttggc acttaaaaat ttcaccataa cttttgagtc atttataaaa    5700
accactgaaa gagtacttga gggacatccc cgaatcctga agaacttctg gtgttctgga    5760
gcagcctcag tgagatccag gaggatggca ttgctgggct ggcccagccc ttattgatta    5820
tggtgtaaag aattaatatg gtggttatat actctttgtt agacaccttg gcttacaaga    5880
cgtaagcgta aagtgtagtg cgctttagtc agtatggcca catggtcctt tggtggtaaa    5940
ttgtttgaga tgcctccagt ttttaaaagg agtagcatat cgggccagga gcagtggctc    6000
atgcctataa tcccagcact ttggaaggcc gaggcaagag gattgcttga gcccaggagt    6060
tcaagaccag cctgggcaac atagtgagac cactttgttt ctttaaaaaa aaaaaaaagg    6120
caaaaacagg ctgggcatgg tggctgatgc ctgtaatccc agcgctttgt gaggcagagg    6180
tgagcggatc acttgaggtc aggagtttga gaccagcctg gccaacatgg taaaaccccg    6240
tctctactaa aaatacaaaa attagccagg tgtggtggca cacgcctgta gttccagcta    6300
ctctggaggc tgagccagga gaattgcttg aacctgggag gtggaggctg cagtgagcca    6360
```

```
agatcctgcc actgcactcc agactggggg acagagtgag acattctgac agtgctacac    6420
tgaatgctac atgtcttcag aggaaggaga ggttatgagg cctgggaata acatatggaa    6480
gaatgaattt ctgttatggt cagttctcat ttgtcatgtt aggattactg caactcttac    6540
ccagccgggt gtggtggctc atgcctgtaa ttccagcact tgggaggct gtgggcggat     6600
cacgaggtca ggagatcgag accatcctgg ctaacacggt gaaactccgc ctctactaaa    6660
aatacaaaaa attagcccag cgtggtggca gacgcctgta gtcccagcta ctcaggaggc    6720
tgaggcagga gaatggcatg agtcctggag gcggagcttg cagtgagctg agatcgtgcc    6780
actgcactcc agcctgggca acagagtggg actccatctc aaaaaaaaaa gaaaaaaaaa    6840
aggattaccg caactctttta attcagatca gcaaacatgt tgagagccag gtattgcgtc    6900
aggcaggatc caaggataat gaaatattgt ccgttttcat gaaactggag atgttgcagg    6960
gaccgaggtg tgtgctatgc cagtatggaa gtaggacagg ggagacgaca gggcagtgag    7020
tggttcaaga ctctggctct gaagtcaaac agatctggga ctgaatcctg gatctgccac    7080
ttcctagtca gaatctgagc ctctattttc ttatctgtaa aagaagatta taacagtgct    7140
tatcttgtag gtactgttga cgattcaata agataatgtg gataaaatgc ttagcatagt    7200
gcctggcaca tagtaagagc tcggtaaatc taagttctta ctaaatatcc aagaaaagag    7260
attaattctt ttcaggagtg agagaaagtc atcattattg aggggcttta tcagatggga    7320
acacctgaat agggttttat aggatgaata ggaattcttt ccacgaagtt gcgttacaaa    7380
aagttgcatt caaggctgaa ggaacatgag ggtgcagagg cttaaaacag ccttgtgtgt    7440
tcagggagct ataagtagaa gttcttaatt taggagaact aaaccaaggg gaaaggaggc    7500
caaggaacca cagttcttat ccctttctg ttaataattg ggtttaaatg tcattaaaat     7560
aagttatttt gtccttttta gaaaagtaat aacatgctat tataaaaaaa aagacttgta    7620
ggaatataaa atgtgtgttt tacatgtatc ctgttaattg acttgctttt attcagattt    7680
tttgcagccc tttctgttta ccaggttatc ttggagacat atttattcca aattcctttt    7740
ttttttttt tttgagatgg agtctcgctc tgtcgcccag gctggagtgc agtggcgcta    7800
tcttggctca ttgcaagctc cgcctcccgg gttcacgcca ctctcctgcc tcagcctccc    7860
gagtagctgg gactacaggc gcccgccacc acgcccagct aatgtttttt ttttatatt    7920
tttagtagcg acagggtttc accgtgttag ccaggatggt ctcaatctcc tcacattgtg    7980
atccgcctgc ctcggcctcc caaagtgctg ggattacagg cgtgagccag cacgcctggc    8040
cttccaaatt cctttaaca gcctagcaaa agaataataa ggaaggtaaa tctgccccta    8100
caagaaaata atgcttcgac gatccggctt tccttcctgc taccccagc cataagaata    8160
aatgaccttg ctcatcactg aaattttacc tgacctttga attttaact gcgtcagcca    8220
aagaacttat attttgagta ttcctaaggt gattgctatt gtagttttga aacacttggt    8280
tggtatgttt gagggtttca tggtccaaag ttactatagc agttaaaaga gtggactatc    8340
aggtcagacc tattgggctt taatcccagt tctgccttct cttagacctt gggcctgttg    8400
ttttcacttc tctggttttc agtttctctg tccacaattg tggaaacgag gtccacttgt    8460
agagtaattg agaggatgaa gcaagatgat gcatatcaag tactttgcat agtgccgggc    8520
agacaggtaa cattcaagtg ctaataatta ctattattac tatttatttt ttgagacagg    8580
ttctcactct gtcacctagg ctggagtgca gcggtgagat cacagctcat gacagccttg    8640
acctcctagg ctcaagtgat cctcctgcct cagccttcgg ggtagctggg gctacaggtg    8700
```

```
tgtgctacca ccctcagcta attttctaat ttttttgagt caggatctcg tcacgttgcc    8760
taggctgaat tactcttatt aaaaactata atatcaggcc gagtgcggtg gctcacgcct    8820
gtaatcccag cactttggga ggccaaggcg ggtggatcac ctgaggtcag gagttcaaga    8880
ccagcctgcc aacagagtg agacccccccc cgtctctact aaaaatataa aaattagcca    8940
gttgtggtgg tgggcacctg taatcccagc tactcgggag gctgaggcag gataatcgct    9000
tgaacccggg aggcggaggt tgcggtgaac cgagatcgtg ccactgcact acagcctggg    9060
tgacagagtg agactctgtc tcaaaaaaac cgaaaaacaa aaagcataat tagggtggta    9120
acgcttatac ataggggcag gtggaataaa acataattag gaggtcgggc atggtggctc    9180
acgcctgtaa ttccagcact tgggaggcc gaggcgggtc aggagttcaa gaccagcctg    9240
cccaacatag tgagaccccg tctctactaa aatataaaa tttagcctgt tgtggtggcg    9300
ggtgcctgta gtcccagcta cccgggaggc tgaggcagga gaattgcttt tgaacccagg    9360
aggtgggggt tgcagtgagc tgagatcgcg ccgctgcact ccagcctggg agacagagca    9420
agactccgtc acaaaaacaa aaaacaaaaa actgtcatat caaaaactaa actaaaatgg    9480
taatatctgt tagatattac aaagtcaggc aaattatgat tcatggcagc cactaatgac    9540
ccaaaggaga gaaagaataa ttagcagatt ctaacctaat gggaaaaaaa ctaaatgaat    9600
agggatgggg gacttacatt ctgttagagg aaattgaggc tgtcatataa aaggaatagg    9660
taaggcaaac tgtaaattcc tgtttacaca aatgcccttc tgataaatct ctgcattgcc    9720
cacagtccat gattacctct cccttatttt aagtaatatt taacacatta aaaatggatt    9780
accacccaag gaattgctcc cgacccagaa agtgcaggta gtgttgaagg tttgagggga    9840
agaggaatga ttagagttgg ttgtgtctca ggaagaagcc aacaggagga accttatttt    9900
gagtcaggta aagaaggtgg gagtgaggag gcatcccggt ggccaggtat gaagctggga    9960
gctgattgct gcacattact cagctgaatt aaatgtgccc tcacatctgt gtgtgtgcgt    10020
acatgcaaat gtcatgtgt atgagttagt tggaggggta gacctttatt ttcctgtcct    10080
gtaactttcc tttgcaaact aatctgtatt cagaacagtg ttgcagttaa gaaccaccca    10140
gcttgtccat gaaacaggtt ctctcacccc atctccccag ttttagagaa ggcaggaaag    10200
aaaaggcagt gcttttcttt ttttcctggcc gtatgcgggg caggaagaag ccagcagagc    10260
ttgaaagaga aagtaaacct tctgggaaat aaacggcttg gcttccctat tgtgaggag    10320 gagtgcaaat tattaggggg atgtttgggt agttttttgta gaagccattt ctgaaaactg    10380
atttggatta gtgaaggtaa gcccaattta ggaaaaccct gcccagtctg gtgtcagcca    10440
cctgtttccc gctttgtttg attgatttga ttagtttgtg gtattctgac ctctcatttt    10500
tattacaaga gttggaagat ttgagtctga acttgagcac ctgcttcggt gaaagcttcc    10560
taaaatgcat gttttttcac atttttttctc atgttcattt tgtttttgctt tttagcaaac    10620 acttttctg acagaatcta aaagcattag acttttcttg ttttcccctt ctctccccac    10680
aatgtaatct tgaaacccca aatgttagct gtgtaaatta cctctcccgt aaaccaaaca    10740
aagtgcaata ttgcattgag ttagcattga aatagtcggc ctttgaattt ttttctactt    10800
gtggtttaga cataataaat atttcatctc agactgactt tctcgacaaa tcagtttttgc    10860 atttgggcct cttttcatca gtatgtttag ggaaagcaca tttattgaaa cattaaccaa    10920
aatgaaacat aattaggagg ccgggagcga tggctcacgc ctgtaatccc agcactttgg    10980
gagaccaagg catgtggatt gcttgaggtc aggagttcaa gaccatcctt gccgacttgg    11040
tgaaatcctg tttctactga aaatacaaaa aactagctgg gtgtggtgac gcgtgcctgt    11100
```

```
aatcccagct actctggagg ctaaagcaag agaatcgctt gaacctggga ggcagaggtt    11160
gcagtgagtc gagatcgtgc cactgcactc cagcctgggc aacagagact ccgtctcaaa    11220
caaccaaaaa aacaaaaaca agcataatta gggtggtaac gcttatacat aggggcaggt    11280
ggaataattg aagcattctg gagccagaaa taatcaactg attaagaata atctggctgg    11340
gtgcggtggc tcacgcctgt aatcccagct actcaggagg ctgaggcagg agaatcgctt    11400
gaacctggga ggtggaggtt gcagtgagcc gagatcgcgc cattgcactc cagcctgggc    11460
tatggagcaa gactccatct caaaaaaaaa aaaaaaaaa atcctgtttc tgcagaaata    11520
tcccaggtgt cctgggtcag cagtgcccca tagattccac ggacgtttac cctaagtttt    11580
ccaatgggag ttcatacctc tatcccagt gagaatattt tctgagtaat gggaatgaga    11640
ttggagatgt agggtagaga agatccatac agtctttggg ttaaacttttt tcctctttgc    11700
ctaggaaaga ttaatgctaa tcttaaccac agatttgtag taagaatgta tcagttttgt    11760
cattcagttc tagactccag ttttctttat tgtaatacca atattttaga gtaaattttg    11820
aaatgaatca gtacaaaaga tatgtagtaa gtggaaagtt agtccgcacc ttatccttgg    11880
gactcttttcc cagggacagc tagttaccta ctatttatct ctcctgagtt acttcatatg    11940
tatgcatgca aacatgttat tctctgggtg ttgttccttc catatatagc agcaaataca    12000
ccaaactctg tattttgctt tttgtcactt tatcttagag aatactcaat gcaaatacat    12060
gtgtatatac ctcatgttta aaaatctac atagtaaaat tagccaggca tggtagtgtg    12120
tgcctgtaat cccagctact cgggaggctg tggtgggaga atcacttgaa ccctgagatc    12180
acaccactgg actccagcct gggccacaga gcaagattct gtctcaaaaa acaaaaacaa    12240
aaacaaaaaa actacagagt agtattctag gctatgcata tcataaattt gatttcctaa    12300
tgataggcat agatgatttg cctgggcggc aaattagcgt tggctgtgtc tcaggaagaa    12360
gccaacagga ggaaccttat tttgagtcag gttccaaaga cagaaacatt gtctgacatt    12420
tgttttttggg cttatatgaa taaatctgta cacatatatt tttaatgttt taatcgtaat    12480
atgtatacta tttggaaatg tggcttttta gttaacagag tgcatgtttt accccattgc    12540
acttaaacat taacttgggg ataattaaat gagtctgtca cttggacagg caggaattgt    12600
accccccaca aacccataaa ccgccaattt ttttttttttg agacagagcc tcattctgtt    12660
gcccaggctg gagtgcagtg gtgcgatctg ggcccactgt aagctcagcc tcccgggttc    12720
atgccattct cctgcctcag cctcccaagt agctgggact acaggcgccc gtcacaatgc    12780
ccggctaatt ttttgtattt ttagtagagt cggggtttca ccatgttagc caggatggtc    12840
tctatctcct gaccttgtga tccgcccgct ttggcctccc aaagtgctgg aattacaggt    12900
gtgagccacc gcacctggcc ggttttttttt ttttttttttg agatggagtc ttgctctgtt    12960
gccaggctgg agtgcaatgg catgatctcc gctcactgca acctccacct cccgggttca    13020
agtgattctc ctgcctcagc ctcctgagta gctgggacta caggcgtgtg ccaccacgca    13080
cagctaattt ttgtaatttt agtagagatg gggtttcatt aataatcatt aatattagac    13140
aactgtcaga ctcacagtgg tggatacaaa ctttctcaaa ttctgatttt tactctaaag    13200
ctcaaattt atcattggca acaaatattg tcagttgctt tccctgaaca gacagcttcc    13260
cttcttttcat ttttgagaaa atatctgcca gtatcccagt tggtttatca atcattcttt    13320
ctcttttttt ttttgagacg gagtctcact ctgtcaccca ggctggagtg cagtggcatg    13380
atctcggctc actgcaacct ccacctccca ggttccagca attctcctgc ctcagcctcc    13440
```

```
cgagtagctg ggattacagg ggctagcagc cacacctggc taattttttgc attttttagta   13500 gagacagggt tttaccatgt tggccaggct gatcttgaac tcctgacctc atgatatgcc    13560
caccttggcc tcccaaagtg ctgggattac aggtgtgagc cattgcgccc ggctctatta    13620
tttcttttct ttctttcttt ttcttttttt tttttgagat ggagtttcgc tcttgttgcc    13680
caggctggag tgcaatggcg cgatctcggc tcaccacaac ctccgcctcc cgaattcaag    13740
tgattctctt gcctaagcct cccgagtagc tgggattaca ggcatgtgcc accacacccg    13800
tctagttttg tattttttatt agagatgggg gtttctccat gttggtcagg ctggtctcga    13860
actcccaacc tcaggagatc tgcctgcctc agcctcccaa agtactggga ttacagttttt   13920 gagccacctg acccggtttg cttattattt cttttaaatt taaaaaataa taaataaagg    13980
ggccatgaga gcgaagagtt tgagaaaggt tggtctaaag gttttaacat aagaatccct    14040
gggttatttg cttaaaaaga agaaagaatc tatggatctg cctgagaggg tctgatgtag    14100
tttatctggg gtcatcctca caggcatagc agatattctg attcagatgg tccttggtcc    14160
ttagtttgag aaatgtggct ttacaaggcc catagaaatat aaagtcttct ttggattagt    14220
gaagtcatgt ccacagggtt tagaaaatgt ttttgtttta gagataaagg taagtggaag    14280
agtagacatg tagtgaatga gggaaaatgt tttagagatt tctttttatt ctgtttactc    14340
ttcttggtat gcacgtacct gaatattaag gatatttat gaagtcatga cattaccaga    14400
ttaatgttgg ttttgttttta aggtactttc tgactgctgg ggtaattcc tacagacgat    14460 tctggtaaag aatagccttt aagtttttaaa agtgttgact tatttcagat gtcttaataa    14520
agttaacttc cagttattac atgtaacgta tataaagctc tcattttcct ttattctcgt    14580
taattgtttg cataacaaat tcaaagggaa atttgcttgg cagagatcag atagcagaga    14640
tgagatttaa aaacaggtaa tttggctact agcctgggag tttgaagatt ccaagtttgc    14700
atccatgtgt agtcacttaa catttctgtc cttatctgta aatgggaata acacctactt    14760
gatagggttg ttacattatc ttggccacct caggttctct ttggctgagt gattgactgg    14820
aaaacgcaat gtgaattcat gcttcagact gggttctttt tttttttttt ttttgagatg    14880
gagtttcact cttattgccc aggctggagt gcaatggcac gatctcagct cactgcaacc    14940
tctgcctccc aggttcaagc gattctcctg cctcaggctc ccgagtagct gggattacag    15000
gcatgcacca ccatgcctgg ctaatttttt tgtattttta gtagagacgg ggtttcactg    15060
tgttggtcag actggtttca aactcctgac ctcaggtgat ccacctgctt cagtctccca    15120
aagtgctggg attacaggca tgagccaccg cacccagccc aggctaggtt ctatatgggt    15180
gtgcttttta gaatttagat catgggctat ccccaacaca aactggataa tgtttctttc    15240
tagattctct ctaagcgtgt attctctttc tttcctaggc acagccacca cttcacttac    15300
attgtgggat tataatttca tgagtagtgg aatttcctta accttctctt gtgtgggagc    15360
tgaaggacaa aatgagatat tctctgaaga gtggttacat catgcaaaac tatgatgtgt    15420
aatgaggtca cttagttttc taagtacatt atacattttg ataagatttt catagaaaag    15480
cttgtctcct tggggagatc actcatcttc catcttgact attatttaaa ctttatgggt    15540
cagatttatc ttttttaaaaa cttaaccata aagctcaatt aatttttttt tttttttttt   15600
gagacggagt ctcgctctgt tgcccaggct ggagtgtagt ggcgcgatct cggctcactg    15660
caagctctgc ctcccaggtt catgccattc tcctgcctca gcctcctgac tagatgggac    15720
tacaggcgcc cgccacgatg cccggctaat ttttgtatt tttagtagag acggggtttc    15780
accgtgttag gatggtctcg atctcctgac ctcgtgatcc acccgcctcg gcctcccaaa    15840
```

```
gtgctgggat tacaagcgtg agccaccgcg cccggctcaa ttaatatatt ttaaaaatta    15900
atagacttta ttatttttat tttattttat ttttgaggca gagtctcgct ctgtcaccca    15960
ggctgagtgc agtggtgtga tcttggctca ctgcaaactc cacctcccgg gctcaagtga    16020
ttctcctgcc tcagcctcct aagtagctag gattacaggt gcctgccacc atacccggct    16080 agttttgta atttagtag atacgtgttt tcttctttt cttttctttt ttttgagatg    16140
gagtttcact cttttgccc aggctggagt gcaatggcat gatctcggct cactgcaacc    16200
tccgcctccc aggttcaagt gattctcctg cctcagcctc ccaagtagct gagattatag    16260
ttgtctgcca ccacgcctgg ctaatttttt gtatgtttga tagagacagg gtttcactat    16320
gttagccagg atgtctcgat ctcttgacct cgtgatccgc ctgccttggc ctcccaaagt    16380
gctgggatta caggcgtgag ccactgcggc cagtctagac tttatttttt aaagcagtgt    16440
tagttttaca gaaaaattat gtggaaagta cagagagttt ccatataccc cttactttct    16500
cccacaactt ctattattaa catcttgcat tagtatagta cgtcccttac aactaatgaa    16560
ccaactcgat acattattat taaccaaatt cctgagttta ttttatttct attttatttt    16620
tattattatt ttttttaga ggtagggtct cactgtgttg tccaggccag gttgcagtgg    16680
catcatcata gcttgctata gcctgaaact cctgggctca agcaatcctc ctgcctcagt    16740
ctcccaaagt gttggaatta caggtgtgag ccactctgtc cagcctgaag tccatagttt    16800
acattacatt tcactctgtt gagcattcta tggattttga caaatgtgtg atgatgtata    16860
tttgccagta cacaattata taaaatagtt ttactgccct agaaaccccc tgtgctccac    16920
ctattcattc ctctgctgaa ccactggcaa ccactgatct tttataatat ctccatagtt    16980
ttgtcttttc cagaatgtca tatagttgga catacagtgt gtagccttt cagattggct    17040 tctttcagta aatgatatgc atttcaggtt tcttcatgtt tttttgtggc ttgataggtt    17100
gtttcttttc attggtgagt aatactctat tgtatggata taccacatgt tgtttatcaa    17160
acattcacct gaaggataga catcttggtt gcttccaagt ttgagcagtt atgaataaag    17220
ctgctataaa cattccagtg caggactttt cacctcctct ggataaatat caaggagtgc    17280
aattgctaga tcatatggta agagtatgtt tagttttgta agaagctatc aaactatatt    17340
caaagtgact gtaccattat acattcccat cagcagtgag tgagagttcc tgttactcca    17400
catcttcacc agcatttagt ggtgtcagtg ttttggattt tagccatttt aatgggtgta    17460
taatggtata cctattaaaa ttggtttttt ttggagacag agtttcacag tttcactctt    17520
gttgccctgg ctggagtgca atggcgcaat ctcggctcac tgcagcctcc gcctcccagt    17580
ttcaagtgat tctcctgcct cagcctccca agtagctggg attacaggtg cacgccacca    17640
tgttctgcta atttttttgt atttagtag agatgggggtt tcactgtgtt acccaggctg    17700
gtcttgaact cctgagctca ggtaatccac ctgcctcagc ttcccaaagt gttaggatta    17760
caggcatgag ccaccgcacc tggcctcaat tttttttttt ttttttttga cagagtttt    17820 tgctcctgtt gaccaggctg gagtgcagtg gcacaatctc ggctcactgc aacctccgcc    17880
tcctgagttc aagcgattct cctgccacag cctcctgagt agctgggatt ataggcgccc    17940
gccactacgc ctggctaatt tttttttttt ttttaattag agacgaggtt tctccatgtt    18000
ggtcaggctg gtcttgaact ccccgttctc aggtgatccg cctgcctcag cctcccaaag    18060
tgctgagatt acaggtgtga gccaccgtgc ccgcctgtt ttggctttta ctgtgaagac    18120
gtgttagccg ctgtgatgac tagcaagtgt ggccctccac ccagtcgctc tgggctccca    18180
```

```
gctcctgcat cctgctgcaa acttgacatc ttccctcaag taacttgtag ttgtctcctg   18240
tctacttgcc caaaatataa ctcttaaact tttctctctg caagtttgtg cctctctccc   18300
tgtctgactt ccccatctaa ataaatggta gaccaccatc tactcctttg tgcaagccag   18360
aaatctagga atcatcctta aattccctgt tctgtcttat ctctgctttc attcaaagca   18420
tcagcaaatc ctgttggttc tacctctgaa gttttctcaa atactgttac ttgactcatc   18480 ctgactttg tttctgcttt atgttaggct aaatgccctg aaaactcttt tgtacaaaac   18540
acctagaaat actggataaa ctgggcttaa cagggaggcc cggtgtggtg gctcacgcct   18600
gtaatcccag aactttggga ggccaaggtg ggtggatcac ctgaggtcag gagttccaga   18660
ccagcctggc caatacgtag tgaaacccca cctctactaa aaaaaaaaaa aaaattagc   18720 tgggtgttgt ggtgcacacc tgtaggtggt gcatgcttga acttgggagg cggaggttgc   18780
agcgagctga gatcgcgcca ctgcacttca gcctgggtga cagagcagga ttctgtctct   18840
taaaaaaaaa aacaaaaaaa gaaaacagg aaaatcttca gaagcaaaaa ccaaacaatc   18900
tcaccaaaga aatgagaaga tggctgggcg cggtggctca cgcctgtaat cccagcactt   18960
tgggaggccg aggcgggcag atcacccgag atgggcagat caccgaggt caggaattcg   19020 agaccagcct ggccaatatg tgaaacccc gtctctgcta aaaatacaaa aattagccag   19080
gtgtggtggc aggcgcctgt aatcccagct actcaggagg ctgaggcagg agaatcgctt   19140
gaacctggga ggcggaggtt gcagtgagcc gagatcatgc cactgtactc tagcctggac   19200
gacagagcaa gactctgtct caaaaaaaaa aaaggctggg tgtggtggct catgcctata   19260
atcctagcac tttgggaggc caaggtgggc ggatcacttg aggccaggtg aacatggcga   19320
aaccccatct ctactaaaaa tactaaagtt agctgggcat ggtggtgggt gcctgtaatc   19380
ccagctactc gggaggcgag gcaggagaat cgcttgaacc aggaggtgga ggttacagtg   19440
aaccgagatc tcgccaccgc actctagtct gggcgacaga gcaagactcc gtctcaaaaa   19500
acaacaacaa aaaaccaaca catggccaaa gtgcagtgac ttacatctgt ataatcccaa   19560
tgttttggga ggctgaggca ggaggatcgc ttgagtccag gaatttgaga ccagcctggg   19620
caacatagac ctcatcacca aaaaaaaaat attttttaat tagctgggtt tggcagcatg   19680
tacctgtagt cctagctact caggaggctg aggtgggagg atcacttagg cccaggagtt   19740
tgatagttcg aggttatagt gagctatgat cctgccactg cactccagcc tgggccacag   19800
agtgagaccc tgtctcttag aaacaaaaca aaacaaaaaa aagaaactga attaaaaaca   19860
acaagaacaa aaatgctgct ttttgttatt gagttgtagc ccaagtttct tgagggtaaa   19920
gcattgaaaa gcaggcagta atagatttgc tgtttaaaga gatttacttg cagcactatt   19980
cacaatagca aagacatgga atcaacctaa atgcccatca gtgacaaatt ggataaagaa   20040
aatgtggtac atacactgtg gaatactatg cagccataaa aaacaacgag atcatgtttt   20100
tgtttgtttg tttgtttgtt tgttttgag atggagtctt gctctattgc ccaggctgga   20160
atgcaggtgg cacgatttca gctcactgca acctccgcct cccaggttca gcaattctc   20220 tgcctcagcc tcccgagtag ctgggattac aggtgccctc caccatgcct ggctaatttt   20280
tgtatttcta gtagagatgg ggtttcaccg tgttgggcag gctgttcttg aactcctgac   20340
ctcatgatcc tcccacctcg gcctcccaaa gtgccgggat tacgtgtgag ccaccgtgct   20400
cggctgagat catgttttg caggaacatg gatggagctg gaggctatta tccttagcaa   20460
agtaatgcag gaacagaaaa ccgaagacca cgtgttctca cttataagtg ggagctaaat   20520
gataaggact tgtgaacaca aagaaggaaa ccacagatac tggggtttac ttgagggtgg   20580
```

```
agagtgggag gagggagagg aacagaaaag ataactattg ggtattgggc ttaatactta  20640
atattttatc aaaataagct gtacaacaaa cccctctgac atgagtttac ctatataaca  20700
aacttgcacg tgtaaccccca aacctaaaat aaaagttaaa aaaaaaaaaa aaggctggtt  20760
gcattgggag gctgaggcag gcagagcact tgaggcaggg aattcgagac cagcttggct  20820
aacgtggaga aaccctgtct ctactaaaaa ttcaaaaatt agccaggtgt ggtggtgcat  20880
gcctgcagtc ccagctacca gggaggctga ggcaggagaa ttgcttgaac tcaggaggca  20940
gaggttgcag tgagctgaga ttgcaccact gcattccagc ctgggcgaca gggcgagacc  21000
ttgtctcaaa aaacaaaaca aaacaaaaca aaacctgtc actttgggaa tatctcaaac  21060
ctagtcatcc aagtggttgt acgattttag tgtctgcata tcaatattta gtgtgatcta  21120
ctttcttaga ttctcaaata ctgccaatgg cacatgtca tgaaataatg tcttttagag  21180
gacaagagag tgctaaagtc tcattattgc agtttaagaa aaacaattct gtaacagttt  21240
aactttatag gaaatgcctt ttgtttattt attttttttc ttttgaggct tagattttta  21300
ttttttatgtt tttagagatg gggtcttcct atgttaccca ggctggcctt gaattcctgg  21360
gctcaagtga tcttcctgct tcagcctcct gagtagctgg gactagacgt ccactactgc  21420
tcctggctgg aagtttagat tttaatttaa actcttctat tgggaaactt tgtatgtttg  21480
ctttaccact taacatttgc atgcattatt gtacctattg tctcctactt aaggaagggc  21540
agtttatgct gttatatgaa gtgaattaac ctcctatggt acttcagttt tctctatgct  21600
aaaagtgtgt tctagatttt tgaaaaactt acttaatttt cattcattta ttcaaatatt  21660
tgagcattct gtagttgctg gggaaatagc agtgaactga agaatgtctt tgttcttatg  21720
gggcttaagt tcctagttga tcatattgga aggagataca tgaaaaaaga aatatatgaa  21780
caatggaggg cgatgagtac tgtaaaggag aattcagcag gggagatgtt gctgttttag  21840
atagaggggt gtcaagagac attgtgcaga gacctgaacg aagtgaggga gcaagccatg  21900
gagatatcta gggaaagagc ctatcaggtg gagagaagag tcctagggca gaaacgggca  21960
aggtgtgttc caggagcaga gaggggacag ctgtgagcaa gggagagagtt gtagggaagg  22020
aggcaaagag agacatctgg ggcaaaatgg attgactggt gggccgtggt aggactttgg  22080
attttttcct gagtgggttt tgagcagggg aatgaaatga tctgactctg gtttttttt   22140
tttttggaga caaaatcttg ctctgttgcc gaggctgaag tgcagtggcg caatctcggc  22200
tcattgcaac atctacttcc tgggttcaag ctatgctcct gcctcagcct cccgagtagc  22260
taggattaca ggcttgggcc accatgccgg cgaatttctg ttttattttt tatttttat   22320
ttattttat gtttatgttt tttgagacgg agtctcgctg tgtcacccag gctggagtgc  22380
agtggcgcga tctcagctca ctgcaacctc tgcctccccg gttcaagcaa cttctcctgc  22440
ctcagcctcc cgagtagctg agattacagg cgcctgccac tacacctggc taatttttgt  22500
attttagta gaaacgggat ttcaccttgt tggccaggct ggtctcgaac tcctgacctt  22560
aatttatctg ctcgccttgg cctcccaaag tgctgggatg acaggtttga gccaccgtgc  22620
cagccaggac tcttattttg aaaggatctg taatgtggag aatagaaggt agagggacaa  22680
ggatgaaagc atccaggcca gttagcctag tccagctatc taggtaagag atgctggtgg  22740
cctggattaa ggctgcgtca gtgggaggtt gtgagaaagg ctcaccttcc tttttttttt  22800
tttttttttt ttttgagaca ggatcttact ctgtctccca ggctggagtg cagtggtgca  22860
atctcagctt actacaacct ccgcctcctg ggctcaagtg ataccccccac ctcagcctcc  22920
```

```
caagtagctg ggatcacagg cttgcgccac tatatccggc taattttttgt atatttcgta    22980
gagacagggt tttgccatgt tgcctaggct ggtctcaaac tcctgagctc aagtgatcca    23040
cccgcctcag cctcctaaag tgctgggatt ataggcctga gccattgtgc ccggtcactt    23100
ccagattttg aagacagagc aacaggatt tgttaatgga ttaggtgtgg caggaggagg     23160
gggaggaaga gagagagaga ctggagttga agttaaggct catttcaagg tttttagcct    23220
caacatgtgc aggaatggag ttgtcacttg ctagaatggg ggagactgga ggagaagccg    23280
gctgggagag gttttttaatg aaggggttgg ctttggatac attaagtttg acatgcattt   23340
tagacatcca ggtggagata ttgaagaggc agttggctat aagtgtctga tgttcatatt    23400
agcggatggg gctagagaca taaatttgag aattgtcagt gtataaacgt tgttttgaaa    23460
gaaagtgggg ctgaataatt tagaaaggag tgcatagaga aaataagttt actattaaaa    23520
tagctttaac aggccgggca cggtggctca tgcctgtaat cccagcactt tgggaggctg    23580
gggtgggcag atcaaaaggt caggagtttg agaccagcct ggccaatatg gtgaaaccct    23640
gtctctactg aaaatacaaa aattagccag gcgttgtacc gggcacctgt agtcccagct    23700
acttgggagg ttgaggcagg agaatcactt caacccggga ggtggaggtt gcagtgagcc    23760
aagatcacgc cactgcactc catcctgggc aacagagcaa gactccgtct caaaaaaaaa    23820
aacaaaaaaa aacaaaaaaa aaaaactttta acagcaaagc ctcttccttt aaaattatga   23880
attttttct tatggaagtt ggactctttc attattaagt ctacattcaa tcactatgtt     23940
agtaaaaatg ttgttctagt tgccgaatgc aataaaccag ctcagactta gtggcctaaa    24000
gcagcaatca tttgactatg ttcgaagatg ccgtgggcag gaatttagat aacagcaggg    24060
atggcttgtc tttgctctgc gatgtctgag gtctcactga gaaaactcaa gcggctgggg    24120
gtaataatca tctggaattt tctttactcc tgtatctgat gtctgggctg cgatgactca    24180
aaggctgatt tcagctgaga ctgtagacca cgtgcctact tgtggcctcc ccttttgcct    24240
tgggtttctc acagaatgtg gctggttctg gagaatgaga cttccaatga aatcaggtgg    24300
aaatgacatc tcgccgcttt cagcatgctc tattggttgg aacagttatg gacttagcta    24360
gattcaaagg aagggaacaa agaccccctc ctctcagaga gtggggcata atgagagaat    24420
ttagggccat gttatccaac caccacaaat gccttctgaa tttgaggttc tgcctcaaaa    24480
gttcatagtt cctttgactg aaggacttct atatatccaa gcatcgtcag ccccaggtat    24540
attgttccat gtaagtgacc aggactacct tagtatttcg tatagggaaa gtgacctgaa    24600
taaatttgag aaaagaatct tccttctctc cagtaagcac tgaggtaagc attgagccat    24660
attataggtt tatgactttg agactcagaa atttaaattc ttggccaggc gcagtggctc    24720
acgcctgtaa ccccaacact tgggaggcc aaggcaggca gatcacttga ggtcaggagt     24780
ttgagaccaa cctggccaaa atggtgaaac tccatctcta cgaaaaatac aaaaattagc    24840
caggtgtggt ggcgggcacc tgtaatccca gctactggg aggctgaggt aagagaatgg     24900
cttaagttct ctttatctgc tttatttcag ttgcctctct tagatgaata ttaatgactt    24960
acatagcatt ttagatcagt ggatgttttt gtgattcttt tatttgagct ttggccaaag    25020
ataacagtac ccacaggttt tttccagcta ctcgctcttc tcccttcagt ggccctcgag    25080
cctggaaaat ctgacatgac aatgtgcttg ctcaacctac cactgttttt cttttgaaaa    25140
gtttggcagc ctgttctga ctcctatgaa ggtgaattcc tcagcattca cagtttatta     25200
gaaaatact ttgcttctct ccaaactcga aattcaagat aaccaaacct atatataggc     25260
tgatctttca ggatgcagtt gtcatgttga tgccatgctt ttcagtatcg tggccatcat    25320
```

```
ctgttcagta ggggaggtgt acttctgtaa tgggaggtgg tggttatgtg tgtgtgcaag    25380
tgtttatttg gtgtcttaag ttagcctgtg ggaagttcta aatcaggatg gtacgtggtt    25440
gccagcagag agctgctcct caagtgaagg aggtagaatc aaagccaata ggaaagagcc    25500
tcagatgctt atatatgtac cgtggggatt cagagtgaaa gcagtcattg gactaggggt    25560
ggggttaggg agagcctgtc tgacagacac aagaaaggga tggataacgc cacccagaga    25620
aaaaagcatt ttaggcaaga acaaatatga aaaaggaaca aagtctgtgg gtgggggca    25680 aggaggagat aagttgactt gaaggaagac aacacttatg aaagtcacct ggaggctggg    25740
tgccatggct catgcctata atcgcagcac tttgggaggc cgaggtagga ggacaacttg    25800
agcccaggag ttcgagacca tcctgggcaa catggtgaga ctgagtctct accaaaaaaa    25860 aaaaaaaag aaaattatcc agacatggtg gcatgtgcct gtaatcccag ttactcagga    25920
ggctgaggtg ggagggttgc ttgagcccag gaggttgagg ctgcagtgag ctgtgatcgt    25980
attattgcac tccagcctgg gtaacagagc aagaccctgt ctcaaaaaat gaaagtcatc    26040
tgtaggctgg agagaggaac tggaagggc taaagttggc tgagtagtta cagagcctga    26100
gataagggta aagattttgc attggacaat gagatgttag tgtgtgtttt tgagctgggg    26160
agtgctgtga ttttactctt attgaagaat cactgaagga ttattcttga atcagtgatt    26220
cttgatcatt cttgaatttt tcaaacagca aaactggaag agttggccta ttcctcagaa    26280
tattttctaa ttgggcgcag tgtcctcact tgggagaacc tggctacaca ctttagttgt    26340
aattcactcc agtcgttcat tcattcaata cctatttttt cagcacctat tatgagccag    26400
acactatgct ggatgccagg gttcagggta ggacacgcta gtgagcaaaa gccaagactc    26460
ttcttgtctt catggggctt tcagtccagc atagtggtta tgagtccaag ttaatggagt    26520
cacagtactt gggtgcaagt catggtgatg gtgatagaag gaaggcatgt gtgagggcca    26580
gtggcaggca ggagcctggt gttttgagg acctgaagaa ggagcagagt gagtgccagg    26640
aacttagcca ccagctggta ccagccatac gagaggggca gagccagcca ggatgtcggt    26700
catgctagta atgagtacaa acacttacat gctgcacgct attgggctcc tgagtgctac    26760
gtgttcatta gctcgatgaa tttgtacagc aaccctgtga ggtaagcact gttctctccc    26820
ctttctatag atgaggaaat taaggcacaa agaggataaa taactggcac cagctacacg    26880
ctaagtgatc gaagtggtgg aaccaggatt caaatccatg ctattctgcc ttaagataac    26940
aaatcttgtt ttttagccta agaacagagc agtcatcagg agggttttaa gtagggtgt    27000 ggcaagatca agtttgtgtc ttgaaaaggt ctctctaccc acagtgtgga aaatggcctg    27060
gaggcaagca cacagatgtt gggagacagt taacagctct tgccatggcc ccctatgcat    27120
tttggctctg atgtttctgc ctgatttttc tcttgcctct gcctcttttc ctgagggat    27180 ggcaggtttt accattcagc tggagtacaa accctgaacc cttttggtt aaatatctac    27240 ttgcttttcc tacagtatta ttttgagttg ctgtggctgt aatgtcttga gggaatcgag    27300
cttgacagta atttatagaa caaacagttt ttagagactg tgtggcccaa ttgccctctc    27360
aatgttggca ctcctgccat gacatttacc atgctgagca tgtgaccgcc atctgaatac    27420
caaatgccac aggaacctgg gaggttgtca cttactcctc cctttctctg agtcacctt    27480 gcccttcagt cagtcaccaa gtcccatcac atgtagctct gtaatgtcac agaagatgga    27540
tgtctgcctc aaaacactta caatgctgct acctaaattg ggcagccacg acctcccacc    27600
aggattattg cagcctgagg gatctttttg aaatgtaaat caaactatca cttgtctgtt    27660
```

```
taaagctttt caaagactta ccccattgcc cttggaagaa agtgcagata tcttgacagg   27720
agagccttct ccagcctcct cttctgccgt ggtctccttg tacagtctct acagtgtact   27780
gcttcattag aaccctggag attattattt gctagttctg ggctaagaac tggcacctgg   27840
ctttgtagag ctcctcagga gattctgagg cgtattcaga gttgagccct gatctctgct   27900
ctgatttcga ggttctcgtt atatttatta atgatcacga aaaaatttat tattattctt   27960
tggcctcact ttagcatcat ctgaggaatt tttttttttt tttgacagag ttttgctctt   28020
gttgcccagg ctggagtgca atggcgtgat ctcagctcac tgcaacctcc gcctcccggg   28080
ttcaagagat tctcctgcct cagcctccca gtagctgaa attacaggca tccaccacca   28140
tgcctgctaa tgttttttgta tttttttagta gaggtgggct ttcacagtgt tggtcaggct   28200
ggttttgaac tcctgacgtc agctgatcca cccacctagg cccccagag tgctgggatt   28260 acaggtgtga gccaccgtgc ccagccgtag cttttcgaaat ttgaaacctg gtcccactgt   28320
cagaggttcc aatttggcac tggtttggtt cccaggcatc tttcttgctg tatatatttt   28380
ttagtgtcag ccagggtgga gacctctgta ttacttcatg gggaagaatt tgggagaaga   28440
tgttgtgagg agacaggttc tagtcctaga gtgatttatc ctttctcgta cagatttcca   28500
ggtatttgag gggccactct tctgtaattc atgttttttct ctcctaacct cactcctgtt   28560
gcctgcatct tcttgctgag caaaatattc aaggtcttca actcctcaca ccctggttgt   28620 ccctcccttgg atgtgtttgg ttgttttagt gttccatttc aatttgata cacagaatta   28680 gaatagcatc cagatgtggg tctgttacag ctagactact agatccttca aaatccaagt   28740
actagtatgt ctattaaaat accataagat cacattggct agttacaatg gttggtttgt   28800
gggttactta aaatcaact aaaattcttt tttttttttt gagatggagt tttgctcttg   28860
ttgcctaggc tggaatgcaa tgacacaatc ttggctcact gccacctctg cctcccaggt   28920
tcaagcaatt cccctgcctt agcctcctga gtagctggga ttacaggcat gtgccaccat   28980
ggccagctaa ttctgtattt ttagtagaga tgaggttttt ccatgttggt caggctggtc   29040
tcgaactccc gacctcaggt gatccacctg cctcagcctc ccaaagtgct gggattacag   29100
gcgtgagcca ctgagcctgg ccaaaattcc cactttctaa tactcctgta gtagctgggt   29160
acggtgggtc acatctgtaa tcccagcact tttggaggct gaggctggag gatcgcttga   29220
gcctaggagt tcgagaccag cctgggcaag atggccagac gccatctcta atttaaaaaa   29280
aagaaaaaac aagactccta tagtggtgaa gaacagacat tccgaaaaca gactgtgcgt   29340
tatgattcca gctccatgcc tttactacct gtgttgtgac tttggataaa tcacttaaaa   29400 atctttttttt tttttttttt tttttgagac ggagtcttgc tctgccgccc aggctggagt   29460
gcagtggcgc gatctcggct cactgcaagc tctgcctccc aggttcacac cattctcctg   29520
cctcagcctc ccaagtagct gggactgcag gtgcccgcca ctacacctgg ctaatttttt   29580
gtatttttag tagagacggg gtttcaccgt gttagccagg atggtctcga tctcctgtcc   29640
tcgtgatcca cccgcctcag cctctcaaag tgttgggatt acaggcgtga gccaccgcac   29700
ccggccaaat cacttaaaat tctgtgcctc agtttctcct ctgtaaagtg ggataaaaat   29760
agtacctatc tgatagggtt gttacaatta tgaaatgagc aaataagtat gtcaagtgtt   29820
taaaacagcg cctggcttct tgtaaaaagt gctatataaa tcatagctat aatcattact   29880
tatttcgact gctctttaac caaggttctt attttttcatc ttttttcttt gttttgaata   29940
tcacttagtg ttttcacctt ttactctttt taggacctag agccatccta ggtgaaatac   30000
gtatggagat atttgatcag gtcaccaccc agctctcctg acctcccttc tctccttaaa   30060
```

```
ttaacatgcc aaatcacagc atcactgact ccttccctcc cgatatgata agagtgtgca    30120
ttgaaatgca tgtattttac ttagcaggga aagctgatta gtgattatca cacttaaccc    30180
ctagtgaatc tgatggatta acctgctttc caggacacta aggaaatggg tttaagataa    30240
gaaatatctg gctgggtgcg gtggcttac gcctgtaatc ccagcacttt gggaggccga     30300
ggtgggcaga tcacgaggtc aggtgattga gatcatcctg gctaacacga tgaaaccccc    30360
tctttactaa aaatacaaaa aattagccgg gtgtggtggc gggcgcctgg agtcccagct    30420
actcgggagg ctgaggcaag agaatggtgt gaacccagga ggcagagctt gcagtgagct    30480
gagattgtgc ccaccgcatt ccagcctggg caacagagtg agactacatc tcaaaaaaaa    30540
aaaaaaaaaa agtaagaaat gtccatgaaa gggagaccct ggggggaaagg aacaataact    30600 gcagctctga ggatctggca ccagcagcac cagcacagag ggatgctgta caaccattat    30660
tgattttaac tttacaacag ttcttcaaag agagagagt tccctgttttt actgaagaga     30720 aagcccattt ggtagtgaaa taccattccc aaagacaaat agctaataaa tgtcaggcag    30780
ggttttgcac ccaggcccat ccagctcccg tctctactgt cctttccccc acaccacact    30840
gatacagagt aatgtgtctg gttggggaag tggaagtgtt cccaagtggg gaggtcatct    30900
gatgcacaaa tttggtctgt tttgtgggtt ttcttgtttt agttttagtt tttgtagagc    30960
tcagacctgt tcttaggcag ctttaacaat caactgtgca ctcagtaatt gacaaatcat    31020
gtttgttact tttaatttag agggaattag gtttgttaag ctcttgctcc ttctttagag    31080
atggggtcta gctctgtcac ccaggctgga gcgcagtggt atgatcacag ctcactgcag    31140
tctcaatctg ctcaagtgat cctcctgcct cagcctccat gggactacaa gcatgggcca    31200
ccatgctagg ctaattttaa aaaaatttt ttgtagaggc aaggtctcac ggtgttgccc     31260
aggctggtct tgaactcctg agctcaagca atccctcttc caccttggcc tctcaaagtg    31320
ctagaattat aggcatgagc caccatgcct ggcctttact tctttcatat attcaaattt    31380
tgtcatatta gtagggaact ataactcaag ttttcttata gattgatgtt cattttaca     31440 agcttgatcg tcattggttt ttaattttaa agcaaatcct gttatatgta attgaacatt    31500
acagtaatta tagtaatttg tttcagattg ggcactcaag tgttaatatt ttgtctcttt    31560
aggaaatcaa aactagattt atatatagac ttcttattgc aagtatctag tcttaaatct    31620 tacaaggta ctatttggac ttaaaactat gaaattgtgt gcttactata aagtgtact     31680 tattttgagt tatgttttaa acttgaaatt ccattcttaa tgtctagagt aattatgaat    31740
ggttaaatta tgaatgactc taatagttta aagctacagt atttatttat ttatttattt    31800
aatttatttt ttgagatgga gtttcgctct tgtcgcccag gctggagtgt agtggcacca    31860
tcttggttca ctgcaacctc tgcctcgcgg gttcaagtga ttctcctgcc tcagcctccc    31920
aagtggctgg gattacaggt gtatttcacc atgcctggct aatttttgta ttttttagtag    31980 agacaggctt ttgccatgtt agcctggctg gtctcgaact cctgacctca ggtgacctac    32040
cctcctcagc ctcccaagga ttacaagcat gagccaccac acctggccta cagtatttta    32100
atgtggactc tctgtcatcc attatgctgt ttatcctgtg gtgaaaattt tatgaagatt    32160
gaatgttttt ctctagcgtg aattgctttc tcttactttt ctcattttt tccttcctaa      32220 tctacttgca gatacttcag attatttta gaacgtggta tggtgagaac aaataaattg    32280
gggtttccaa atcttaataa attatgtggc cctcagtggg attagcaggg ttgtattgaa    32340
aacaccaata gaaacaaaat agttcttta tgcgctttaa ataaaaattt cttttcaggc    32400
```

```
caggcgcagt ggctcacacc tgtaatccca gcaccctggg aggctgaggc aggcagatca    32460
cctcaggtca ggagtttaag acaagcctgg ccaacatggt gaagcgccgt ctctactaaa    32520
aatacaaaaa ttagccgggt atgatggcgc atgcctgtaa tcccagctac tccagaggct    32580
gaggcatgag aatcacttga actcaggaga tggaggttgc agtgagctga tggtgccca    32640 ctgcactcta gcctgggcaa cagagtgaga ttctgtctca acaacaaca acaacaataa    32700 caaaacatct cttttcaggc caggtactgt ggctcacgcc tgtaatccca gcactttggg    32760
aggccaaaac aggagggtcg cttgagacca ggagtttgag accagcttgg gcagctggtc    32820
tctatttgaa caaacaaaca aacaaacaca atactctttt catagaaaaa tgtttactac    32880
acaataaact ttaaaagaat atgcagctgt attaatgcta tgactccaat gtaaaaaaaa    32940
aaaaatatat atatatatat acacacacac aaacacattc tgaaatagat ttaaaggaat    33000
tacatcaaca tgtcaatttt tatttttttcg gagacagggt ctcgctgtgt cacccaagct    33060
ggagtacagt ggtgcaatca cagctcactg cagccttgac ttcctggcct caagtgatcc    33120
tcccccctca gcctcccaaa gtgctgggt cacagaccac cacacctggc aacatgtcag    33180
tttttgttct gcatagtggg atggtgggat atggatgttt ttatctttta tttctttttt    33240 tatattttc taaattttcc acattgaaca ttatttata atcttcaaa catatctctt    33300 aaaaggactg gttcctatag aattcagtgc aagaaatctt ctgtgtttct ttatactttg    33360
gttgccttga tcactgggcc tttcctgaca gcaaagaaga ggttagtgta ggcagcagat    33420
aaaacacagg tatgctctat ttaaaatgca tgtatttata ataaagtat aggtggtacc    33480 caaaggaaaa tgtcatgaca cattgcaaag tggaacagaa gttatcttta gatcactttc    33540
tgttctggat tattgtatga gcctgatttt cgtctctctt tccgccttcc ctcaccctcg    33600
ttgtaaatcc actagtgcat ggatgtgaag tacaagtctt aactttaaaa agttttatga    33660
agctgtgtag taaatcccctt ttgtaagtgg tcttgactgc gtttctcaat atatcttttg    33720
gtttcattag attcaagtat ataaatgaga actgtaactt tggacagact ttttcagtca    33780
tctttacggt aataagttcc caattagaca atagttattt gttttatgac ttgctgttgg    33840
taggttatcc ccaagggact gagaaaattcc tgttttgaaa agtccaaaaa gtctttgatg    33900
acttgctgtt tcatttttttt cttttctctt cagttataga aaacaggatt acccccacct    33960
tgcctttgta cagtgcatct actatctgct gacttaaccct gagtaaatgc tttgaattga    34020
gccccatata atgtcctaag gcagcctata tggagtaatg aattgtcttc tctcttatgc    34080
acccagagtg gtagttggca ctcaagttgt tcctcagata actttgtgtg ttctggggct    34140
caatgaagta gttattaagt cacaggcttg gggagaacat tcatcctatg gcattgaatg    34200
aagtgttgcc caattctaga atgtctaata aaattttttt aaaaacccac aggcttagaa    34260
ttattccgta gatatgaagt aatgtagtta gaacttagtg gagttcttta gattaacttg    34320
taatttgaaa aaccaaaatt gaaattgtga aataacatgg gctctttgag gtcttttcca    34380
gtaaaacagt tacagtaaag ctgcttggca gtgattttcc tagacacttt ggctagtcat    34440
ctcctgtgac tgctgttaat taaatatggt ttgtagctaa gcagcctgta aggagaagac    34500
tatggaagta tttgcatatt ctctccttga aaatactacc tggtctttgg ctttaagtta    34560
tacttttatt ttcccctgta gaataactat taaagtatta cctatggtga ttagactaag    34620
aagtaaaaca tgaaatcagt cattgttggt gccctggtgc cttctttttt ttttttttga    34680
gacagagtct cactctgttg cccaggctgg agtgcaatgg cacgatcttg gctcactgca    34740
acctctgcct cccaggttca agcgattctc ctgcctcagc ctcccaagta gctgagacta    34800
```

```
caggcgccca ccaccacgcc tggctaattt ttgaattttt agtagagaca gggtttcact    34860
atattggcta ggctggtctc aaactcctga ccttgtgatc cgcccacctc agcctcccaa    34920
agtgctggga ttataggtgt tagccactgt gcccagcctg gtgctttaat tttatggaaa    34980
aaactactag ctggtttctg ttttaagaaa taacacaggc cgggtgccat gacttgcgct    35040
tgtactccca gcagtttggg aggccgaggc gggcggatca cgaggtcagg agtttgagac    35100
cagcctggcc aacatagtga aacccgtct ctactaaaaa tacaaaaatt agccgggcgt    35160
ggtggggcat gcctgtagtc ccagctactc gggaggctga ggcaggagaa tcgcttgaac    35220
ctgggaggtg gaggctgcag tgagccaaga tcgccccact gcacaccagc ccgggtgaca    35280
gtatttcatc tcaaaaaaaa aaaaaaaaa aagaacacaa ttattgtact acttactagc    35340
cctcctctgt ccccagctaa aaataagaac agcaacaacc aaaaaatcct tagttatgta    35400
ctggaaatga attagataat tttcaataac ttacacgttt ttaggatatg ttagtttgaa    35460
aatgcaaata ttcatgcatg accccagtgt taatctatga tggagcaggt atagtgggat    35520
gctgtttcat gatttaattt ggaccttcag ggagtagact gtgatgcctc tgcatttgta    35580
tccaagacaa ataattaaat agtctatttt ggctgggca tgatgcctca tgcctgcagt    35640
cccagcactt tgggaggctg aggtgggagg atcgcttgag gccaggagtt caagatcagt    35700
ctgggcaaca aaatgagacc ttgtctctac aaaaactaca aaaaattagc tgaacattgt    35760
ggcttgtgcc cctagtccca gctactcagg tccctgagtt aggaggattg cttgagccca    35820
ggagttggag gttacagtga tctatatttg ccactgcact ccagcctggg tgacagagag    35880
agaccctgtc tcaaaaaata aagtctgttt ttaaaattaa ttttaaacac tggagtttat    35940
tacaaaaagc agttggttct ttttttaaat catttttttt taggagaacc accgcttttt    36000
ggctacattg tctagagtag cagtgttcaa taaaaataag atccaagtca catatgtaat    36060
gttaagtttt cttttagttt cttttttcttt tcttttcttt tctcttcttt ctttctttct    36120
ttctttttttt ttttttttgat atgcagtctc actctgttgc ccaggctgga gtgcagtggc    36180
acgatctcgg cccactgcaa cctccgcctc ccgggttcaa gcaattctcc tgcctcagcc    36240
tcccgagtag ctgggactac aggcatgtgc caccataccc agctaatttt tgtattttta    36300
gtagagatgg agctttgcca tgttggccag tctggtctca aactcctgac ctcgggtgat    36360
ccacatgctt tggcctccct aagtgctggg attacaggca tgagccacca tgccctacca    36420
atgttaagtt ttctagtagc catattaaaa gaagtaaaaa gaaatgggtg aagttaattt    36480
taataatata ttttatttaa cccaatatat ctaaatatat atcatttcaa catgaacaag    36540
atactttaca ttcttttgtt tttcactaag tcctcaaaat ccagtgtgta tttatattg    36600
acagcatagt tcagtttgaa gcagccacat ttcaagtgct cagtagccac atgtggctag    36660
tgactccata ctggactgtg taggtttaga gtttcagtaa atttgtatgc aatagaatct    36720
acataaattg gcatattatg cagatttctt tgtatgcaca tcagttcttg catagcataa    36780
gtcaggtcat gatgctttta gtctatgagg cagatttttt tttttttttt tttgagacag    36840
agtctcactt ggtcacccag gctggagtgt agatgcacaa tcttggctca ctgcaacctc    36900
catgtgaggc agattttaac ttggccctaa tgcaaatatt gtaagagaga tctaatggcc    36960
tttgatttct tacagagggc aatcaataca tgccatggtt acaatgcttc agcatatagt    37020
atgcacgtca gccactgctt ttactctggc tagtgcttag tgtacctgta ccactgccca    37080
ggcagcattt gtcctgtggc aggtgaatct tagggtggaa ggtggcaagt aacattgctt    37140
```

```
tttttttgaga gggagtcttg ctgtattgcc caggctggag tgcagtggtg cgatctcggc    37200
tcactacaac ctccacctcc cgggttcaag tgattctcct gcctcagcct cctgagtagc    37260
tgggattaca cacggccacc accatgctcg gctaattttt gtattttttag tagagacggg    37320 gtttcactat gttggccagg ctggtctcga actcctgacc tcgtgatcca cccgcctcgg    37380
cctcccaaag ttctgggatt acaggtgtga gccaccgtgc ccagcctaca ttttttaaatt   37440 aattaattat aagcaggatc tcactgtgtt ggccagactg gtcttgaact gataagagtt    37500
caagaccagc ctaggcaaca tggtaaaacc ctgtctacta aaaatacaa aaaaaaaat     37560 tagctgggca tggtggtgcg tgcctataat cccagctact tgggaggctg aggcaggaaa    37620
atcgcttgaa cccgggagac tgaagttgca gtgaggtgag attgcaccac tgcactccag    37680
cctaggcgat tccatctcaa aaacaataac aacaaaataa cattgttgga atatttagtt    37740
aatttataga agcgtattgg cctaattggg gcaaatacct tattctgaca ttctctctat    37800
ttgctttact gagcttttc accagtggaa tttaagccct tgatacatga ggagggaaaa    37860
taccttggag ctgtgctgca catgtaaagt acacaggaga tttagaaaac ttcgtagcaa    37920 aaaaagagt gtaaagtatc tcattaatag ttttttgtggg ctggacacgg tggctcaagc    37980
ctatactctt ggcacattgg gaggctgaga tgcatgagtc taggagtttg agaccagcct    38040
gggcaacaca gtaggacccc gtctctacaa aaataatcag ccagatgtgg tgcgcatctg    38100
tagtcccagt tacttgagag gctgaggtgg gaggatcgtt tgagctggga agttgaggct    38160
acagtgagct gtgattgaac cactgcactc cagcctgggt gacagagtgc ctgtctccaa    38220 aaaataata aataaataat aatatgtttt gtatgttcat atgttgcaat aacatttgg    38280 atatattaaa tgaaataaaa tacattaaaa ttaatttcac ctgtttctt tcttttcttt    38340 tttttttttt ttttttgagat ggagtctcgc tatgtcatca ggctggagtg cagtggcacg    38400
atctcggctc actgcaacct cctcctcctg ggttcaagcg attcttctgc ctcagcctcc    38460
ctagtagctg ggattaaagg catgtgccac cacacccagc taatttttgt attttttagta   38520 gagacggggt ttcaccatat tggccaggat ggtctcgatc tcctgacctc atgatccgcc    38580
tgccttggcc tcccaaagtt ctgggattac aggcgtgagc cactgcaccc agcctctttt   38640 aacttttttaa gtatggctac cagaaaattt aaaatgcatg tgtggcctgt attctatttc    38700
tgttggatgc tgctgcctta gattattaat tattcaatgt aaagactgct gggaggtact    38760
acctgcactt ccctgaatat atgcttgaga gctccaccag ccgtcttcac agtagcaaga    38820
ggggtattct gagtctgtcc cccaaagagg gaggagaag tgcagccctc tcaggttctg    38880
tcagaaaacc tgatcccagg ccaggcgtgg tagcttacgc ctgtaatccc agcactttgg    38940
gaggttgagg caggaggatt gcttaagccc aggagttcga gaccagcctg gcaacacag    39000 tgaagaccct atctctacaa aaatttttt aaaaaaatta gccaggtgca gcaatgctgc    39060
ctgtactccc agctgcttgg gaggctgagg taggaggatt gcctgagccc aggagttaga    39120
ggttgcagga gttagaggtt ccacgatcgc acctttcatt ccgttacatt tgctgccttg    39180
agaacagaag acctgctggt tttgttgcca gtttgctcag tcatttttat gaaaaagcca    39240
gtgctaacta ggtgcttctt cgtgccttct ctgagaatca agaactctag tatgtttgcg    39300
tgtgttcagt ctctcattaa atgttctcac tatcccagag aaccatctca ttggaccttg    39360
gtctgtacat accttcatct ttggctctga cttgtaatta ttttttagaac ttctcttttt   39420 tttttttttgg agacagagtt ttgctctagt tgccagactg gaatgcagtg gcacgatctc    39480
agctcacctc aacctctgcc ttccaggttc aagcaattct cctgcctcaa cctcttgagt    39540
```

```
agctgtaatt acaggcatgt gccaccacgc ctggctaatt ttgtgttttt agtagagaca   39600
gggtttctcc aagttggtca ggctggtctc aaactcccga cctcaggtga tctgcccgcc   39660
ttggcctccc aaagtgctgg gattacaggc gtaagccact gcgcctggcc taattttaga   39720
acttgttaaa acaacttggc ctctattgat atttccatga cccatgctat tcagaaagag   39780
gattacaggt aattagctgg ctgggtttct cataccagag catttcactg ggatgttcct   39840
gaacctggga caacttttat gcctggcatt tttctttcct tctctgttgt cccagactaa   39900 gcaatttta aaatagttat tatttgttga gtaggagaat ctcaggcaga tcttcctgga   39960
tcctcattta tacttttaaa cctgtagtct tggaattagt gctctgtccc caaccccaa   40020 acatccaatt tctacatttt ggctacagta caggtttact gtgtataact aaaagggctg   40080
tggaggagaa agaaaggaac cgacatttgt tgggcatctg ttatgtgcca tgcactgagc   40140
tggatgctgt aggaatatct caatacctct gaggagtggg aattattatc tctattttat   40200
agacaaggga atagaaatct gggagttaag taatttttta atttcacaca cttctggtag   40260
ataatggatt ctagaacctg gcataatagc cacttgtcat cccagtgtaa aagagatgtg   40320
tggccagatg gggtggctca catatgtaat cccagcactt tgggaagccg aggcaggagg   40380
atgacttgag cccaggagtt caagaccagc ctgggcatgt tttgtttgtc tcacgaaaca   40440
ttttttaaaa aatgagtgtg gcatggtgtt gtgtgcctat agtcccagct cctcgggagg   40500
ctgaggtggg aggatctctt gagcccatga tcatgccatt gcactctagc ctgggccaca   40560
gagcaagact ctgtcttcaa aaaataataa aaaggagctg tgattatccc aaggtgggga   40620
ttgtgaatgt gtttgtattg ttctaaactg ggagaaacag gctgggtgtg ttggcttatg   40680
cctgtaatct cagcactttg ggaggccaag gtgggaggat cacttgagtc caggagttca   40740
aggccaccct gggcaacagg caaaaaatag agacccatc tctattttt aaaaataaaa   40800 taaactggga gaagaagca gggtcctccc cagagcatct ttatccctag tcacagacct   40860
gacacctgtg ttgggcaatg gctacttcta gattgtttac ccctactggg acttgtggtg   40920
aacatatgca cactttggtt tacagttggg acccctgatt ttagcaggat ggcccaatgg   40980
aatcagctac agcagcttga cacacggtac ctggagcagc tccatcagct ctacagtgac   41040
agcttcccaa tggagctgcg gcagtttctg gccccttgga ttgagagtca agattggtaa   41100
gtccttctta agtgactctc caaattgtta ggtttcagtt tgagtcaaga gacatgaact   41160
cttaatgtca tgccttgctg ttccattaaa aaatgtatgg gtacaggtga tggggaaaat   41220
gagatcagga gataaagggg cacccttgg tcttgtaaag ccttttttat cttagaaggg   41280
catgtgggca actgtctttg acacattgaa accgcctgta tggtggtgga tgtcttgaag   41340
gttgatttgg acctcattta cttgggcaga tcctctatat attctgataa tccagtgatg   41400
tggtagacat atttttctc tgaatgtgaa ttctgtcata gctagaactt ggggttgata   41460
cttgtaattc cccctttagtt aaaggaagga gccacagggg tgtattagtc tgttctcaat   41520
ttgctataaa gaaatacctg agactgggta atttataaga aaagaggttt aatcggctca   41580
tagttctgca ggctatatag gaagcatagc agcatctgct gctggggagg cctcagcaag   41640
cttccaatca tggcggaagg cagagaggga gcaggcaggt cacatggcca cagcaagagc   41700
aagagagcaa gggggaggtg ccacacactt ttaaactatc agatctcaca agaactcact   41760
gtctcgagga cagtatcaac agggatggta ttaaaccatt catgagaaac ccaccccat   41820 gatccagtca ccttccacca ggccccacct caaacagtgg gggttacatt tcagtatgag   41880
```

```
atttgggcag ggatgtagat ccaaactaga tcacaggata agggaagtag attccattca    41940
tagagcagat aatggcacag atgtccagca actattttct tcactttaat atgctcaggc    42000
tcactactga ttttggttta attcaggcca gtgttaatat gacctggttt ttccagaatg    42060
catactctga tttggtgaag ggccaggagg tgattcacag atgttggaga taggccatcc    42120
cagcctggga ttacttattt gtactaataa atctgaccag agttaattga gggtttaaag    42180
caaaacagca tatctgtcta ctttgctcaa atattttaca aatacaacag attatgagag    42240
tgggtaataa tatctggaat aattgttttt ttgttttgtg gttttttttt tttttttttt    42300
gagatggagt ctggctgtag cccaggctgg agtgcagtgg tacagtctcg gctcactgca    42360
cctctgcctc ttggattcaa gcgattctcc cgcctcagcc tcccgagtag ctgggattac    42420
aggtgcccac caccacacct ggctaatttt ttatttttag tagagacagc gtttcaccat    42480
gttggccagg ttggtctgga actcctgacc tcaggtgatc cgcctgcctc agcctcccaa    42540
agtgctggga ttacaggcat gagccaccat gcctggcctg gaataattgt taataattat    42600
tacattgatg gcattttatt gctgagcaag aagaatctaa catgatgaat gggttatagc    42660
atcaggtttg ctttgttttt ttgttttttt cctctttctt gatggtgatt tctgtgtttg    42720
tgtgtatgcg tcggcttcag agccattctt tatcattctt cctttcccta gggcatatgc    42780
ggccagcaaa gaatcacatg ccactttggt gtttcataat ctcctgggag agattgacca    42840
gcagtatagc cgcttcctgc aagagtcgaa tgttctctat cagcacaatc tacgaagaat    42900
caagcagttt cttcaggtat gatgagaaac tgaggacaag gagaaacagg acccgcagag    42960
tcgggtgtta gtgttctttc ctggaagcat ctcttttctc atttggctaa gtaacgagaa    43020
tctatcttgt atttcaatc acaggagaag taattagccc tttctcaaag ctctgtatac    43080
ttacccgtga gcatcattac ctgagaatca cttctcttgt cacagttgaa gtaataaagt    43140
gattgttatg ttaatcatac atgttagcat gttaacgcgg tccactgata ggaagatgac    43200
tctcactgtt acatgttaaa tgtttgacca taatgggata cttcttgact aagtcagtag    43260
cttccctgca agaccaggat agtatactgt gtaaagactc agacaaggcc aggcatggtg    43320
gctcacgcct gtaatcccaa caccttagga ggttgaggtg ggaggattgc ttgagcctgg    43380
gagttttgag accagcttgg gcaacataac aagacaccat ctctacagaa attttttta    43440
aaaactagct gattgtggtg gcatgcacct gtagtcccag ctactcagaa ggctgaggtg    43500
agaaaattgt ttgagcctgg gaggtcgaag ctgcaataag ccgtgattgc gccactgcac    43560
tccagcctgg cggacagagt gagagccagt ctcaaaaaaa aaaaaaaaag actcaggcta    43620
atgtgccttc tgttacagaa atagtaacga cctcccttc gcccccgcc gacagagagc    43680
cttcacccag gctctgaagc ctttgttccg ttgtttccta gaataaatgc tttccttgat    43740
gaatacatta gttttaaggt gccacagttc agtccacatc tccatggtct gctgctgatt    43800
tttattctct ttctctccta cttatagagc aggtatcttg agaagccaat ggagattgcc    43860
cggattgtgg cccggtgcct gtgggaagaa tcacgccttc tacagactgc agccactgcg    43920
gcccaggtga gacctgagac aaaacaaatc cctggtctgg gaggaatgga aaatcaaaca    43980
actttataat gagataaatt attagatcta ctaaaaaaga aggaaaagaa attaaataga    44040
tcaataatca taaaaataca ttgaaaaact ctaaaaaaaa agaaagttcc accccccaaa    44100
atacattgaa aaactctaaa aaaaagaaag ttccaccaaa agaatccaac agacccaatg    44160
gtttaaaagt tttgttttgt tctgacaaat tttcttgtt tttcttttt ttttttctg    44220
agacagagtt ttgctcttgt tacccaggct agagtgcaat ggcgcgatct tggctcactg    44280
```

```
caacctccac ctccagggtt caagtgattc tcctgcctca gcctcaagag tagctgggat   44340
tataggcgtg tgccaccaca cccagctaat tttgtatttt tagtagagac ggggtttctt   44400
catgttggtc aggctggtct cgaactcctg acctcaggtg atccgcccgc ctcagcctcc   44460
cacagtgctg ggattacagg cgtgagccac tgtgcccggc ctgttctgac aaactttcat   44520
agtacagatt attccaatat cattcaaact tttccaaagt ataggaaaac aagggatgtt   44580
ttcagcttat tttatgaggc tggaaaaatc ctcatatcaa aacctaaaaa acagccaggt   44640
gtagtagctc acgcctgtaa tcccagcact tgggaggct gagacgggca gattgcctga    44700
gcctcaggag ttcgagacca gctggggcaa tgtagcgaga cctcatctct cttttttttt   44760
tttttgaga cagagtctct ctctgtcgtc caggctggag tgcagtggtg ccatcttagc    44820
tcactgcaac ctccgcctcc caggttcaag cgattctctt gcctcagcct cccgactagc   44880
tgggactaca ggtgtgtgcc accaagcctg gctaattttt tgtattttt ttagtagaga    44940
tggggtttca ccttgttagg caggatggtc ttgatctcct gacttcatga tccaccggcc   45000
acagcctccc aaagtgctgg gattataggc atgagccacc acgcccagcc tttttttttt   45060
ttttgagaca gagtcttgct ctgttgccag gctggagtgc agtggcgtga tctcagctca   45120
ctgcaacttc tgcctcccag gttcaagcta ttccctgcc tcagcctccc aagtagctgg    45180
gactacaggc gcgcgccacc acccagct aatttttgt gttttagta gagatggggt        45240
ttcactgtgt tagccaggat ggtctcgatc tcttgacctc gtgatccgcc cgcctcggcc   45300
tcccaaagtg ctgggattac aggcgtgagc aaccgcacct ggcttaatta aggatctttc    45360
taaacacaag aaagaatatt tatcagaaac caaagggagc atgatgcaca gtggtgaaac   45420
actattctca gtaaaaacag caaaagataa ggatgtcttt taccattgat acttttctga   45480
gggatccagc ctatgcaaaa agaaaagaa atgagggtac aaatattgga aagcaaggga    45540
cagaactctt attatttaca gatagatagg tcttcctcga agatccaaga gaaacaaaac   45600
taacaataac aattggaact agcaaggttt agaaaggcca ttgtatacaa gataaatatt    45660
tttagaatct gcagttcccc taatcagtag cagcagtaac ctgttagaag atgtaatgaa   45720
agtaaagatc tgggccaggc acgatgtctc acgcctgtaa tccaagcact tgggaggcc    45780
aaggtgggca gatcatgagg tcaagagatt gagaccatcc tggccaacat gatgaaaccc   45840
catctctact aaaaatacaa aaattagctg ggtgtggtgg tacgcgcctg tagtcccagc   45900
tactcgggaa gctggggcag gagaatcgct tgaacctggg aggcggaggt tgtagtgaac   45960
caagattgcg ccactgcact cctgggcgac agagcgagac tccgactgaa aaaaaaaaa    46020
aaaaaaaaag aaagatctga ttcatagtag taaaactaaa tgtatgcaat ttgcatatac   46080
tattggtatg tatgggaaaa tatctggaaa cacatatact aaatcattaa agtagtcggt   46140
cataggagac tttttttactt tctgtgaggg gttttaccgt ctttaatatc ctataatcag   46200
ggacatttt tcttttctc cgtgaccccc tgctttttaa aaaattgtgg tgaaatacac      46260
ataacattac atttcaaatt tacctttgta acctttgttt tttttttttt tttttgagac   46320
agtctcactc tgtcacccag gctggagtgc agtggtgtga tcacagctca ctgcagcctc   46380
aaccacctgg gcctagcga tcctcctgcc tcagccttat gagtagctgg gactacaggc    46440
acatgccacc atgcccagct aattttttt ttttttttt ttggtagaga tgggctcttg     46500
ccatgtttcc caggctggtg ttgaactcct gggctcatca actgatgaga aagagctctc   46560
caggcagaaa gaagatcatg ttcaaagaca gaaacagaaa tgtgtattct tgggagaagt   46620
```

```
gtagaaagtt cagcatctga ttgggtcggg aagacaagc tagtcaaggc cacatgatgt    46680
tttaattagt catgcctaac agtggggccc tggaagagca gtttaccaca aggggccaac    46740
tgcttcggtt tgaacccgca gccctgccac ttgctctgta accttaagta aacaattttt    46800
actctctctg ttcctccaat gggagtgata acaataccct tctcatagaa ttaattcata    46860
catgtaaaat gcttagaaca gtatctgaca cataaatgca aaataattta actgctttct    46920
gctgctgctg acatcactat catcaccctc accattactg taggaaatgg ggacccagtg    46980
aagaattttt ttttttttctt ttgagacaga gtctcactct gtcacccagg ccggagtgca    47040
gtgacgcgat ttcggcccac tgcaacctct gcctctcagg ttcaagcgat tctcatgtct    47100
cagcttccca gtagctggg attacaggca tgagccacca cactgggcta attttttgta    47160 ttttagtga ataggggttt caccatattg gccaggctgg tctcaaactc ctgacctcag    47220
gtgatccatc cacctcggcc tcccaaagtg ctgggattac aggcataagc cactgtgtcc    47280
ggccctagtg aggaatttta agcagaaaac tgatatgctc aggtgtgagc gaggtggtag    47340
gtaacactta ctgtgcagtg ccctgtagcc caagaggtta gcacacaggc atttgctcag    47400
gcagcactag gattttctgc tgtggaaaac ctttgtattt tatcctgctc cacaagataa    47460
aaataagtgg tttaagtcaa tttggataga ggctccaact taccatggga ggtaggaaag    47520
ccaaagttat cccaaggatg ttttcaatcg tacggattag gggtctgcaa actgtgagcg    47580
tggcccaaat ccagcctgct gcttgttttt gtaaatgagg ttttttcgga acccagccac    47640
actcatttat ttatgcatta tctgtggctg ctttggtgct gcagtggcag ggctatttgt    47700
ggcagggact gtatgaccca ggaaaccaaa aatatttacc ctctgtccct tagagaaaaa    47760
gtttgcaacc cctgatataa agctataagt tggttatttg tggcctcaac ccaggcctca    47820
ctgctatttt ttctgtttac aatacctggc atgctcttaa gtgtctagaa ttggttaaag    47880
atagaagagt ggatgtaatc cctgctacca agggctgtca ggctagttgg gattataagt    47940
acacaaacac tcaaagtgag aaaaacacag aaaaggatgt gtgtcatttt gtctaaggaa    48000
gttgaataag atttctcagg aaaagaaaca tttgaactga atttgaaggt gagtgagttc    48060
aggtgtgttt gggctgaagc ccaggccatg ctgagtggat agcgggtggg aagagagtgt    48120
ggaaacacac tgcatgcagg gaagagttgg gagtctgggg tgaccaaggc acagggaggg    48180
aaagttgaag ttatcaattg tgtgaaacag ctttctgtgt tggcctgaga tgtttatagc    48240
tggaagcagt ggggagccaa tacagttttt tacgaaggta ttagaggtgg gtttctgtgg    48300
gtgatcgtta atcatgtttt ctcccttttaa gtgtagtcct gcttgagaaa tagacatgag    48360
aaaggaatga aggttaaaac atcagctgta ttgttggtaa aactagaatg gaaagtgtgg    48420
cttgagctgg taaccatagg gcttttccaa tgcctgtgcc ctgagttaga tcttggggta    48480
gagagactgg atgtgcagag cagcaccccc accccacccc agccatccat atggagcttc    48540
agctgccata gaccaacaag gcagagggat aggcctctag acctgcttct agaaaccagg    48600
ctgctgctct tgcttatggt gggccctagg aaggcaagag tgagggagg gaggcaccag    48660 cttaggtgct gggttctttg aagatctgtg tgtacacaga gtctttctct ccatcttacc    48720
aatcagatga gtcactgtca ctgtgggaag aagtaggggc atgggtcacc ttcccaaaac    48780
ttctaagaag tttgtattct gtgggcttgg atagggacca tgggaaagga agagaatggt    48840
tgcccataaa actggctgta gtgtggcctc aaacttctgg acttaaatga tcctcccacc    48900
tcagcctccc aagtagctag aactacaggt atatgccacc atgcccagct agttaaaaaa    48960
aaattttttt tttttttggg ttgagatgag gtctctttct atgttccctg ggccggtctc    49020
```

```
aaactcccag cctcaagtga tcctcctgcc ttggtttccc aaagtgctag gattataggt   49080
gggagctacc atgccttagcc caagcctgta attttttttt ttttttttttg agatggagtt   49140
tcacttttgt tgctcaggct ggagtgcatg gcgcagtctt ggctcaccac aacctccacc   49200
tcccgggttc aggcgattct ccttcctcag cctcccgagt agctgggatt acaggcatgc   49260
accaccaagc tcagctaact ttgtattttt agtagagatg gtttctccg tgtcggtcag   49320
gctggtctca aactcctgac ctcaggtaat ctgcccacct tggcctccca aagtgctggg   49380
attacaggca tcagccaccg cacctggcac gaacctgtaa ttttttaagtt tcatatgcta   49440
tttatttttt gttatttctt taattcattc attcatttat tcattcgaga tggggcctca   49500
ctatgttgac taggctagtt ttgaactcct ggcctcaagc agtcctccca cttcagcctt   49560
cccaagtgct gatattatag gtgtgagctg ctacatccag ccttctttct tcttttttctt   49620
tttccatgtg ctatttgaca ttttccaagg taccagcctc cccttctccc caagataata   49680
tcttttaata tggaatttca tccctagggc aggactttt tttattatc cctcagaaat   49740
atactggaca ccacgtttaa gtagacatcc aacatctgct gtcataaatt gttttgaatt   49800
ttttgacata cttgcccatg aggttttga aggcatagac catgtcttag ctgaacatgt   49860
ggtctcttag tgccataaag ggggtttatg gtatgacctg tgtagtgtca cctgtgtagt   49920
gacagcacca ctgcctctgt ttcccttcct cttgtgatgg cagcagcgtc tcaagccaaa   49980
caagaagggt agttagggtg ggatggaagc tgggtagagg tattcctctc cccatagttc   50040
tgtgttcaca tgtgcattga cctccttttt ggcagcaagg gggccaggcc aaccacccca   50100
cagcagccgt ggtgacggag aagcagcaga tgctggagca gcaccttcag gatgtccgga   50160
agagagtgca ggtgatgcaa gttacaagcc tcggcaggg agctttcatt aattttttttt   50220
ttttttttttg agacagggtc ttgctctgcc actcaggctg ggctgcagtg gcatgatcac   50280
agctcactgc agcctcgacc tctcaggccc aagcgatcct cctacctcat cctcccaagt   50340
agccgggacc acaggcatgc accaccacgc ccagctaatt aaaaaaaaaa aatttgtaga   50400
gatgggggtc tccctgtgtt gtccaggctg atcatgaact cctgggctca agtgatcctc   50460
ccaactcagc ctctcaaagt gctggcatta caggcgtgag ccactgcacc tggccaacag   50520
ggagccttct cttggggata ctgcctgcag gtcctgcatg tatctttttt gaggttttgg   50580
cttcatttga attctcctca gaaacttat attttctgtt cccaaggaaa tctttcttta   50640
cttctgttttt tttgtttgct tattttaaac aggatctaga acagaaaatg aaagtggtag   50700
agaatctcca ggatgacttt gatttcaact ataaaaccct caagagtcaa ggaggcaagt   50760
gaatattaga gatgttaaaa tctctagaaa gtgagtttgt gttgttgagt tgaaagactc   50820
atttgtctta actctgttta gatcttaagg cgggcgggc gcaagggagg tacgggtcct   50880
caaaggagcc tggtcattaa ggacaggagt attccctcag gtccaggagt attccctcag   50940
gtccaggagt attccctcag gtcaaggagt attccctcag gtcaaggagt attccctcag   51000
gtccaggagt attccctcag gtccaggagt attccctcag gtccaggagt attccctcag   51060
gtccaggagt attccctcag gtccaggagt attccctcag gtcaaggagt attccctcag   51120
gtccaggagt attccctcag gtccaggagt attccctcag gtccaggagt attccctcag   51180
gtccaggagt attccctcag gtccaggagt attccctcag gtcaaggagt attccctcag   51240
gtccaggagt attccctcag gtccaggagt attccctcag gtccaggagt attccctcag   51300
gtcaaggagt attccctcag gtccaggagt attccctcag gtccaggagt attccctcag   51360
```

-continued

```
gtccaggagt attccctcag gtccaggagt attccctcag gtccaggagt attccctcag    51420
gtccaggagt attccctcag gtccaggagt attccctcag gtccaggagt attccctcag    51480
gtcaaggagt attccctcag gtccaggagt attccctcag gtccaggagt attccctcag    51540
gtccaggagt attccctcag gtcaaggagt attccctcag gtcaaggagt attccctcag    51600
gtcaaggagt tttttcttcc ttcgcagaca tgcaagatct gaatggaaac aaccagtcag    51660
tgaccaggca gaagatgcag cagctggaac agatgctcac tgcgctggac cagatgcgga    51720
gagtaagggc ataggtcgga ccacttcccc catgtgtctc gctcacttgc gggatttcag    51780
cgtcttgtgg cagaacttgc ttggtttcta agaagttcct gctctggagt tgactaaaga    51840
atgtggttag agacagtctg aggaaatgtt ttctgacttt gttttggttt ccaaccagag    51900
catcgtgagt gagctggcgg ggcttttgtc agcgatggag tacgtgcaga aaactctcac    51960
ggacgaggag ctggctgact ggaagaggcg gcaacagatt gcctgcattg gaggcccgcc    52020
caacatctgc ctagatcggc tagaaaactg gtaaaggatg aaagaagctt ttcctttctt    52080
tctcgaaagc tagattgaat tctgatctta actgcaggcc cacagaattg gtactatatc    52140
tccaacgtgg ggactttcc atattcaaat ttagcccaag aattaaagtt tttactttat     52200
ttcggccagg cgctgtggct cacacctgta atcccagcac tttgggagac caagatgggc    52260
ggatcacttg aggtcaggag tttgagacca gcctggccaa catggtgaaa acacatctct    52320
actaaaaaca taaaaaaatt agccgggcgt ggtggtgcgc acctgtagtc ccagctactc    52380
tgggcggctg aggcaggaga atcacttgaa cctgggatat ggaagttgca gtgagcggag    52440
atcttactac cgcacaccaa ccagcctggg agacagagtg agactccatc tcaaaaaaat    52500
aaaaataaaa taaagttttt actttatttg gagaaacttt gttttaaaaa atgtatttat    52560
attattatat tttaagtata ttttacttaa taattcaatt aaggcttttg gtttaactgt    52620
atttaacaga tagacaaacc ttttaatttt agttatttta gtaatctaaa atgacacatg    52680
ccctttttaa gggaaaaaat tcaaatacag aaaattaatc aagagaagaa aaattttta    52740 aatgaaatca tcagcagtac tagtagttaa atttagttg atgctcaatc tagacatctg     52800
tcattatgta tatacacatt atgtatatac acataaagat agaaatttat acagtttata    52860
ttaggatcat ttttttttct ttttttggag tcagggtctc actgtgttac ccagtctaga    52920
gtacagttat gcagtcatgg ctcactggag ccttgacctc ctgggctcag gcagtcttcc    52980
caccttagcc ttctcagtag ctgggactac aggcatgcac caccacacct ggctaatttt    53040 taaattttt atagagacag ggtcttactt tgttgcctgg gctggtctca aattcctggg     53100
ctcaagggat catcccactt cggcctctca aaagctctgg aattatagat gtgagctgcc    53160
gtgcccagcc caggatcttc ctttatatgc tttttctgtaa tttgcacttt taccttcatc    53220
cagcatatct tactgcaacc cttcctgtgc aaggccctat agtgagcatg ttgcaccagc    53280
ttgccttagg agaaacttga gatacagagc ctgcactgga aatttagcgc aactctacat    53340
gagaatgcct gtctattcat atcctcacta accctgagtg ttgttaattt actgaaagca    53400
gtttaaaatg cttcctgacc agggaacgaa gaagcttaag ttctgggaat gggaggatag    53460
aagtgccaga aaagagctca ggagttcaga aatccctgca gcggtccccc tcctctcct     53520 ttcactttct gtctttctgg tcttttggtc tttgttacac tagtgataaa ccatcaaaga    53580
atgatggaat gatgctaact tctctctttt tttaattttt ttgagacaga gtctcactct    53640
gtcacccagg ttagagtgca gtggcatgat cttggcttac tgcaacctcc tcctcccagg    53700
ttcaagcgat tcttagtcac aaccttccaa gtagctggga ttacaggccc atgccaccat    53760
```

```
gcctggctat ttttttgtat tttagtagat cgacctgcct cggcctctca aattttgggg    53820
attacaggtg tcagccactg cacctggcct aatatctcta ttcttggaga tagatttaat    53880
gagcttttc tccctctcta ttcacttatt ccttgtgcat gttatcaata ttttgaaaca     53940
taatgtcatg tcctttgatc agttgaaggc tgacattgaa aaggcttatg gggattgggt    54000
gttgtggctc acgcctgtaa atcccaatgc tttgggaggc agagtcggga ggatcacttg    54060
aacccaggag tttgagacca gcctgggcaa caaagtgaga tcccatccct acaaaaattt    54120
aaaaaactag acatgtgcca ttacacttca gcctgggtga cagagtgaga ctccatctca    54180
aaaaactaaa ctaaactaaa caggcatggt ggcacacacc tatagttcta gctactcagg    54240
aagctgaggt aggaggatca ctcatgtcca ggagttggag gaggcagtga gctatgatca    54300
tgccattgca ctgcactagg ccacagagtg ggacctgtc tcaaaaaaaa aaaagaaag      54360
aaagaaaaga aagggctcat gtagttcaag cccttctctt catgcaaggg gatgctaagg    54420
cccatgatgg tgaagggcct ggcaaagctt gcacagatag tgtgtgacag agctggctca    54480
aacccatctt tgggagctgt ctaatctctt tttctgagtc tttatgttca tagacaagtt    54540
aggatgagta aagtaagtgc taaattccat atttcgtgtt ctgcatatct gggctcagat    54600
gcttgtcatt ttccagtgat aactccatca atgcctccta gtggtataaa ttttaatact    54660
tcttgtgtgc ccagcccct cttagaaatt tgagatttta ggaagggact agtaataaaa     54720
ggtaaaataa attattttct ggccaggcat ggtggctcac acctgtaatg ccagtacttc    54780
gggaggtcga ggcagatgga tcacctgagg tcaggagttc aagaccagcc tggccaacaa    54840
ggcaaaatcc catctctact aaaaatgcaa aaattatccg ggagtggtgg tgggtgcctg    54900
taatcccagc tacttgggag gctgaggcag gagaatcact tgaacttggg aggcggaggt    54960
tgcagtgagc tgagactgtg ccactgcact ccagcctggg caacagagta agactctatc    55020
tcaaaaaaaa aaaaaaaaaa aaaaggcca ggcgcagtgg cttacacctg taatctctca    55080
ggaggctcag gcaggagaat cacttgaacc cgggaaatgg aggttgcagt gagccgagat    55140
tgcaccactg cactccagct caaaaaataa ataaataaat aaattatttt cttttttat    55200
ttatttttc agcatccacc caacatggtg aaaaattcct cttttcttaa tgtcactgaa     55260
ctgtaaactt aagatgaaaa attgtaaatt tcatgctata tatatttcac cacaataaaa    55320
aaattccttg ttcttattgt agtggtctcc atgtcttcag tatttccttc cccttctcca    55380
tctcacctgt atacattcac tttggtaatt agcatctttc ttaattatt ggcaggataa     55440
cgtcattagc agaatctcaa cttcagaccc gtcaacaaat taagaaactg gaggagttgc    55500
agcaaaaagt ttcctacaaa ggggacccca ttgtacagca ccggccgatg ctggaggaga    55560
gaatcgtgga gctgtttaga aacttaatga aaaggtaatt tagcatcctt gtccctttcc    55620
ctcatctaaa aaatacctaa agactcacgt ggtagagtga gaggcgggct gacttctggt    55680
catggccgtg gcgcgtgagc ccatcttctc tttcctcagt gcctttgtgg tggagcggca    55740
gccctgcatg cccatgcatc ctgaccggcc cctcgtcatc aagaccggcg tccagttcac    55800
tactaaagtc aggtaggcca tgccacttcc atttccagta gagattttac tgagggacac    55860
tgttagggtg agggtagagt tggtggccag ggtcattctt tccaggtgtg gtgtcacagg    55920
cagtacactg ttgcggggtt gaaatttgtt gccatactat ctgcttgctc tctgattctg    55980
atgtcaaaag caaagagca gtcatctttt tgaaggtacc tggcatatt cctatgattg      56040
tagacctgga gtctcaggcc acagcttctc cttctgccca agggacaaaa taatgtcatc    56100
```

-continued

```
tattttctgt tctttgaggc tactcttccc tgtggatttt aagggaaaga gtaaggctta   56160
gtgatgggga agctgagagg ccccagggca ggtgggtggt gggcctgtag ggtgaggtgt   56220
tactttcaca ctcaagtcag aacaggtgtg ctggggtttt gaccttctgc agcaaaattt   56280
ccctcctcag aaacttagta tggtgttcgg tttcaggatt aatagaacaa atgccagct   56340
gcacagcatg tgttcctgta atattttca ttatatggct ttgattatcc ttttgtgaat    56400
ctctcacaac tttaagttgt tagttcttag atgttttctc agtacctttg gcttgaagga   56460
gtgatactca tcttttgttt ttgtttgaga cagggtctca ctctcaccca ggctggtgtg   56520
cagtggcatg atctcagctc actgcaacct ccatctccca ggttcaagtg attcttgtgc   56580
ctcagcctcc tgagtaactg ggaatagagg tgcgtgccac cacacccggc taatttttt   56640
ttttttgaga cagagtctcg ctcttcggc caggccagag tgcgtgttgc aatctcaact    56700
cactgcaacc tccacctccc aggttcaagc gattctcctg ccttagcctc cctgagtagc   56760
tggaccggca cactccacca tgcccggcta atttttgtat ttttagtaga cagggttt     56820
ctccatgttg gccaggctgg tctcaaaact cctgacctca gtaatccacc caccccggcc   56880
tccaaaagtg ctgggattac agatgtgagc caccacgctc ggccttttt tttttttt     56940
ttttttgag atggagtctt tctctatcac ccaggctaga gtgctgaggt gtgatctcgg    57000
atcactgcag cctctgcctc ctgggttcaa gtgattctcc tgcctcagcc tcccaagtag   57060
ctgggattac aggtacctgc caccatgccc ggctgatttt tgtattttta gtagagacgg   57120
ggtttcacca tcttggccag gctggtctcg aactcctgac cttgtgatcc acctgccttg   57180
gcctcccaaa gtgctgggat tacaggtgtg agtcaccgca cccagcccta ttttaatttt   57240
tttaaagaga gagatagggg ccaggcacgg tggctctcgc ctgtaatccc agcactttgg   57300
gaggccaagt gggtggatc acctgaggtc gggagttcga gaccatcctg accaacatgg    57360
agaaactctg tctctactaa aaatacaaaa ttagctgagc gtggtggcgc gcgcctgtaa   57420
tcccagctac ttgagaggct gaggcaggag aatcacttga acccaggagg cggaggttgc   57480
ggtgaacgga gattgcgcca ttgcactcca gcctgggtaa cgagagaaac tgtctcaaaa   57540
aaaaaaaaag agaaagagag ataggatctc gctctgtcat ctaggctaga gtgcagtggc   57600
atgatcatag atcactgtag ccttgaactc ctgggcacaa gtgatcctct tgcctcagcc   57660
tcccgagtaa ctgcgactac aggtacatgc taccacaccc cgctaatttt taaatttttt   57720
atagatgtgg gctctcactt tgttgcccag actgttatgg aactcctggg ctcaagggat   57780
cctcccagct tggcctccca cagtgctgag attatagatg tgagcctgta attatagaca   57840
gcttggccta tttacctgtt ggaaatgaag aattatgaat tttacatttc ttcaagaaaa   57900
ggttatggga gagttactga cttttttcc ttggattttt tcttttaaa taggttgctg     57960
gtcaaattcc ctgagttgaa ttatcagctt aaaattaaag tgtgcattga caagtaagta   58020
ctcctatctt agctctgttt ttcaaatgag gaatagaaaa atgagaactt tgacagacat   58080
catttgaact agagactctg tctttattca gagatcttca ttttgtggac aaaagttttc   58140
aaaagccttg gggtgcattg tcatttacgt gtctgaacaa agccacaaag ctgggggtac   58200
agatttgatt tgtggttgct attgtgacaa ccagtccctc ttttccttgt ttagtttttt   58260
acttgtacat gtcattcatg catattatat ataagactga gatcatgtgt taattaacga   58320
ctgggatacg ttctgcaaaa tgtatcatta ggcaattttg ttgtgcaaat gttgtagagt   58380
atatagtcct tacacaaacc tgggtggcag aacctactgc acacctacgc tatgtggcag   58440
agcctactgg tcgtaggctg taaacctgta cagtatgtta ctgtgctgaa taccgtaggc   58500
```

```
aattgtaaca catctcaatg aagtaggaat ttttcagctc catgataatc ttatgggacc    58560
accatcatat atgcattttg ttgttgaccg aaacgtcgtt atatattctt tccatacata    58620
gcatgtggaa agaatagatc tcttttttt aattgttcca cactttacca tataatggaa    58680
tacgcaaaat ttcacaatac ctttcaggat gtaaaataca tataccctt gacgacatta    58740
gaaaagagaa aatgtgggcc gggcgcggtg gctcatgcct gtaatccag cactttggga    58800
ggccgaggcg gcggatcac gaggtcagga gatcgagacc atcctgggta acacggtgaa    58860
accccgtctc tactaaaaat acaaaaaaac tagctgggcg tggtggcggg cacctgtagt    58920
cccagctact caggaggctg aggcaggaga atggcatgaa cctgggaggt ggagtttgca    58980
gtgagccaag atcacaccac tgcactccag cctgggcgac agagactcca tctcaaaaaa    59040
aaaaaaaaag aaaagaaaag agaaaatgtg gctgggcgcg gtggctcacg cctgtaatct    59100
cagcactttg ggaggctgag gtgggcagat cacctgaggt cgagagttcg aaaccagccc    59160
gaccaacatg gagaaacctt gtctctacta aaaatacaaa attagccagg tgtgttggcg    59220
catgcccgta atcccagcta cacgggaggc tgaggcagga gaatcacttg aactcaggag    59280
gtggaggttg tggtgagccg agatcacacc attgcactcc agcctgggca acaagagcga    59340
aactatctca aaaaaaaaa aagaaaaaag aaaagataaa atgcattctt attttttagtt    59400
gatgtaatta tgtggaaatt tcatgaggat gcactggaaa ataatgaaat aagggagttg    59460
acgaaggtgg taggtttaat aagtacatat gcaatatgaa acataggttc cccttcctat    59520
ggggaggcaa ccaactgtgc ctgctacgca gaggtgttat gttgcgctga tcaactgtaa    59580
ctgaatagtt taagaaatg cccaggagca cagaggtttt ttcatgacag taaataacag    59640
gtggtcaaag taggcttttt gaagaaacac agagcctatt ttattaacaa cagtctgtgt    59700
tcttacagag actctgggga cgttgcagct ctcagagggt aagttcagcc tagaggcttc    59760
cttttgttcc gtttaaccta acttcatcct ccggctactt ggtcacctac atagttgatt    59820
gttcccctgt gattcagatc ccggaaattt aacattctgg gcacaaacac aaaagtgatg    59880
aacatggaag aatccaacaa cggcagcctc tctgcagaat tcaaacactt ggtatgtggg    59940
aggagctccc cttcacaaag ggcctctggc tgccggagag ggctagggag agcctcacag    60000
gacacctgcc ttttctttt cttacagacc ctgagggagc agagatgtgg aatgggggc     60060
cgagccaatt gtgatgtaag ttttgttggg gatgaaagac aactgggtg ttttcctga     60120
gggagagagg ggtaaagatc cttcttaatc cccagaatta gaaacatcaa cctgttcttt    60180
cagctgtagt tattccaaaa agtcacttca ggccaaagtg acatgaacag aagttccatg    60240
tgccatggag ctctctggct tggaacattt ccgtgaatat ctgggagttg ctcctcctt     60300
aaggagaagt ggaaagtccc ttgctgagtt gttctccaca cccatgtggt ataaagcagc    60360
tttccacctt gcctggggct ttccaaattc cccatccagc tcctgcggct gaccctgctt    60420
ggctccattt ttagtgccct gtttttctct cccactgagg tgggatagag ggtgtaaaag    60480
caacagattt gagttaaact ttaaaataaa tgaccacctt gcattagctt gcttaggaaa    60540
agagtacata aaataaaatg aacaaacaaa aacccatctt gttctttatc ccccttattt    60600
tctgcttttc attgattcag attattggat tcttattgtc aagaataaac tttaaacaaa    60660
caaacaaaaa aaggtaaatg tgacggaagg ctagttttca gtcattttta aaattgtga     60720
tgccccgttc ttttcttac atttgtcccc tgaacaattc ttcctcttta aatgtagca     60780
gtcctagctg ggcgtgctgg ctcacacccc gtactttggg atgccaaggc aggctggtca    60840
```

```
cttgaggtca ggagttcaag accagcctgg ccaacatggt gaaagcccgt ctctactaaa    60900
gatacaaaaa ttagctgggt gtggtggtgc acgcctgtag tcccagttac tggggaggct    60960
gaggcatgag aatcgcttga acctgagagg tggagcttgc agtgagccaa gattttgcca    61020
ctgcactcta gcctgggcaa cagagtgaaa ctctgtctca aaaaaataaa taaaataaaa    61080
tgtagcagtc cttttttaaaa atgtggaatt ttacttgaca gtagagtgaa gtagcctgta    61140
tgcaatgata tgggaaaatg tacatgacat attaagaaaa agcaaaatgt aaaataattt    61200
gaatagtatt attagtatat gtgttttaaa aatacactat actcttatgt gtattcatat    61260
gtatattaag aaattctgga ggaatatacc agcagtgcta tgtgtattag tgctgctgtt    61320
ggtatccatg gctattctag actgtctctg tgatatttgc attttaaact gaatatatta    61380
cttttataat cagaaaaata gtattaaaaa tgaattataa tttaatttct tttttctttt    61440
tttttttgga gtcggagtct cgttctatcg gattgcagtg gtgcgatctc agctcactgc    61500
aacctctgcc tcctaggttc aagcgattct cctgtctcag cctcccaagt agctgggacg    61560
ataggtgcat gccaccacgc ctggctaatt tttgcatttt tagtagagac agggtttcac    61620
catattggtc aggctggtct tgaactcctg acctcgtgat ccacccatct cggcctccga    61680
aagtgctggg attacaggca tgagccgctg tgcccagact agaattcaat ttttgagaat    61740
tcattgacaa ctcttactta aaataaggtt gctgtactga tgtgagacat tgttgtagtc    61800
agtttggaaa acaatttggc agtataaaaa tgaacatacc tgtaaaccaa cggtgccatt    61860
cccaggattt aatagcagag aaatctttgc atatatgtcc caggagacat atataaagtg    61920
gacatcagcc tgattataag ctctaaatgc aacccaaata aatacccatc aacattagaa    61980
tgaatacatt atttgtggta tagacacaat ggaatactcc gcagctgtga aaaggaatac    62040
actgcagata cacataacca tgtggattca tttcacatca agtgaaaagt gaatcccaaa    62100
agaattcatt ggagtccata agtgtaaggt tcacaaatgt cccaaactaa acaatacctg    62160
cattgcttag ataaacaaat atggtaaaac tgtaaaaaaa caaaacaaaa caagacaaaa    62220
agggctagga aatgataaac ccaaaagaca aaatagcagt tatttctgag ggaggaggga    62280
aggggatggg gttggggaag ggcacccaga gaattttagg agtgatggac ttttccttaa    62340
attgaatggt gggttcatat tgttttgtta ttctttgtgc cttacgtatt ttacaaataa    62400
ccaattggat ctatgtaata ttataataca aactgagtaa aggattaggt tgaggatcac    62460
agcattggaa gttcttggtg ttgaagagag taagtgccga gcaagttgtg tccctggcag    62520
tttgtttgtg accacctggt ggcttaccct tcttggtgtg gtgaggcttg gcatgtcact    62580
ttccttggct gtggctgtta gtactgaatg ccattctctc tgaggaaaag tgtccttctc    62640
ttttttattg attgactgat tgattgagac agagtctcac tctgtcaccc aggctggagt    62700
gcagtggcgt gatctcggct cactgcatcc tctgcctcct gggttcaagc gattctcctg    62760
cctcagcctc ctgagtagct gggactacag gcgcccacta ccacacccag ctaattttg    62820
tattcttagt agaaacgggg tttcaccaaa ttattggcca ggctggtctc gaactcctga    62880
ccatgtgatc cacctgcctc ggcctcccaa aatgctggga ttgtaggtgt gagccatcac    62940
gctcagcctt tttttttatt taatttaatt tttttttaag acagggtctc actctgtcac    63000
cccagctaga gtgcagtggc acaatcatag ctcgctgcag cctccatctc ctaggctcaa    63060
gccatcctcc cacctcagcc tctcgagtag ctggggctat aggtgtgcac caccacaccc    63120
agctaatttt tgtatttttt gcagagatgg agttttgctg tgctgcttag actggtctcg    63180
aactcctggg ctcaggcaat cctcctgcct tggcctccca aagtgctggg attacaggca    63240
```

```
tgagccacca cacctggcct aagagtgtcc ttctcgttac tgtaggcttc cctgattgtg    63300
actgaggagc tgcacctgat cacctttgag accgaggtgt atcaccaagg cctcaagatt    63360
gacctagagg taagttctgc agcagaatcg gtgagaggct acgtacaggg gtgactcagg    63420
acaaaaactt ccactgggat ttttacaaga gaaggtggaa tgattactgt ttgcttaaca    63480
ctgtgtttat ttttgcttac ttttctccaa aaaaatcctt ggcatcccat ctggcaataa    63540
agtcttgctt gaatgcttag aagatgtgtg tatattcagc tttcagcaaa cttgatatga    63600
aaatctctat ttagaaattg attggccggg cgcggtggct cacgcctgta atcccagcac    63660
tttgggaggc tgaggcgggt ggatcacgag gtcaggagtt cgagaccagc ctggccaaca    63720
tgacgaaacc ccgtctctac taaaatacaa aaattagctg gtatggtgg cggacgccta    63780 taatcccagc tactcgggag gctgaggcag gagaatcact tgaacctggg aggcagaggt    63840
tgcagtgagc tgagattgtg ccattgcact ccagcctggg tgacagagtg agactccgtc    63900
tcaaaaaaaa aaaaaagaaa ttagaactga ctttataaag tttgggcata agagtcttag    63960
cagccagtgt gtttagtata cagaaaattg tggcaatgac attctccttt cccaactttc    64020
ttgattttta aattaagata tacctagaaa agcaggaatc ctggtctttg attcctgaga    64080
cctccctgtt tcatgtgaag atacagcttc aagtcttgga gaatgcctcc aaggtcttaa    64140
aaatggggaa tctgtggatt gtgagtcaag ctttgagcaa gtcaggtttt acaagggacc    64200
ggtatattcc gactgcagcc tgagttgtgt ggccacgctg ggcattcttt ccactatgag    64260
tgctcactga gctgactcac tcacactcct cgcctagagt tggcagcagg tgtggtttat    64320
ggcatgtcct ttcattctga gccccgtgag atgcgggtga agagatttcc aaggctgtga    64380
gagcccctct gcctcccag ctcagtcccc actccctccg cagacccact ccttgccagt    64440
tgtggtgatc tccaacatct gtcagatgcc aaatgcctgg gcgtccatcc tgtggtacaa    64500
catgctgacc aacaatccca aggttagtgc cccctccttt tagttggtgc cccgggatct    64560
cttgcgactt aggggtacct agtatagaca atgagcacca tccctcatct aaacaagcaa    64620
atgtgttctt tccaatagaa tgtaaacttt tttaccaagc ccccaattgg aacctgggat    64680
caagtggccg aggtcctgag ctggcagttc tcctccacca ccaagcgagg actgagcatc    64740
gagcagctga ctacactggc agagaaactc ttgggtccgc atttcacccc ttctccctcc    64800
cgcccacccg cccagaaaag ggatccggcc catagggctg ttcatttggg ccatgtctac    64860
tgagcattag gccatgtttc tttcctgagc aaggcgctgt gctggtgcca ggaaacaggg    64920
gagttgggga gttggggtgc agagacagtt tgcagttttc agtcgaggtg atcattttg    64980 aggtgggagg tagatttctt ttctcctggt tgctgtctca ttcacccact ctatctaact    65040
ttagaagatc ttttaagtgt gtgttggaag gtggcactaa aggcttgaca ttccctgtcc    65100
atttttttaa taaactatag gctagttggt ttttttgtc ttattttatt tatttattta    65160 ttttttgag acgagtcttg ctctgttgcc caggctggag tgcagtagtg tgatctcggc    65220
tcactgcaac ctccgccttc tgggttcaag cgattcttct gcctcggcct cccgagtagc    65280
tgagactaca ggtgctcacc accacgccca gctaattttt gtattttag tagagacggg    65340 gtttaccat gttggccagg atagtctccg tctcttcacc tcgtgatccg cccacctcgg    65400
cctcctaaag tgctgggatt acaggcttga gccactgtgc ccagcgtagg ctagttttta    65460
aaaaagaatt agtggaatat tttatgtgcc acctgggcta gaagtagctt tgttctaata    65520
aagctgttgc caccaaatac acctgtctga cacccgatgt cagcttgtta gtgagtgctg    65580
```

```
ctgttggttc ccagcctacc acccgaggtt gggaagagca ggggggacttg ttatatcacc    65640 ctccatccct gctgggctac ccagcaacac aagtgagtca aatgatggga tagtgtttgt    65700
cctcatgtgc acacacacaa cagtgcctac cttcaaagat gtgaaagctg attattttgt    65760
ggcccattgt gggatgaatg tgtgtgtgtt ctgttttaag aaataacctc ttgaccccaa    65820
gctgaaaatg tactacttga ctcttttttct ttccttcagg acctggtgtg aattattcag    65880
ggtgtcagat cacatgggct aaattttgca aagtaagcaa tcttgttaaa ttctcgtggg    65940
aatgggaatg ctcacctgca cggctgtcgt tgagggctct ggcttgaagg ccctgaactc    66000
ttggtccagc ggccagtagg acctgcctga aggtagacgg gcctgaggat ttgggtgatg    66060
cactgcaccc ctaggaaggg aagggctggg atggcagtag acttggcttt cccattactc    66120
ttttctccag gaaaacatgg ctggcaaggg cttctccttc tgggtctggc tggacaatat    66180
cattgacctt gtgaaaaagt acatcctggc cctttggaac gaagggtagg ttggacagag    66240
tgtgcacaga tgtaaccaag tcccctgctc tcagcaagcc agtggcaggg gatggatgcc    66300
ctgttagcaa taacaacatt gttcctcctc cttggctcca ggtacatcat gggctttatc    66360
agtaaggagc gggagcgggc catcttgagc actaagcctc caggcacctt cctgctaaga    66420
ttcagtgaaa gcagcaaaga aggaggcgtc actttcactt gggtggagaa ggacatcagc    66480
ggtaagggag gctcccaccc accccacctg ctggtggctg ctgaggcctc atcactgctt    66540
ctagttgcaa gcacctactg ccccctggtg ggtggagatg gccttgactc cctgtttcac    66600
tcagactcgc aaaacacatt tgcgtgactt ctaaatcctt ccagctgaag gattggtttg    66660
cttttgtttg cttgctccag tgactatttg ttgagaattt tgcaatttaa attgtattct    66720
tcatctcttt ttctacttaa ccctgttaat atatcttacg caagtagtta tattcaagtt    66780
tattttctat gacccaacta gtagcctctt cttaattaga agccagcctg aatatttcca    66840
cagtgccagg ccactgaaca gggtgttcag ggtctcaaca ctagggtggc ttaagtcttt    66900 tcccctttcga ggaaagaaaa aatgggcagt tttctctgag atgacctagc tgtaggttcc    66960
atgatctttc cttcccatgt cctgtgacag gtaagaccca gatccagtcc gtggaaccat    67020
acacaaagca gcagctgaac aacatgtcat ttgctgaaat catcatgggc tataagatca    67080
tggatgctac caatatcctg gtgtctccac tggtctatct ctatcctgac attcccaagg    67140
aggaggcatt cggaaagtat tgtcggccag agagccagga gcatcctgaa gctgacccag    67200
gtagttgttg attttccatg ttcctggcat ttaattttttg ggaaaagttg gaaattttgg    67260
gatccttgga ggatagatag gcaaatgcct gaataacctg ggggataatt atttctcctt    67320
atgggaaaga attgtagtga gtgcttttgt tggggtgacc gatgggattt gagaggagaa    67380
tcagaatcac ttagagtagt gtagttcctg ctccacagag agtgcatgag tctaaagagg    67440
ggatacagcc tgggcaatat ggtgaaacct cgtctctaca aaaatccaa aaaaattacc    67500 cggtgtggtg gcacgcattt gtagtcgtag ctacttggga ggctgaggtg ggaggatcac    67560
ctgagccaag gagttcaagg ctgtagtgag cggtgatcat gccaccgcac tccagcctgg    67620
ctgatagagt gagatactgt gtcaaaaaat aaaaataaag aggggatcaa tacacatacg    67680
tcccccaaaa catgcctgaa acacgagaag ggaaagtgag ggcagttaac aggatgccct    67740
gctggcacag tgcttcttag tagatgctag aaggtttgag gcccagattt cagcccagca    67800
tatggctttt tgcctgtaac tgaaccatgt cagtgtgcca gatggtctga agaaagggtt    67860
tctggaggaa attattatta gctgcatggg agtatggttt acactagagt agaagagctg    67920
ggagcatcac gtttgaaggg gaagacagtg actgggtgga ggggcaaggg attagtattt    67980
```

```
agagtgtgca actattgaaa ataaggtata ttttaatgtg taagaggaca tgtacttata    68040
tgttatatat aaattatttt agctgggtga agtggctcat gcctatagtc ctagcacttt    68100
gggaggccca ggcgggagga tcacttgagc ctgggagttt gagaacagcc tagacaacat    68160
agtgagaccc tatctataca aaataatttt tttttaaatt agccacgtgt ggtggtttgt    68220
gcctgtagtc ctagctactc gggaggctga ggtgggagga ttgcttaagc ccaggaggtt    68280
gaggctgcag tgagccatga tcgcaccact gcactccagc ctgggtgaca gagcaagacc    68340
ttgactcacc aaaaaaaaaa aaaaaaaaa gagagagaaa ttaaaaatac tgtaatctca    68400
gctgggcatg ggggttcaca cctgcagtcc tagcactttg ggaggctgaa gcaggaggat    68460
cacttgaggc caggaactca agaccagcct ggcaacatag caagaccccca ctacacacac    68520 acacacacac acacacaaag aagagaaaga aaaaacgaa acaaaactgt aatctctgca    68580
gctgtcctca gtgtggaggg ggtagccctg tctgttcccc ttcagcactt gctgttttga    68640
ctctctgggt tctttgtgca ggtcttgatg gggagtctct ggtttgccat tctttgtttg    68700
atttaacttt ctgtaatcat aaagccaatg atgggctttt tttttttttt tttttttaga    68760
ctaagtcttg ctctatcacc caagctggag tgcagtggca ccatctcggc tcactgcaac    68820
ctccacctcc cggttcaagc aattctcctg cctcagcctc ccgagtagct gggattatgg    68880
gcttgtgcca ccatgcccag ctgattttg tattttttgt agagaaaggg tttcgccatg    68940
ttggccaggc tggcctcgaa ctcctgacct caggtgatct gcccacttca gcctcccaaa    69000
gtgctgggat tacaggcgtg agccactgtg cctggcctaa tgatgggctc tttaatgtga    69060
tcctttaggg ttggcgcctt gccctagttg ctgttgaaaa aactatttt gtccaaatag     69120 cacacacaca gaaacctacc aacttccctc ccacttttc ctaggaattc cttctgaggg    69180
atttcttgag atggggcaga atgggcttg gaagagggag ttggagctaa ttgaccgttg    69240
cctttctcct ttgttggggt cctgagtctt gttcctgctg taagagttac tcacttcctg    69300
tctgccacct atctcccttt gcatgtgtgc ttcagttggg agatctgttt atcagcccct    69360
gccacacggc tctttgttcc ttctgcagag gacgttgggg tcccacggct ggtccttttg    69420
actcattttg ctttcaaggt cccacctccc agtctgaggc tgcatcctcc attaccatcg    69480
cccttcctgt gggctgggag gccaggtcct ttcctgccca gcgatgtcag cgtttcctca    69540
ggggccaggc actcatcagg agaaaggaac taattacttg agtaatttgc cttgccttgc    69600
tgagaggagt gtgccctgag ggactccatg tgagtgtggt gacgggtgtg ggggtgtccc    69660
tgtgttattt aaaatgggt gccttcagga cgatgagcat gtgaccattt cctctctatt    69720
tccatcacaa gagtattatg gtatgagggt ctcaggttag attatcctcc caagactctt    69780
ctctcttcct tctctactgg aagcccacat agcatttcct tatggcttga gggagaggtt    69840
cggagccact acaaattag ataaagtaca tttacaatct tgtacaaagc cacacaatga    69900
agtcattttt ctcagctttt ttttttttt tttttttt tttgagcctg agtctcgctc    69960
tatcgtccag actggagtgc agtggcgcga tcttgcttca ctgaaacctc tgcctcccag    70020
gttcaagaga ttctcatacc tcagcctcct gagtagctgg gattacagac atgcaccact    70080
atgcctggct aattttttgga tttttagtag agaccgggtt tcaccctgtt ggccaggctg    70140
gtctcgaacc cctgacctca agtgatcttc ccgcctgggc ctcccaaagt gctgggatta    70200
taggtgtgag ccacagtgcc cagccttgtt tttgtttttg ttttgtttg acagtctgtc    70260 actctgtcac ccaggctgga gtgcagtggt gcgatctcac ctcacttcag cctctgcctc    70320
```

| | |
|---|---|
| ccaggttcaa gtgattctcc tgtctcagcc tcctgagtag ctgggattac aggcgtgcca | 70380 |
| ccacgcccag ctattttgt aatttcatta aagacagggt ttccccatgt tggtgaggct | 70440 |
| ggtcttgaac tcctggcctc aagtgatcca cctgcttcag cctcccaaag tgcagggatt | 70500 |
| acaggcatga gccactgtgc ctggcctcag ctatcttgaa tgctggagaa ttaaatcctt | 70560 |
| ttctgtctag ggtgtcagct ccctaagggc tgggccaaaa cagttggatt tataagacac | 70620 |
| tagagtcttg cctcagtagc tcctttgaat tctgcactga attgatcagt ttcttggccc | 70680 |
| aaagtaaact cagatggcag cccaagagcc actctgcagt gccttctttc acatggtcat | 70740 |
| catgctctct gatccctcag gttctgtcta agcctcatgt tttatgaccg tgctgttctc | 70800 |
| agcccacctc accctgcccc atgccttctc aatggtttgt tcacctgaat tccccagatt | 70860 |
| tcatgccagt atccccaagg ttccttgacc tcttggtgta agcattcagc atctaaaatt | 70920 |
| cattttattc ccgtcaacgc atttctaact gtagaacaag aattataaat gacaaagctc | 70980 |
| atagaaaatt ggcaccttgt cttcccctc cctcttattt tatacataaa agagaatatg | 71040 |
| ggctgggcat tgtggccaag gctgggcatg atagctcata cttgtaatcc agcactttgg | 71100 |
| gagggtgagg cagatggatc acctgaggtc aggagttcaa gaccagcctg gccaacatgg | 71160 |
| tgaaacctca tctctactaa aattacaaaa aaaaaattag ctaggcatgg tggcagatgc | 71220 |
| ctgtaatcca gctactcagg aggctgatga aggagaatca cttgaaccct ggaggcagag | 71280 |
| gttgtagaga gccaagatgg cgctactgca ctccaacctg ggcgaaagag agcaagactc | 71340 |
| cgtctcaaaa aaaaaaaga caaaaattag ccaggcatgg tggtgccacc tgtagtccca | 71400 |
| gctgcttggg agcctaaggc aggagaatcg ttttgacctg ggagtaggag gttgcggtaa | 71460 |
| ccgagattgt gccactgcac ttgagcctgg gcaacagagt gagactctgt ctcaaaacaa | 71520 |
| taagaacaac agcaacaaaa gagagagacc atgccttgct ccaggtctct tagctattga | 71580 |
| agatgtacct ggacccaggt ctccggtctt ctagttgaag caattgtact gccttacaaa | 71640 |
| gtcacattct ctttggtgct ttttgattga cgtatttatc caactagaaa gttactcatg | 71700 |
| ccctcatcca aaaatgtggt agaggccaga ttagtgctgg taggaataag agatataacc | 71760 |
| tttggctttg gaaccacaag cattagcagt ctccatgttc tttaaagact tggtgatatt | 71820 |
| ggtatttagg ctggacacca tgcaaagact acacaggctc ggttcctgca tgcagagaag | 71880 |
| ttatctaaga gatatgacca ggccggaata gaatgctcag accacgtgga ggctgttaaa | 71940 |
| cttttacata atctagggaa agaagggaca caaggtggca ttagtctagg gtcaggtggg | 72000 |
| aaaaggttat gctgaaaagt ctctgcagct caggacagtt ttgtgcaaag aactgaagtt | 72060 |
| cacagctgct agtgcctggg agatcaaata gtataaatga gggcagacaa ccctgagggg | 72120 |
| cagatggagc tttccagaca atcttggcat gaggatgagt gagtttcaaa tcagtcctgc | 72180 |
| cgaggcagat ggcttcctcc agctctgctt actgaatgcg aagtcacagt cagtaagaaa | 72240 |
| actggttttc ttcttcccag gcgctgcccc atacctgaag accaagttta tctgtgtgac | 72300 |
| accgtaagtg gcttcctttc cccgttttgc cttcatttct aatatcctca gttatccctg | 72360 |
| ggaatgggac actgggtgag agttaatctg ccaaaggttg gaagcccctg ggctatgttt | 72420 |
| agtactcaaa gtgaccttgt gtgtttaaaa agcttgagct tttattttc tgttggagac | 72480 |
| cagagtttga tggcttgtgt gtgtgtgttt tgttcttttt ttttttcca ttgtgtcttg | 72540 |
| tcaacccccc gtttccctc ctgctgcccc ccatttccta cagaacgacc tgcagcaata | 72600 |
| ccattgacct gccgatgtcc ccccgcactt tagattcatt gatgcagttt ggaaataatg | 72660 |
| gtgaaggtgc tgaaccctca gcaggagggc agtttggtga gtatttggtt gacagacttt | 72720 |

```
gtccctataa gggaagttgg tcccctttgt gtgatgctct cacatgtaca caccgagagc   72780
tggtcactcg gaatggtagg agattctaga gctttgcttt ccaaaagaga tggtatgaat   72840
gccacatgtg tgagtataaa tcttctagca gccacactgg aaatagacga acttaatttt   72900
tacaatatat tttatttaac ccactaaatc aacatactc tcaatttaac atttcagaaa    72960
aagttgaggc tgggtgagtg gctcatgcct gtaatcccag cactttggga ggccgaggtg   73020
ggtggatcac ttgaggtcag gagttcgaga ccagtctgac caaaatctct aaaatataaa   73080
aattagctgg gcatggtggc gcatacctgt aatcccagct actcaagaag ctgaggtggg   73140
aggatcgctt gagcctggga ggtggaggtt gcagtgagca gagatcgtgc cactgcactc   73200
cagcctgggc gacagagtga gactccatct caaataaaca aaactaaact aaaaagaaaa   73260
agttgagacc ttttttttatt ctttttttc atactaagcc tttaaaatcc agtgggcttt   73320
tgacagccac agcacagctc agtttggaca aaccaaatct caaatgcttg gtggccacgt   73380
gtgtctcggg gctcctgaat taaacagtag atcaagggca aagatctca ggacagcctt    73440 agagcttctg taaacatgga gctctgggaa tcagttaagg tgggaatgag aaaggacct    73500 tcccgaggca gggtcctcca gggaggaggg taaatctggc ttttctgacc atccctgggc   73560 cttaagggc aggagattgg atagcagtgg tagcctgggc cctgtcctct gaagggctgg    73620
gggcgtggcc tgccagttgc agagggtgga caactgaact agttttccct gtctgtccct   73680
ccagagtccc tcacctttga catggagttg acctcggagt gcgctacctc ccccatgtga   73740
ggagctgaga acggaagctg cagaaagata cgactgaggc gcctacctgc attctgccac   73800
ccctcacaca gccaaacccc agatcatctg aaactactaa ctttgtggtt ccagattttt   73860
tttaatctcc tacttctgct atctttgagc aatctgggca cttttaaaaa tagagaaatg   73920
agtgaatgtg ggtgatctgc ttttatctaa atgcaaataa ggatgtgttc tctgagaccc   73980
atgatcaggg gatgtggcgg ggggtggcta gaggagaaa aaggaaatgt cttgtgttgt    74040
tttgttcccc tgccctcctt tctcagcagc tttttgttat tgttgttgtt gttcttagac   74100
aagtgcctcc tggtgcctgc ggcatccttc tgcctgtttc tgtaagcaaa tgccacaggc   74160
cacctatagc tacatactcc tggcattgca cttttttaacc ttgctgacat ccaaatagaa   74220
gataggacta tctaagccct aggtttcttt ttaaattaag aaataataac aattaagggg   74280
caaaaaacac tgtatcagca tagcctttct gtatttaaga aacttaagca gccgggcatg   74340
gtggctcacg cctgtaatcc cagcactttg ggaggccgag gcggatcata aggtcaggag   74400
atcaagacca tcctggctaa cacggtgaaa ccccgtctct actaaaagta caaaaaatta   74460
gctgggtgtg gtggtgggcg cctgtagtcc cagctactcg ggaggctgag gcaggagaat   74520
cgcttgaacc tgagaggcgg aggttgcagt gagccaaaat tgcaccactg cacactgcac   74580
tccatcctgg gcgacagtct gagactctgt ctcaaaaaaa aaaaaaaaa aaagaaactt    74640 cagttaacag cctccttggt gctttaagca ttcagcttcc ttcaggctgg taatttatat   74700
aatccctgaa acgggcttca ggtcaaaccc ttaagacatc tgaagctgca acctggcctt   74760
tggtgttgaa ataggaaggt ttaaggagaa tctaagcatt ttagactttt ttttataaat   74820
agacttattt tcctttgtaa tgtattggcc ttttagtgag taaggctggg cagagggtgc   74880
ttacaacctt gactcccttt ctccctggac ttgatctgct gtttcagagg ctaggttgtt   74940
tctgtgggtg cctatcagg gctgggatac ttctgattct ggcttccttc ctgccccacc    75000
ctcccgaccc cagtcccct gatcctgcta gaggcatgtc tccttgcgtg tctaaaggtc    75060
```

```
cctcatcctg tttgttttag gaatcctggt ctcaggacct catggaagaa gaggggggaga    75120 gagttacagg ttggacatga tgcacactat ggggccccag cgacgtgtct ggttgagctc    75180
agggaatatg gttcttagcc agtttcttgg tgatatccag tggcacttgt aatggcgtct    75240
tcattcagtt catgcagggc aaaggcttac tgataaactt gagtctgccc tcgtatgagg    75300
gtgtatacct ggcctccctc tgaggctggt gactcctccc tgctgggggcc ccacaggtga    75360 ggcagaacag ctagagggcc tccccgcctg cccgccttgg ctggctagct cgcctctcct    75420
gtgcgtatgg gaacacctag cacgtgctgg atgggctgcc tctgactcag aggcatggcc    75480
ggatttggca actcaaaacc accttgcctc agctgatcag agtttctgtg gaattctgtt    75540
tgttaaatca aattagctgg tctctgaatt aaggggggaga cgaccttctc taagatgaac    75600
agggttcgcc ccagtcctcc tgcctggaga cagttgatgt gtcatgcaga gctcttactt    75660
ctccagcaac actcttcagt acataataag cttaactgat aaacagaata tttagaaagg    75720
tgagacttgg gcttaccatt gggtttaaat catagggacc tagggcgagg gttcagggct    75780
tctctggagc agatattgtc aagttcatgg ccttaggtag catgtatctg gtcttaactc    75840
tgattgtagc aaaagttctg agaggagctg agccctgttg tggcccatta aagaacaggg    75900
tcctcaggcc ctgcccgctt cctgtccact gcccccctccc catccccagc ccagccgagg    75960
gaatcccgtg ggttgcttac ctacctataa ggtggtttat aagctgctgt cctggccact    76020
gcattcaaat tccaatgtgt acttcatagt gtaaaaattt atattattgt gaggtttttt    76080 gtctttttttt tttttttttt ttttggtat attgctgtat ctactttaac ttccagaaat    76140
aaacgttata taggaaccgt ctgatagcat ggcagctctg tttggctggt ggaggcttcc    76200
ttttcccctg cataagttct gagggggcct cacacacagg tggggcctgg gataagggcc    76260
ggaaagggtc ttgagaggag gtggttgcct taatcccccc cgccaacccc cttatgttag    76320
ccaccagccc ggaggtaagg ggtgcctgga ggagcaggag gtcaatagtc caacggcaga    76380
aaggtgtcag agtggaggcc tccctccccg gcccccctcct accccccaga gcggcctcgt    76440
cctgtctggg gtcagataag ccacctaagc ggggtggggg gtagatactc ccaccgcacc    76500
aaggcctccc cttccacagt tggctccttt atcactttcc cttcagttca cccagcgggg    76560
acaacacgca gacacccggt ggtggctgca gggccccggg cagccagcgg tgataatgca    76620
gggaaaggcg ccccaacctc agctacgcgg gcgcccacag ggcttctccc cacccctaca    76680
cgtgccccag cgccctggag accgcgcctg ggagctacga gcgagcacct tccctcgcag    76740
agatggatca gattagcccc ctggggcggt ggcacctgcc cgtcccctcc cctcctctct    76800
tctcccaccc ccgccttccc cctgctctgg gccccctgca cctccctctt ggggcccacg    76860 cgccgccccct ctccctcgct tgagctctga gctcagaagg aacctgcccg caaacctggc    76920
tcccagcccc gcccagggag cgcgcgtccc tgagcccaag ggcccagcg acagcaggga    76980 ctggctgcag ccggcagtgc gggggtccag ccggggcgag ccggtcccgc ttgctgcacc    77040
tccgcctcgc acagtcgccg gcagccagct gaaaacagcg cagccgcgtg gtgccacctg    77100
ctggtctctg ggaaggagga ggatgggacg gttgttgcgg ctctgggact gccctgggcc    77160
ccgagggttg agaagcatct tggcgccggg ccctcagccg ccagcttcga ggctgctggg    77220
agcagcagct gctaaggaga agcctgggtc agagttctgc ccacccgcgc ccatctccat    77280
catttcccca aacctcgagt ccctgctttt ttaaggaatc tgtgcccct aaactggctc    77340 cttacccttc tgagaagcat tgacagtatt ccaggggtgg ccagcaccct gaaaaccaca    77400
gcaaagcggg cagagttaaa atttaagact aaaaatgaca gcatcaggca tgcacgcggg    77460
```

```
aaggaacaga acaaccagct ccaggggttc ccatcaccca gggaggccac caacgcccca   77520
accaggagcc atagcagcaa atttatgaaa aaaatatttt attccaaaac actgtttaca   77580
caaatgtgtg gtctttgtac aaagtacaaa aaaacccctc ttctcatccc cacctccctt   77640
cagagaagtt taaaccttgg gctctcaatc ttccatggtc agctgccoct gactgcgagt   77700 cctacagcct cagagggagg agcgtgtggg gttgggagca aggcctcacc agaacacagc   77760
cagttacgca acagcgcaag gcctgctcca ggccccacct ccagcggagt caaaccagat   77820
cagcttttac ccctcactcc agattccaca ggcacgcagc acatggctga tttgcagctt   77880
gtctttcact gcagttttttt gttttttgttt tttccaggag gcaagaggac caaccctcca   77940
agtcccgggg cccctgtcca cccaccatat cctagaccca atcttttcta cctctttgtc   78000
gacaaggtta caaacagaga ggcaagcaaa gaaggctggg gcccaacgga ggggagagaa   78060
tatatatccc gggaaacgtg ggcaacagca tcatagactt gaatgaagcc caaggccaag   78120
cagccaagca aggactaatt cagagcagct cagaaaccct cactcaaacc ggcggccccc   78180
ctgtgctaag gacatggccg ggcccagacg cgctctcata gggttcacag agagtctgga   78240
gtccacgttc actaaagtat aaaatactac tcgaaaatga accccagcct cccttctgag   78300
agatgaatcg gttacatcaa cacatgagga cagatgcatt tacatagacc cacacactct   78360
ctctttctct ctctctgtct ctctgtctct ctctcttagg agggcaaagc ttctcactcc   78420
ggagtgaaac ttcagcttac agacgttacc tgtctcccct ccccttctga atcatctcat   78480
tcaaatagct gctgagcaga tgaggggccc aggaggaata ggtctggctg cattgagtgc   78540
ctgcagtgac agaggctcgg tctctaccat gacagagaca gactcggcgc actcttggat   78600
gccatgatct gaaaagaggc caccgctgct gcagccacat cccaggactg cacaggggag   78660
gcaggcgtag ctcatgcaca aggacacaca cacacacaca cacacaagca catgcatgcc   78720
tgcaaaggtg tcagtgtaca cagccttact aaactcacaa cacgaccgct tcacattgca   78780
tattgtttcc aaagagaagc gtgggattca aacattcatg agagggagcc tctggcagag   78840
gtgaaaagac cggcagggggg cgagaggcgg gagtcaagac tgtccattgg tcggcgtaag   78900
agttcctcca cgtgcctggc cacatccatg gtctcatcca ggtcgaattc tccatcctga   78960
tcgagtacat ggtcagggct ggtaaagaca ggggatgtc a                        79001
```

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
actgccgcag ctccat                                                  16

<210> SEQ ID NO 4
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 4
gagattctct acca                                                    14

<210> SEQ ID NO 5

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
agatcttgca tgtctc                                                         16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
ataattcaac tcaggg                                                         16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7 acttttcac aaggtc                                                          16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
ccatgatctt atagcc                                                         16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
gatagcagaa gtagga                                                         16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
caaggttaaa aagtgc                                                         16

<210> SEQ ID NO 11
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 11
```

```
aaggttaaaa agtg                                                          14

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ctatttggat gtcagc                                                        16

<210> SEQ ID NO 13
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 13
tatttggatg tcag                                                          14

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
tagatagtcc tatctt                                                        16

<210> SEQ ID NO 15
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 15
agatagtcct atct                                                          14

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
aagaaaccta gggctt                                                        16

<210> SEQ ID NO 17
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 17
agaaacctag ggct                                                          14

<210> SEQ ID NO 18
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 18
gctgatacag tgtttt                                                        16

<210> SEQ ID NO 19
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 19
ctgatacagt gttt                                                          14

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
atacagaaag gctatg                                                        16

<210> SEQ ID NO 21
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 21
tacagaaagg ctat                                                          14

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gcttaagttt cttaaa                                                        16

<210> SEQ ID NO 23
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 23
cttaagtttc ttaa                                                          14

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
agcaccaagg aggctg                                                        16
```

<210> SEQ ID NO 25
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 25
gcaccaagga ggct                                                         14

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
aagctgaatg cttaaa                                                       16

<210> SEQ ID NO 27
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 27
agctgaatgc ttaa                                                         14

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ttaccagcct gaagga                                                       16

<210> SEQ ID NO 29
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 29
taccagcctg aagg                                                         14

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
cagggattat ataaat                                                       16

<210> SEQ ID NO 31
<211> LENGTH: 14
<212> TYPE: DNA
<213> ORGANISM: Artificial sequence
<220> FEATURE:

<223> OTHER INFORMATION: Synthetic oligonucleotide

<400> SEQUENCE: 31
agggattata taaa                                               14

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
acctgaagcc cgtttc                                             16

<210> SEQ ID NO 33
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 33
cctgaagccc gttt                                               14

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
tgtcttaagg gtttga                                             16

<210> SEQ ID NO 35
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 35
gtcttaaggg tttg                                               14

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
ggttgcagct tcagat                                             16

<210> SEQ ID NO 37
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 37
gttgcagctt caga                                               14

```
<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
tcaacaccaa aggcca                                                    16

<210> SEQ ID NO 39
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 39
caacaccaaa ggcc                                                      14

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
tccttaaacc ttccta                                                    16

<210> SEQ ID NO 41
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 41
ccttaaacct tcct                                                      14

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
aaaatgctta gattct                                                    16

<210> SEQ ID NO 43
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 43
aaatgcttag attc                                                      14

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 44
aaataagtct atttat                                                    16

<210> SEQ ID NO 45
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 45
aataagtcta ttta                                                      14

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ggccaataca ttacaa                                                    16

<210> SEQ ID NO 47
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 47
gccaatacat taca                                                      14

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tgcccagcct tactca                                                    16

<210> SEQ ID NO 49
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 49
gcccagcctt actc                                                      14

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
gttgtaagca ccctct                                                    16

<210> SEQ ID NO 51
<211> LENGTH: 14

<212> TYPE: DNA
<213> ORGANISM: Artificial sequence
<220> FEATURE:
<223> OTHER INFORMATION: Synthetic oligonucleotide

<400> SEQUENCE: 51
ttgtaagcac cctc                                                        14

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
agaaagggag tcaagg                                                      16

<210> SEQ ID NO 53
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 53
gaaagggagt caag                                                        14

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
gcagatcaag tccagg                                                      16

<210> SEQ ID NO 55
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 55
cagatcaagt ccag                                                        14

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
agcctctgaa acagca                                                      16

<210> SEQ ID NO 57
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 57

```
gcctctgaaa cagc                                                       14

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
cccacagaaa caacct                                                     16

<210> SEQ ID NO 59
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 59
ccacagaaac aacc                                                       14

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
agccctgata aggcac                                                     16

<210> SEQ ID NO 61
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 61
gccctgataa ggca                                                       14

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
aatcagaagt atccca                                                     16

<210> SEQ ID NO 63
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 63
atcagaagta tccc                                                       14

<210> SEQ ID NO 64
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 64
gcctctagca ggatca                                                       16

<210> SEQ ID NO 65
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 65
cctctagcag gatc                                                         14

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
cacgcaagga gacatg                                                       16

<210> SEQ ID NO 67
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 67
acgcaaggag acat                                                         14

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
tgagggacct ttagac                                                       16

<210> SEQ ID NO 69
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 69
gagggacctt taga                                                         14

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
caggattcct aaaaca                                                       16
```

```
<210> SEQ ID NO 71
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 71
aggattccta aaac                                                        14

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
atgaggtcct gagacc                                                      16

<210> SEQ ID NO 73
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 73
tgaggtcctg agac                                                        14

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
catcatgtcc aacctg                                                      16

<210> SEQ ID NO 75
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 75
atcatgtcca acct                                                        14

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76 gggcccata gtgtgc                                                       16

<210> SEQ ID NO 77
<211> LENGTH: 14
<212> TYPE: DNA
<213> ORGANISM: Artificial sequence
<220> FEATURE:
<223> OTHER INFORMATION: Synthetic oligonucleotide
```

<400> SEQUENCE: 77
ggccccatag tgtg                                                        14

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
agctcaacca gacacg                                                      16

<210> SEQ ID NO 79
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 79
gctcaaccag acac                                                        14

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
gaaccatatt ccctga                                                      16

<210> SEQ ID NO 81
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 81
aaccatattc cctg                                                        14

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
caagaaactg gctaag                                                      16

<210> SEQ ID NO 83
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 83
aagaaactgg ctaa                                                        14

<210> SEQ ID NO 84

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gccactggat atcacc                                                  16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
aactgaatga agacgc                                                  16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
gcttattatg tactga                                                  16

<210> SEQ ID NO 87
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 87
cttattatgt actg                                                    14

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
gcccaagtct cacctt                                                  16

<210> SEQ ID NO 89
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 89
cccaagtctc acct                                                    14

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
```
cccaatggta agccca                                                16

<210> SEQ ID NO 91
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 91
ccaatggtaa gccc                                                  14

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
aacccaatgg taagcc                                                16

<210> SEQ ID NO 93
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 93
acccaatggt aagc                                                  14

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
taggtcccta tgattt                                                16

<210> SEQ ID NO 95
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 95
aggtccctat gatt                                                  14

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
aagccctgaa ccctcg                                                16

<210> SEQ ID NO 97
<211> LENGTH: 14
<212> TYPE: DNA

```
<213> ORGANISM: Artificial sequence
<220> FEATURE:
<223> OTHER INFORMATION: Synthetic oligonucleotide

<400> SEQUENCE: 97
agccctgaac cctc                                                    14

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
cctaaggcca tgaact                                                  16

<210> SEQ ID NO 99
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 99
ctaaggccat gaac                                                    14

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
accagataca tgctac                                                  16

<210> SEQ ID NO 101
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 101
ccagatacat gcta                                                    14

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
tacaatcaga gttaag                                                  16

<210> SEQ ID NO 103
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 103
acaatcagag ttaa                                                    14
```

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
tcctctcaga actttt                                                   16

<210> SEQ ID NO 105
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 105
cctctcagaa cttt                                                     14

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gctcctctca gaactt                                                   16

<210> SEQ ID NO 107
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 107
ctcctctcag aact                                                     14

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
ttctttaatg ggccac                                                   16

<210> SEQ ID NO 109
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 109
tctttaatgg gcca                                                     14

<210> SEQ ID NO 110
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 110
acgggattcc ctcggc                                                    16

<210> SEQ ID NO 111
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 111
cgggattccc tcgg                                                      14

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
gtaggtaagc aaccca                                                    16

<210> SEQ ID NO 113
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 113
taggtaagca accc                                                      14

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
gaatttgaat gcagtg                                                    16

<210> SEQ ID NO 115
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 115
aatttgaatg cagt                                                      14

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
tgaagtacac attgga                                                    16

```
<210> SEQ ID NO 117
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 117
gaagtacaca ttgg                                                        14

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ataaattttt acacta                                                      16

<210> SEQ ID NO 119
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 119 taaatttta cact                                                         14

<210> SEQ ID NO 120
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 120
caataatata aatt                                                        14

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
ctggaagtta aagtag                                                      16

<210> SEQ ID NO 122
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 122
tggaagttaa agta                                                        14

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 123
gtactctttc agtggt                                                    16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
atgcttagat tctcct                                                    16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
agcagatcaa gtccag                                                    16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
aggtgttccc atacgc                                                    16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
taggtgttcc catacg                                                    16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
ggttcctcct gttggc                                                    16

<210> SEQ ID NO 129
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 129
atgcttagat tctcctt                                                   17
```

CANCER TREATMENT

CROSS-REFERENCE TO RELATED APPLICATIONS

This application is the U.S. National Stage under 35 U.S.C §371 of International Application No. PCT/US2013/067469 filed on 30 Oct. 2013, which claims the benefit of U.S. Provisional Application No. 61/720,939 filed on 31 Oct. 2012, and U.S. Provisional Application No. 61/777,875 filed on 12 Mar. 2013. The entire text of each of the above provisional patent applications is incorporated by reference into this patent.

SEQUENCE LISTING

The present application is being filed along with a Sequence Listing in electronic format. The Sequence Listing is provided as a file entitled BIOL0216USL2SEQ.txt created Mar. 12, 2013, which is 124 kb in size. The information in the electronic format of the sequence listing is incorporated herein by reference in its entirety.

FIELD

In certain embodiments, methods, compounds, and compositions for treating B-cell lymphoma by inhibiting expression of STAT3 mRNA or protein in an animal are provided herein. Such methods, compounds, and compositions are useful to treat, prevent, or ameliorate B-cell lymphoma or hepatocellular carcinoma.

BACKGROUND

The STAT (signal transducers and activators of transcription) family of proteins are DNA-binding proteins that play a dual role in signal transduction and activation of transcription. Presently, there are six distinct members of the STAT family (STAT1, STAT2, STAT3, STAT4, STAT5, and STAT6) and several isoforms (STAT1α, STAT1β, STAT3α and STAT3β). The activities of the STATs are modulated by various cytokines and mitogenic stimuli. Binding of a cytokine to its receptor results in the activation of Janus protein tyrosine kinases (JAKs) associated with these receptors. This phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

The specificity of STAT activation is due to specific cytokines, i.e., each STAT is responsive to a small number of specific cytokines. Other non-cytokine signaling molecules, such as growth factors, have also been found to activate STATs. Binding of these factors to a cell surface receptor associated with protein tyrosine kinase also results in phosphorylation of STAT.

STAT3 (also acute phase response factor (APRF)), in particular, has been found to be responsive to interleukin-6 (IL-6) as well as epidermal growth factor (EGF) (Darnell, Jr., J. E., et al., Science, 1994, 264, 1415-1421). In addition, STAT3 has been found to have an important role in signal transduction by interferons (Yang, C.-H., et al., Proc. Natl. Acad. Sci. USA, 1998, 95, 5568-5572). Evidence exists suggesting that STAT3 may be regulated by the MAPK pathway. ERK2 induces serine phosphorylation and also associates with STAT3 (Jain, N., et al., Oncogene, 1998, 17, 3157-3167).

STAT3 is expressed in most cell types (Zhong, Z., et al., Proc. Natl. Acad. Sci. USA, 1994, 91, 4806-4810). It induces the expression of genes involved in response to tissue injury and inflammation. STAT3 has also been shown to prevent apoptosis through the expression of bcl-2 (Fukada, T., et al., Immunity, 1996, 5, 449-460).

Recently, STAT3 was detected in the mitochondria of transformed cells, and was shown to facilitate glycolytic and oxidative phosphorylation activities similar to that of cancer cells (Gough, D. J., et al., Science, 2009, 324, 1713-1716). The inhibition of STAT3 in the mitochondria impaired malignant transformation by activated Ras. The data confirms a Ras-mediated transformation function for STAT3 in the mitochondria in addition to its nuclear roles.

Aberrant expression of or constitutive expression of STAT3 is associated with a number of disease processes.

SUMMARY

B-cell lymphoma is a B-lymphocyte blood cell cancer that is clinically classified as either Hodgkin's lymphoma or non-Hodgkin's lymphoma. There are several types of non-Hodgkin's lymphoma, of which diffuse large B-cell lymphoma (DLBCL) is the most common type, accounting for approximately 30 percent of all lymphomas. In the United States, DLBCL affects about 7 out of 100,000 people each year.

Several embodiments provided herein relate to the discovery that inhibiting the JAK-STAT signaling pathway can be useful for treating B-cell lymphoma. In certain embodiments, antisense compounds targeting STAT3 are useful for treating B-cell lymphoma, such as DLBCL, at unexpectedly low doses for an antisense compound as a cancer therapeutic. In several embodiments, antisense compounds targeting STAT3 provided herein are administered to a subject having B-cell lymphoma at a fixed total weekly dose in the range of about 15-750 mg. In certain embodiments, antisense compounds targeting STAT3 provided herein are administered to a subject having B-cell lymphoma in the range of about 0.2 to 3.5 milligrams of the antisense compound per kilogram of the subject's body weight per week (0.2-3.5 mg/kg/wk). Such dose ranges are unexpectedly low for treating cancer. By comparison, a Phase 1 study of LY2275796, an antisense oligonucleotide targeted to cap-binding protein eukaryotic initiation factor 4E (eIF-4E), concluded that the maximum tolerable dose (MTD) and biologically effective dose (BED) of LY2275796 is 1,000 mg under a loading and maintenance dose regimen, but even at a 1,000 mg dose, no tumor response was observed. (Hong D. S. et al., Clin Cancer Res. 2011 17(20):6582-91).

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of the term "or" means "and/or", unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-deoxynucleoside" means a nucleoside comprising 2'-H furanosyl sugar moiety, as found naturally occurring in deoxyribonucleosides (DNA). In certain embodiments, a 2'-deoxynucleoside may comprise a modified nucleobase or may comprise an RNA nucleobase (e.g., uracil).

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position other than H or OH. Unless otherwise indicated, a 2'-substituted nucleoside is not a bicyclic nucleoside.

"5'-methylcytosine" means a cytosine modified with a methyl group attached to the 5' position. A 5-methylcytosine is a modified nucleobase.

"About" as applied to dosing amounts means within ±12% of a value. For example, if it is stated, "the dose is an amount in the range of about 15-750 mg," it is implied that the dose is an amount in the range of 13-840 mg. In another example, if it is stated that the dose is an amount of "about 50 mg," it is implied that the dose can be from 44 mg to 56 mg. "About" as applied to activity levels means within ±10% of a value. For example, if it is stated, "the compounds affected at least about 70% inhibition of STAT3", it is implied that the STAT3 levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to STAT3 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, and shRNAs.

"Antisense inhibition" means reduction of target nucleic acid levels or target protein levels in the presence of an antisense compound complementary to a target nucleic acid as compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month. In certain embodiments, single dose means administration of one dose, and only one dose, to a subject.

"Dosage unit" means a form in which a pharmaceutical agent is provided. In certain embodiments, a dosage unit is a vial containing lyophilized ISIS 481464. In certain embodiments, a dosage unit is a vial containing reconstituted ISIS 481464.

"Dosing regimen" is a combination of doses designed to achieve one or more desired effects. In certain embodiments, a dose regimen is designed to provide a therapeutic effect quickly.

"Duration" means the period of time during which an activity or event continues. For example, the duration of a loading phase is the period of time during which loading doses are administered. For example, the duration of the maintenance phase is the period of time during which maintenance doses are administered.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"First phase" means a dosing phase during which administration is initiated and steady state concentrations of pharmaceutical agents can be, but is not necessarily, achieved in a target tissue. "Second phase" means a dosing phase after the "first phase." In certain embodiments, the dose or total weekly dose of the first phase and the second phase are different.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"HCC" means hepatocellular carcinoma. It is the most common form of liver cancer and also referred to as malignant hepatoma.

"Hybridization" means the annealing of complementary nucleic acid molecules. In certain embodiments, complementary nucleic acid molecules include an antisense compound and a target nucleic acid.

"Hyperproliferative disease" means a disease characterized by rapid or excessive growth and reproduction of cells. Examples of hyperproliferative diseases include cancer, e.g., carcinomas, sarcomas, lymphomas, and leukemias as well as associated malignancies and metastases.

"Identifying an animal at risk for hyperproliferative disease" means identifying an animal having been diagnosed with a hyperproliferative disease or identifying an animal predisposed to develop a hyperproliferative disease. Individuals predisposed to develop a hyperproliferative disease include those having one or more risk factors for hyperproliferative disease including older age; history of other hyperproliferative diseases; history of tobacco use; history of exposure to sunlight and/or ionizing radiation; prior contact with certain chemicals, especially continuous contact; past or current infection with certain viruses and bacteria; prior or current use of certain hormone therapies; genetic predisposition; alcohol use; and certain lifestyle choices including poor diet, lack of physical activity, and/or being overweight. Such identification may be accomplished by any method including evaluating an individual's medical history and standard clinical tests or assessments.

"Immediately adjacent" means there are no intervening elements between the immediately adjacent elements.

"Inhibiting STAT3" means reducing expression of STAT3 mRNA and/or protein levels in the presence of a STAT3 antisense compound, including a STAT3 antisense oligonucleotide, as compared to expression of STAT3 mRNA and/or protein levels in the absence of a STAT3 antisense compound, such as an antisense oligonucleotide.

"Individual" means a human or non-human animal selected for treatment or therapy.

"Internucleoside linkage" refers to the chemical bond between nucleosides.

"ISIS 481464" means a STAT3 antisense oligonucleotide having the nucleobase sequence "CTATTTGGATGTCAGC", incorporated herein as SEQ ID NO: 12, where each internucleoside linkage is a phosphorothioate internucleoside linkage, each cytosine is a 5-methylcytosine, and each of nucleosides 1-3 and 14-16 comprise a cEt moeity. ISIS 481464 is complementary to nucleobases 3016-3031 of the sequence of GENBANK Accession No. NM_139276.2, incorporated herein as SEQ ID NO:1.

"Linked nucleosides" means adjacent nucleosides which are bonded together.

"Loading phase" means a dosing phase during which administration is initiated and steady state concentrations of pharmaceutical agents are achieved in a target tissue. For example, a loading phase is a dosing phase during which steady state concentrations of antisense oligonucleotide are achieved in liver.

"Maintenance phase" means a dosing phase after target tissue steady state concentrations of pharmaceutical agents have been achieved. For example, a maintenance phase is a dosing phase after which steady state concentrations of antisense oligonucleotide are achieved in liver.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, and/or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution. In certain embodiments, a pharmaceutical composition shows activity in free uptake assay in certain cell lines.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i e, linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Signal Transducer and Activator of Transcription 3 nucleic acid" or "STAT3 nucleic acid" means any nucleic acid encoding STAT3. For example, in certain embodiments, a STAT3 nucleic acid includes a DNA sequence encoding STAT3, an RNA sequence transcribed from DNA encoding STAT3 (including genomic DNA comprising introns and exons), and an mRNA sequence encoding STAT3. "STAT3 mRNA" means an mRNA encoding a STAT3 protein.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Subject" means a human selected for treatment or therapy.

"Targeting" or "targeted" means the process of design and selection of an antisense compound that will specifically hybridize to a target nucleic acid and induce a desired effect.

"Target nucleic acid," "target RNA," "target mRNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

In certain aspects, there is provided a method of treating cancer in a subject which comprises administering to the subject an inhibitor of the JAK-STAT pathway. In certain embodiments the cancer is B-cell lymphoma or hepatocellular carcinoma (HCC).

In certain aspects, there is provided a method of treating B-cell lymphoma in a subject which comprises administering to the subject an inhibitor of the JAK-STAT pathway.

In certain aspects, there is provided a method of treating cancer, such as B-cell lymphoma or HCC, in a subject which comprises administering to the subject a weekly dose of an antisense compound complementary to a nucleic acid encoding human STAT3, wherein the dose comprises about 0.2 to 3.5 milligrams of the antisense compound per kilogram of the subject's body weight per week (0.2-3.5 mg/kg/wk). In certain embodiments, the dose is about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose comprises about 1.5 to 3.5 milligrams of the antisense compound per kilogram of the subject's body weight (1.5-3.5 mg/kg/wk. In certain embodiments, the dose is 2.0 milligrams of the antisense compound per kilogram of the subject's body weight per week (2.0 mg/kg/wk). In certain embodiments, the dose is effective to treat cancer and acceptably tolerable. The dose can be administered for at least 1-52 weeks, at least 1-10 weeks, at least 1-7 weeks, at least 1-5 weeks, at least 5 weeks, at least 6 weeks, or at least 7 weeks. In certain embodiments, the dose can be administered to the subject 1, 2, 3, 4, 5, 6, or 7 times per week. In certain embodiments, the dose is administered to the subject 1-6 times per week. In several embodiments, the dose can be administered 6 times during the first week and 1 time each subsequent week. In certain embodiments, the subject's body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a single dose of a pharmaceutical composition comprising an antisense compound complementary to a nucleic acid encoding human STAT3, wherein the single dose comprises an amount of the compound in the range of about 15-250 mg. In certain embodiments, the single dose comprises an amount of the compound in the range of about 100-250 mg. In certain embodiments, the single dose is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the dose is effective to treat cancer and acceptably tolerable.

In certain embodiments, a method comprises administering to a subject having cancer, such as B-cell lymphoma or HCC, a total weekly dose of a pharmaceutical composition comprising an antisense compound complementary to a nucleic acid encoding human STAT3, wherein the total weekly dose comprises an amount of the compound in the range of about 15-750 mg weekly. In certain embodiments, the total weekly dose comprises an amount of the compound in the range of about 100-750 mg weekly. In certain embodiments, the total weekly dose is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In certain embodiments, the dose is effective to treat cancer and acceptably tolerable. The total weekly dose can be administered in 2, 3, 4, 5, 6, or 7 equal doses within a week, such that the total weekly dose does not exceed about 750 mg. In certain embodiments, the total weekly dose is administered in 3 equal doses within a week. It will be understood that the aforementioned total weekly dose ranges can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann Pharmacol. 2000. 34: 1066-1069): for men (in kg)=50+2.3 kg/inch over 5 feet; for women (in kg)=45.5+2.3 kg/inch over 5 feet.

In certain aspects, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase comprising a total weekly dose in the range of about 15-750 mg for the first 1-10 weeks, and a maintenance phase comprising a total weekly dose in the range of 15-250 mg for at least 1 week after the loading phase.

In certain embodiments, the loading phase is 1 week, 2 weeks, 3 weeks, 4 weeks, or 5 weeks. In certain embodiments, the loading phase comprises administering the compound in 2, 3, 4, 5, 6, or 7 equal doses within a week. In certain embodiments, the loading phase comprises administering the compound in 3 equal doses within a week. In several embodiments, the total weekly dose of the antisense compound in the loading phase is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned total weekly dose ranges in the loading phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose in the loading phase by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose in the loading phase can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the maintenance phase comprises administering the compound in 2, 3, 4, 5, 6, or 7 equal doses within a week. In several embodiments, the total weekly dose of the antisense compound in the maintenance phase is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the total weekly dose in the maintenance phase is administered as a single dose per week. It will be understood that the aforementioned total weekly dose ranges in the maintenance phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose in the maintenance phase can be represented as an amount of about 15 mg/70 kg (0.2 mg/kg/wk) to 250 mg/70 kg (3.6 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase about 6, 7, 8, 9, or 10 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma, a pharmaceutical composition comprising an antisense compound complementary to a nucleic acid encoding human STAT3, wherein administering the antisense compound comprises:

a loading phase comprising a dose in the range of about 3 to 4 mg/kg/wk for about 6, 7, 8, 9, or 10 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase comprising a dose of about 3 mg/kg/wk for about 8 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a total weekly dose in the range of about 15-750 mg for the first 1-10 weeks, and a second phase comprising a total weekly dose in the range of 15-250 mg for at least 1 week after the loading phase.

In certain embodiments, the first phase is 1 week, 2 weeks, 3 weeks, 4 weeks, or 5 weeks. In certain embodiments, the first phase comprises administering the compound in 2, 3, 4, 5, 6, or 7 equal doses within a week. In certain embodiments, the first phase comprises administering the compound in 3 equal doses within a week. In several embodiments, the total weekly dose of the antisense compound in the first phase is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned total weekly dose ranges in the first phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose in the first phase by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose in the first phase can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the second phase comprises administering the compound in 2, 3, 4, 5, 6, or 7 equal doses within a week. In several embodiments, the total weekly dose of the antisense compound in the second phase is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the total weekly dose in the second phase is administered as a single dose per week. It will be understood that the aforementioned total weekly dose ranges in the second phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose in the second phase can be represented as an amount of about 15 mg/70 kg (0.2 mg/kg/wk) to 250 mg/70 kg (3.6 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase for about 6, 7, 8, 9, or 10 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a dose in the range of about 3 to 4 mg/kg/wk for about 6, 7, 8, 9, or 10 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a dose of about 3 mg/kg/wk for about 8 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In any of the above embodiments, the B-cell lymphoma is a non-Hodgkin's B-cell lymphoma. Examples of non-Hodgkin's B-cell lymphoma of certain aspects include, but are not limited to, diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the non-Hodgkin's B-cell lymphoma is diffuse large B cell lymphoma (DLBCL).

In any of the above embodiments, the B-cell lymphoma is Hodgkin's B-cell lymphoma.

In any of the foregoing embodiments, administering the dose of the antisense compound reduces tumor size or tumor volume in the subject. In certain embodiments, administering the dose of the antisense compound prolongs survival of the subject. In certain embodiments, administering the dose of the antisense compound treats cancer, such as B-cell lymphoma, in the subject. In any of the above embodiments, the method is effective to treat cancer and acceptably tolerable in a subject.

In certain of the foregoing embodiments, the subject is identified as having cancer, such as B-cell lymphoma, prior to administering the antisense compound to the subject. In certain embodiments, the subject identified as having cancer, such as B-cell lymphoma, received or is currently receiving anti-cancer treatment, such as a first-line treatment regimen. For example, in certain embodiments the first-line treatment regimen is a combination of cyclophosphamide, hydroxydaunorubicin, oncovin (vincristine), prednisone or prednisolone (CHOP). In certain embodiments, the first-line treatment regimen is a combination of rituximab and CHOP (R-CHOP). In certain embodiments, the subject is refractory to a first-line treatment regimen such as CHOP and/or R-CHOP.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 3008 to 3033 of SEQ ID NO: 1, wherein the nucleobase sequence is complementary to SEQ ID NO: 1.

In any of the foregoing embodiment, the antisense compound comprises a modified oligonucleotide consisting of 12 to 30 linked nucleosides having a nucleobase sequence comprising a portion of at least 12 contiguous nucleobases complementary to an equal length portion of nucleobases 3016 to 3031 of SEQ ID NO: 1, wherein the nucleobase sequence is complementary to SEQ ID NO: 1.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 6476 to 6491 of SEQ ID NO: 2, wherein the nucleobase sequence is complementary to SEQ ID NO: 2.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 250-286; 250-285; 264-285; 264-282; 728-745; 729-745; 729-744; 787-803; 867-883; 955-978; 1146-1170; 1896-1920; 1899-1920; 1899-1919; 1899-1918; 1899-1916; 1901-1916; 1946-1963; 1947-1963; 2155-2205; 2155-2187; 2156-2179; 2204-2221; 2681-2696; 2699-2716; 3001-3033; 3008-3033, 3010-3033, 3010-3032, 3015-3033, 3015-3032, 3015-3031; 3016-3033; 3016-3032; 3016-3033; 3452-3499; 3460-3476; 3583-3608; 3591-3616; 3595-3615; 3595-3614; 3595-3612; 3675-3706; 3713-3790; 3715-3735; 3833-3878; 3889-3932; 3977-4012; 4067-4100; 4225-4256; 4234-4252; 4235-4252; 4235-4251; 4236-4252; 4306-4341; 4431-4456; 4439-4454; 4471-4510; 4488-4505; 4530-4558; 4539-4572; 4541-4558; 4636-4801; 4782-4796; 4800-4823; 4811-4847; 4813-4859; 4813-4815; 4813-4831; 4827-4859; 4827-4844; or 4842-4859 of SEQ ID NO: 1, wherein the nucleobase sequence of the modified oligonucleotide is complementary to SEQ ID NO: 1.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 2668-2688; 2703-2720; 5000-5021; 5001-5017; 5697-5722; 5699-5716; 6475-6490; 6475-6491; 6476-6491; 7682-7705; 8078-8097; 8079-8095; 9862-9811; 9870-9897; 9875-9893; 9875-9891; 9877-9893; 11699-11719; 12342-12366; 12345-12364; 12346-12364; 12347-12364; 12353-12380; 12357-12376; 12358-12376; 12358-12373; 12360-12376; 14128-14148; 16863-16883; 46091-46111; 50692-50709; 50693-50709; 50693-50708; 61325-61349; 66133-66157; 66136-66157; 66136-66155; 66136-66153; 66138-66153; 66184-66200; 67067-67083; 4171-74220; 74199-74220; 74202-74220; 74171-74219; 74199-74219; 74202-74219; 74171-74218; 74199-74218; 74202-74218; 74723-74768; 74764-74803; 74782-74802; 74782-74801; 74782-74800; 74782-74799; 74783-74802; 74783-74801; 74783-74800; 74783-74799; 74862-74893; 74900-74977; 74902-74922; 74902-74920; 75070-75119; 75164-75199; 75254-75287; 75412-75443; 75421-75439; 75422-75439; 75422-75438; 75423-75439; 75423-75438; 75493-75528; 75616-75643; 75626-75641; 75658-75699; 75676-75692; 75717-75745; 75726-75759; 75726-75745; 75727-75745; 75728-75745; 75831-75988; 75852-75969; 75969-75984; 75987-76056; 76000-76046; 76000-76032; 76000-76018; 76014-76046; 76014-76032; 76029-76046; or 76031-76046 of SEQ ID NO: 2, wherein the nucleobase sequence of the modified oligonucleotide is complementary to SEQ ID NO: 2.

In certain embodiments, the nucleobase sequence of the modified oligonucleotide comprises the sequence of SEQ ID NO: 12 or consists of the sequence of SEQ ID NO: 12. In certain embodiments, the modified oligonucleotide is 100% complementary to SEQ ID NO: 1 or 2.

In certain embodiments, the nucleobase sequence of the modified oligonucleotide comprises the sequence of any of the STAT3 antisense oligonucleotides described in WO 2012/135736, which is incorporated by reference in its entirety herein.

In certain embodiments, the modified oligonucleotide is a single-stranded modified oligonucleotide. In certain embodiments, the modified oligonucleotide comprises at least one modified internucleoside linkage. In several embodiments, each internucleoside linkage is a phosphorothioate internucleoside linkage. In certain embodiments, at least one nucleoside comprises a modified sugar, such as a bicyclic sugar including, but not limited to, a 4'-CH$_2$—O-2' bridge or a 4'-CH(CH$_3$)—O-2' bridge. In certain embodiments, the modified sugar comprises a 2'-O(CH$_2$)$_2$—OCH$_3$ group. In certain embodiments, at least one nucleoside comprises a modified nucleobase, such as a 5-methylcytosine.

In certain embodiments, the modified oligonucleotide comprises:
 a 5'-wing consisting of 1 to 5 linked nucleosides;
 a 3'-wing consisting of 1 to 5 linked nucleosides; and
 a gap between the 5'-wing and the 3'-wing consisting of 8 to 12 linked 2'-deoxynucleosides;
wherein at least one of the 5'-wing and the 3'-wing comprises at least one bicyclic nucleoside or one 2'-substituted nucleoside. In certain embodiments, the 2'-substituted nucleoside comprises a 2'-O(CH$_2$)$_2$—OCH$_3$ group or a 2'-O—CH$_3$ group. In certain embodiments, the bicyclic nucleoside comprises a 4'-CH$_2$—O-2' bridge or a 4'-CH(CH$_3$)—O-2' bridge.

In certain embodiments, pharmaceutical compositions described herein are administered in the form of a dosage unit (e.g., injection, infusion, etc.). In certain embodiments, such pharmaceutical compositions comprise an antisense oligonucleotide in an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned amounts of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the dosage unit can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the antisense oligonucleotide has the nucleobase sequence of SEQ ID NO: 12. In certain embodiments, the antisense oligonucleotide is ISIS 481464.

In certain embodiments, pharmaceutical compositions described herein comprise a dose of antisense oligonucleotide in an amount in the range of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned amounts of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the dose of antisense oligonucleotide can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

The compositions described herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents. However, such materials, when added, should not unduly interfere with the biological activities of the components of the compositions described herein. The formulations can be sterilized and, if desired, mixed with auxiliary agents, e.g., preservatives, stabilizers, wetting agents, emulsifiers, salts for influencing osmotic pressure, buffers, colorings, and/or aromatic substances and the like which do not deleteriously interact with the oligonucleotide(s) of the formulation.

Antisense oligonucleotides may be covalently linked to one or more moieties or conjugates which enhance the activity, cellular distribution or cellular uptake of the antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense oligonucleotides can also be modified to have one or more stabilizing groups that are generally attached to one or both termini of antisense compounds to enhance properties such as, for example, nuclease stability. Included in stabilizing groups are cap structures. These terminal modifications protect the antisense oligonucleotide having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Certain Treatments

In certain aspects there is provided a method of treating a subject suffering from cancer comprising administering to the subject an antisense compound complementary to human STAT3. In certain embodiments the antisense compound complementary to human STAT3 is as described herein or as disclosed in WO2012/135736.

In certain embodiments the cancer is selected from B-cell lymphoma or hepatocellularcarcinoma. In certain aspects there is provided an antisense compound complementary to human STAT3 for use in treating cancer. In certain embodiments the antisense compound complementary to human STAT3 is as described herein or as disclosed in WO2012/135736. In certain embodiments the cancer is selected from B-cell lymphoma or hepatocellularcarcinoma.

In certain aspects there is provided an antisense compound complementary to human STAT3 for use in a method of treating cancer in a subject in need thereof, wherein the method comprises administering to the subject the antisense compound in a loading phase and then a maintenance phase, wherein the loading phase involves administering a total weekly dose of the compound in the range of about 15-750 mg for the first 1-10 weeks, and the maintenance phase involves administering a total weekly dose in the range of 15-250 mg for at least 1 week after the loading phase. In certain embodiments the antisense compound complementary to human STAT3 is as described herein or as disclosed in WO2012/135736. In certain embodiments the cancer is selected from B-cell lymphoma or hepatocellularcarcinoma.

Certain aspects are directed to use of an antisense compound complementary to human STAT3 for the manufacture of a medicament for treating cancer. In certain embodiments the antisense compound complementary to human STAT3 is as described herein or as disclosed in WO2012/135736. In certain embodiments the cancer is selected from B-cell lymphoma or hepatocellularcarcinoma.

In particular embodiments of any of these aspects, the B-cell lymphoma is a non-Hodgkin's B-cell lymphoma. Examples of non-Hodgkin's B-cell lymphoma of certain aspects include, but are not limited to, diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the non-Hodgkin's B-cell lymphoma is diffuse large B cell lymphoma (DLBCL).

Certain Dosing Regimens

In certain embodiments, pharmaceutical compositions are administered according to a dosing regimen. In certain such embodiments, the dosing regimen comprises a loading phase and a maintenance phase. In certain such embodiments, the dosing regimen is effective to treat cancer and acceptably tolerable in a subject. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, the loading phase includes 1, 2, 3, 4, 5, 6, 7, 8, 9, 10, 11, 12, 13, 14, 15, 16, 17, 18, 19, or more than 20 doses.

In certain embodiments, the loading phase lasts from 1 day to 6 months. In certain embodiments a loading phase lasts 1 day, 2 days, 3, days, 4, days, 5 days, 6 days, or 7 days as measured from administration of the first dose of the loading phase to administration of the first dose of the maintenance phase. In certain embodiments a loading phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, or 26 weeks as measured from administration of the first dose of the loading phase to administration of the first dose of the maintenance phase. In certain embodiments, the loading phase lasts 1 month, 2 months, 3 months, 4 months, 5 months, or 6 months as measured from administration of the first dose of the loading phase to administration of the first dose of the maintenance phase.

In certain embodiments, the dose administered during the loading phase is lower than the dose administered during the maintenance phase. In certain embodiments, the dose administered during the loading phase is lower than the dose administered during the maintenance phase to avoid undesired side effects. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments, the dose administered during the loading phase is higher than the dose administered during the maintenance phase. In certain embodiments, the dose administered during the loading phase is higher than the dose administered during the maintenance phase to quickly achieve steady state reduction of STAT3 mRNA expression, STAT3 protein expression, and/or STAT3 activity. In certain embodiments, the dose administered during the loading phase is higher than the dose administered during the maintenance phase to avoid undesired side effects in the maintenance phase. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments where the loading phase includes more than one dose, the doses administered during the loading phase are all the same amount as one another. In certain embodiments, the doses administered during the loading phase are not all the same amount. In certain embodiments, the doses given during the loading phase increase over time. In certain embodiments, the doses given during the loading phase decrease over time.

In certain embodiments, a loading dose is administered by parenteral administration. In certain embodiments, the parenteral administration is subcutaneous administration. In certain embodiments, the parenteral administration is intravenous infusion.

In certain embodiments, the doses administered during the loading phase are about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose is 2.0 milligrams of the antisense compound per kilogram of the subject's body weight per week (2.0 mg/kg/wk). In certain embodiments, the subject's body weight is calculated as the ideal body weight using the Devine formula (Pai, M. P. and Paloucek, F. P. Ann Pharmacol. 2000. 34: 1066-1069): for men (in kg)=50+2.3 kg/inch over 5 feet; for women (in kg)=45.5+2.3 kg/inch over 5 feet.

In certain embodiments, the doses administered during the loading phase are about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned doses of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the doses can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, dose, dose frequency, and duration of the loading phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, doses, dose frequency, and duration of the loading phase may be selected to achieve a desired plasma trough concentration of a pharmaceutical composition. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, dose, dose frequency, and duration of the loading phase may be selected to achieve a desired effect within 1 to 26 weeks. In certain embodiments, the dose is the same and the dose frequency is varied to achieve the desired effect within 1 to 26 weeks. In certain embodiments, the dose increases over time and the dose frequency remains constant. In certain embodiments, one or more doses of the loading phase are greater than one or more doses of the maintenance phase. In certain embodiments, each of the loading doses is greater than each of the maintenance doses. In certain embodiments, it is desirable to achieve a desired effect as quickly as possible. In certain embodiments, a loading phase with a high dose and/or high dose frequency may be desirable.

In certain embodiments, doses, dose frequency, and duration of the loading phase may be selected to achieve an acceptable safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses increase over time. In certain embodiments, one or more doses of the loading phase are lower than one or more doses of the maintenance phase. In certain embodiments, a safety profile is not acceptable when ALT is 5-10 times the upper limit of normal. In certain embodiments, a safety profile is not acceptable when ALT is 5-10 times the upper limit of normal, and bilirubin is elevated two or more times the upper limit of normal. In certain embodiments, an acceptable safety profile comprises ALT elevations that are above three times the upper limit of normal, but do not exceed five times the upper limit of normal. In certain embodiments, an acceptable safety profile comprises ALT elevations that are above three times the upper limit of normal, but do not exceed five times the upper limit of normal, and bilirubin elevations that do not exceed two times the upper limit of normal. In certain embodiments, when administration of a pharmaceutical composition of the invention results in ALT elevations that are above three times the upper limit of normal, the dose and/or dose frequency is adjusted to mitigate the ALT elevation.

In certain embodiments, the maintenance phase includes 1, 2, 3, 4, 5, 6, 7, 8, 9, 10, 11, 12, 13, 14, 15, 16, 17, 18, 19, 20, or more than 20 doses.

In certain embodiments, the maintenance phase lasts from one day to the lifetime of the subject. In certain embodiments, the maintenance phase lasts 1 day, 2 days, 3 days, 4 days, 5 days, 6 days, or 7 days as measured from administration of the last dose of the loading phase to administration of the last dose of the maintenance phase. In certain embodiments, the maintenance phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks as measured from administration of the last dose of the loading phase to administration of the last dose of the maintenance phase. In certain embodiments, the maintenance phase lasts 1 month, 2 months, 3 months, 4 months, 5 months, 6 months, 7 months, 8 months, 9 months, 10 months, 11 months, or 12 months as measured from administration of the last dose of the loading phase to administration of the last dose of the maintenance phase. In certain embodiments, the maintenance phase lasts 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years 35 years, 36 years, 37 years, 38 years, 39 years, 40 years, 41 years, 42 years, 43 years, 44 years, 45 years, 46 years, 47 years, 48 years, 49 years, or 50 years as measured from administration of the last dose of the loading phase to administration of the last dose of the maintenance phase. In certain embodiments, the maintenance phase lasts as long as the dose continues to be needed, effective, and tolerated.

In certain embodiments where the maintenance phase includes more than one dose, the doses administered during the maintenance phase are all the same as one another. In certain embodiments, the doses administered during the maintenance phase are not all the same. In certain embodiments, the doses increase over time. In certain embodiments, the doses decrease over time.

In certain embodiments, a maintenance dose is administered by parenteral administration. In certain embodiments, the parenteral administration is subcutaneous administration. In certain embodiments, the parenteral administration is intravenous infusion.

In certain embodiments, the doses during the maintenance phase are about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose is 2.0 milligrams of the antisense compound per kilogram of the subject's body weight per week (2.0 mg/kg/wk). In certain embodiments, the subject's body weight is calculated as the ideal body weight using the Devine formula (Pai, M. P. and Paloucek, F. P. Ann Pharmacol. 2000. 34: 1066-1069): for men (in kg)=50+2.3 kg/inch over 5 feet; for women (in kg)=45.5+2.3 kg/inch over 5 feet.

In certain embodiments, the doses during the maintenance phase are about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. It will be understood that the aforementioned doses of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the doses can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann Pharmacol. 2000. 34: 1066-1069): for men (in kg)=50+2.3 kg/inch over 5 feet; for women (in kg)=45.5+2.3 kg/inch over 5 feet.

In certain embodiments, doses, dose frequency, and duration of the maintenance phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent described herein at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time.

In certain embodiments, doses, dose frequency, and duration of the maintenance phase may be selected to achieve a desired plasma trough concentration of a pharmaceutical composition. In certain embodiments, the pharmaceutical composition is an antisense oligonucleotide. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, doses, dose frequency, and duration of the maintenance phase may be selected to achieve a desired safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses, dose frequency, and duration of the maintenance phase may be adjusted from time to time to achieve a desired effect. In certain embodiments, subjects are monitored for effects (therapeutic and/or toxic effects) and doses, dose frequency, and/or duration of the maintenance phase may be adjusted based on the results of such monitoring.

In certain embodiments, pharmaceutical compositions are administered according to a dosing regimen comprising a first phase and a second phase. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, the first phase includes 1, 2, 3, 4, 5, 6, 7, 8, 9, 10, 11, 12, 13, 14, 15, 16, 17, 18, 19, or more than 20 doses.

In certain embodiments, the first phase lasts from 1 day to 6 months. In certain embodiments a first phase lasts 1 day, 2 days, 3, days, 4, days, 5 days, 6 days, or 7 days as measured from administration of the first dose of the first phase to administration of the first dose of the second phase. In certain embodiments a first phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, or 26 weeks as measured from administration of the first dose of the first phase to administration of the first dose of the second phase. In certain embodiments, the first phase lasts 1 month, 2 months, 3 months, 4 months, 5 months, or 6 months as measured from administration of the first dose of the first phase to administration of the first dose of the second phase.

In certain embodiments, the dose administered during the first phase is lower than the dose administered during the second phase. In certain embodiments, the dose administered during the first phase is lower than the dose administered during the second phase to avoid undesired side effects. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments, the dose administered during the first phase is higher than the dose administered during the second phase. In certain embodiments, the dose administered during the first phase is higher than the dose administered during the second phase to quickly achieve steady state reduction of STAT3 mRNA expression, STAT3 protein expression, and/or STAT3 activity. In certain embodiments, the dose administered during the first phase is higher than the dose administered during the second phase to avoid undesired side effects in the second phase. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments where the first phase includes more than one dose, the doses administered during the first phase are all the same amount as one another. In certain embodiments, the doses administered during the first phase are not all the same amount. In certain embodiments, the doses given during the first phase increase over time. In certain embodiments, the doses given during the first phase decrease over time.

In certain embodiments, a first dose is administered by parenteral administration. In certain embodiments, the parenteral administration is subcutaneous administration. In certain embodiments, the parenteral administration is intravenous infusion.

The range of dosages capable of being administered during the "first phase" and/or "second phase" are the same as can be used for the "loading phase" and "maintenance phase" referred to above. In certain embodiments, dose, dose frequency, and duration of the first phase and/or second phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, doses, dose frequency, and duration of the first phase and/or second phase may be selected to achieve a desired plasma trough concentration of a pharmaceutical composition. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, dose, dose frequency, and duration of the first phase and/or second phase may be selected to achieve a desired effect within 1 to 26 weeks. In certain embodiments, the dose is the same and the dose frequency is varied to achieve the desired effect within 1 to 26 weeks. In certain embodiments, the dose increases over time and the dose frequency remains constant. In certain embodiments, one or more doses of the first phase are greater than one or more doses of the second phase. In certain embodiments, each of the first doses is greater than each of the second doses. In certain embodiments, it is desirable to achieve a desired effect as quickly as possible. In certain embodiments, a first phase with a high dose and/or high dose frequency may be desirable. In certain embodiments, doses, dose frequency, and duration of the first phase and/or second phase may be selected to achieve an acceptable safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses increase over time. In certain embodiments, one or more doses of the first phase are lower than one or more doses of the second phase. In certain embodiments, a safety profile is not acceptable when ALT is 5-10 times the upper limit of normal. In certain embodiments, a safety profile is not acceptable when ALT is 5-10 times the upper limit of normal, and bilirubin is elevated two or more times the upper limit of normal. In certain embodiments, an acceptable safety profile comprises ALT elevations that are above three times the upper limit of normal, but do not exceed five times the upper limit of normal. In certain embodiments, an acceptable safety profile comprises ALT elevations that are above three times the upper limit of normal, but do not exceed five times the upper limit of normal, and bilirubin elevations that do not exceed two times the upper limit of normal. In certain embodiments, when administration of a pharmaceutical composition of the invention results in ALT elevations that are above three times the upper limit of normal, the dose and/or dose frequency is adjusted to mitigate the ALT elevation. In certain embodiments, the second phase includes 1, 2, 3, 4, 5, 6, 7, 8, 9, 10, 11, 12, 13, 14, 15, 16, 17, 18, 19, 20, or more than 20 doses. In certain embodiments, the second phase lasts from one day to the lifetime of the subject. In certain embodiments, the second phase lasts 1 day, 2 days, 3 days, 4 days, 5 days, 6 days, or 7 days as measured from administration of the last dose of the first phase to administration of the last dose of the second phase. In certain embodiments, the second phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks as measured from administration of the last dose of the first phase to administration of the last dose of the second phase. In certain embodiments, the second phase lasts 1 month, 2 months, 3 months, 4 months, 5 months, 6 months, 7 months, 8 months, 9 months, 10 months, 11 months, or 12 months as measured from administration of the last dose of the first phase to administration of the last dose of the second phase. In certain embodiments, the second phase lasts 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years 35 years, 36 years, 37 years, 38 years, 39 years, 40 years, 41 years, 42 years, 43 years, 44 years, 45 years, 46 years, 47 years, 48 years, 49 years, or 50 years as measured from administration of the last dose of the first phase to administration of the last dose of the second phase.

In certain embodiments, the second phase lasts as long as the dose continues to be needed, effective, and tolerated.

In certain embodiments where the second phase includes more than one dose, the doses administered during the second phase are all the same as one another. In certain embodiments, the doses administered during the second phase are not all the same. In certain embodiments, the doses increase over time. In certain embodiments, the doses decrease over time.

In certain embodiments, a second dose is administered by parenteral administration. In certain embodiments, the parenteral administration is subcutaneous administration. In certain embodiments, the parenteral administration is intravenous infusion.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a STAT3 nucleic acid is 12 to 30 subunits in length. In certain embodiments, an antisense compound targeted to a STAT3 nucleic acid is 14 to 30 subunits in length. In certain embodiments, an antisense compound targeted to a STAT3 nucleic acid is 12 to 22 subunits in length. In other words, such antisense compounds are from 12 to 30 linked subunits, 14 to 30 linked subunits, or 12 to 22 linked subunits, respectively. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compound is an antisense oligonucleotide, and the linked subunits are nucleotides.

In certain embodiments, antisense oligonucleotides targeted to a STAT3 nucleic acid may be shortened or truncated. For example, a single subunit may be deleted from the 5' end (5' truncation), or alternatively from the 3' end (3' truncation). A shortened or truncated antisense compound targeted to a STAT3 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a STAT3 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variants, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, gapmers provided herein include, for example, 11-mers having a motif of 1-9-1.

In certain embodiments, gapmers provided herein include, for example, 12-mers having a motif of 1-9-2, 2-9-1, or 1-10-1.

In certain embodiments, gapmers provided herein include, for example, 13-mers having a motif of 1-9-3, 2-9-2, 3-9-1, 1-10-2, or 2-10-1.

In certain embodiments, gapmers provided herein include, for example, 14-mers having a motif of 1-9-4, 2-9-3, 3-9-2, 4-9-1, 1-10-3, 2-10-2, or 3-10-1.

In certain embodiments, gapmers provided herein include, for example, 15-mers having a motif of 1-9-5, 2-9-4, 3-9-3, 4-9-2, 5-9-1, 1-10-4, 2-10-3, 3-10-2, or 4-10-1.

In certain embodiments, gapmers provided herein include, for example, 16-mers having a motif of 2-9-5, 3-9-4, 4-9-3, 5-9-2, 1-10-5, 2-10-4, 3-10-3, 4-10-2, or 5-10-1.

In certain embodiments, gapmers provided herein include, for example, 17-mers having a motif of 3-9-5, 4-9-4, 5-9-3, 2-10-5, 3-10-4, 4-10-3, or 5-10-2.

In certain embodiments, gapmers provided herein include, for example, 18-mers having a motif of 4-9-5, 5-9-4, 3-10-5, 4-10-4, or 5-10-3.

In certain embodiments, gapmers provided herein include, for example, 19-mers having a motif of 5-9-5, 4-10-5, or 5-10-4.

In certain embodiments, gapmers provided herein include, for example, 20-mers having a motif of 5-10-5.

In certain embodiments, the antisense compound has a "wingmer" motif, having a wing-gap or gap-wing configuration, i.e. an X—Y or Y—Z configuration as described above for the gapmer configuration. Thus, wingmer configurations provided herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compound targeted to a STAT3 nucleic acid has a 2-10-2 gapmer motif.

In certain embodiments, the antisense compound targeted to a STAT3 nucleic acid has a 3-10-3 gapmer motif.

In certain embodiments, the antisense compound targeted to a STAT3 nucleic acid has a 5-10-5 gapmer motif.

In certain embodiments, the antisense compound targeted to a STAT3 nucleic acid has a 1-10-5 gapmer motif.

In certain embodiments, the antisense compound targeted to a STAT3 nucleic acid has a 3-10-4 gapmer motif.

In certain embodiments, the antisense compound targeted to a STAT3 nucleic acid has a 2-10-4 gapmer motif.

In certain embodiments, the antisense compound targeted to a STAT3 nucleic acid has a 4-9-3 gapmer motif.

In certain embodiments, the antisense compound targeted to a STAT3 nucleic acid has a gap-widened motif.

In certain embodiments, the antisense compounds targeted to a STAT3 nucleic acid has any of the following sugar motifs:

k-d(10)-k
e-d(10)-k
k-d(10)-e
k-k-d(10)-k-k
k-k-d(10)-e-e
e-e-d(10)-k-k
k-k-k-d(10)-k-k-k
e-e-e-d(10)-k-k-k
k-k-k-d(10)-e-e-e
k-k-k-d(10)-k-k-k
e-k-k-d(10)-k-k-e
e-e-k-d(10)-k-k-e
e-d-k-d(10)-k-k-e
e-k-d(10)-k-e-k-e
k-d(10)-k-e-k-e
e-e-k-d(10)-k-e-k-e
e-d-d-k-d(9)-k-k-e
e-e-e-e-d(9)-k-k-e wherein, k is a constrained ethyl nucleoside, e is a 2'-MOE substituted nucleoside, and d is a 2'-deoxynucleoside.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

Target Nucleic Acids, Target Regions and Nucleotide Sequences

Nucleotide sequences that encode STAT3 include, without limitation, the following: GENBANK Accession No. NM_139276.2 (incorporated herein as SEQ ID NO: 1) and the complement of GENBANK Accession No. NT_010755.14 truncated from nucleotides 4185000 to U.S. Pat. No. 4,264,000 (incorporated herein as SEQ ID NO: 2).

It is understood that the sequence set forth in each SEQ ID NO contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for STAT3 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in STAT3 mRNA levels are indicative of inhibition of STAT3 expression. Reductions in levels of a STAT3 protein are also indicative of inhibition of target mRNA expression. Further, phenotypic changes are indicative of inhibition of STAT3 expression. In certain embodiments, reduced cellular growth, reduced tumor growth, and reduced tumor volume can be indicative of inhibition of STAT3 expression. In certain embodiments, amelioration of symptoms associated with cancer can be indicative of inhibition of STAT3 expression. In certain embodiments, reduction of cachexia is indicative of inhibition of STAT3 expression. In certain embodiments, reduction of cancer markers can be indicative of inhibition of STAT3 expression.

Hybridization

In some embodiments, hybridization occurs between an antisense compound disclosed herein and a STAT3 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a STAT3 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a STAT3 nucleic acid).

Non-complementary nucleobases between an antisense compound and a STAT3 nucleic acid may be tolerated provided that the antisense compound remains able to specifically hybridize to a target nucleic acid. Moreover, an antisense compound may hybridize over one or more segments of a STAT3 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a STAT3 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410;

Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a STAT3 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a STAT3 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a STAT3 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a STAT3 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)2OCH$_3$ substituent groups. The substituent at the 2' position can also be selected from allyl, amino, azido, thio, O-allyl, O—$C_1$-$C_{10}$ alkyl, OCF$_3$, O(CH$_2$)2SCH$_3$, O(CH$_2$)2-O—N(Rm)(Rn), and O—CH$_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H(CH$_2$OCH$_3$)—O-2', and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, $C_1$-$C_{12}$ alkyl, or a protecting group (see, U.S. Pat. No. 7,427,672, issued on Sep. 23, 2008); 4'-CH$_2$—C(H)(CH$_3$)-2' (see, Chattopadhyaya, et al., *J. Org. Chem.*, 2009, 74, 118-134); and 4'-CH$_2$—C(=CH$_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. No. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or, —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2', and 4'-CH$_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

(A)
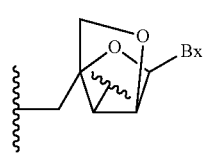

(B)
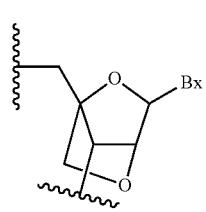

(C)
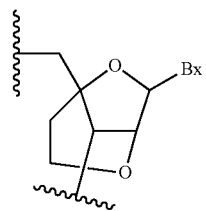

(D)
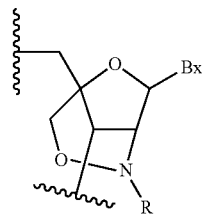

(E)
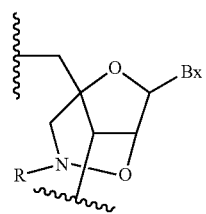

(F)
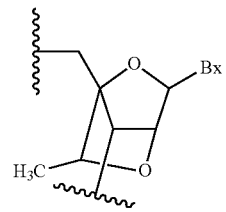

(G)
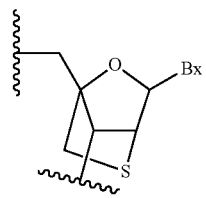

(H)
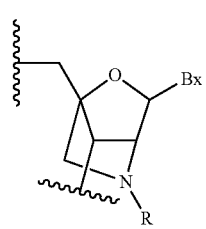

(I)
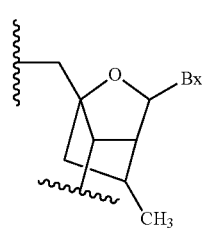

-continued

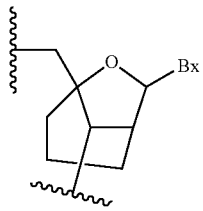
(J)

wherein Bx is the base moiety and R is, independently, H, a protecting group or $C_1$-$C_{12}$ alkyl.

In certain embodiments, bicyclic nucleoside having Formula I:

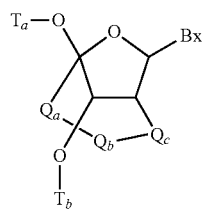
I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

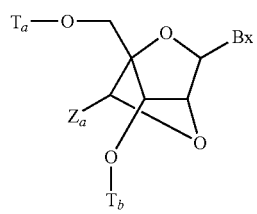
II wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_cC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

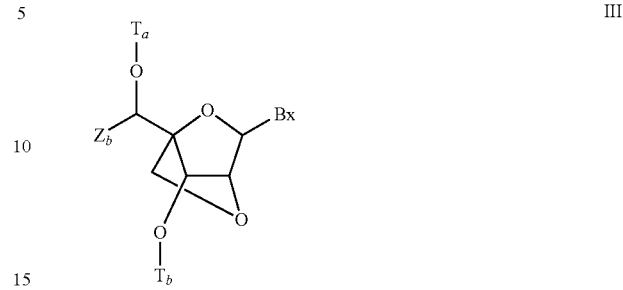
III wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

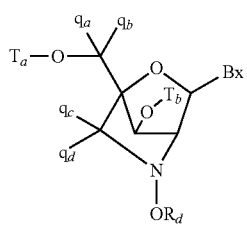
IV wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

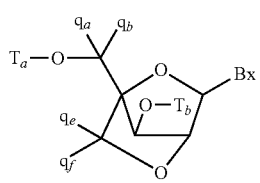
V wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_1$-$C_{12}$ alkenyl, $C_1$-$C_{12}$ alkynyl, substituted $C_2$-$C_{12}$ alkynyl, $C_1$-$C_{12}$ alkoxy, substituted $C_1$-$C_{12}$ alkoxy, $OJ_h$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel conformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

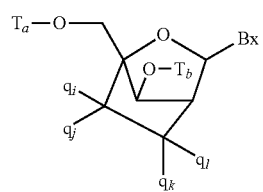

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$—$NH_2$, O($CH_2$)$_n$—$CH_3$, O($CH_2$)$_n$—$ONH_2$, $OCH_2$C(=O)N(H)$CH_3$, and O($CH_2$)$_n$—ON[($CH_2$)$_n$—$CH_3$]$_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X

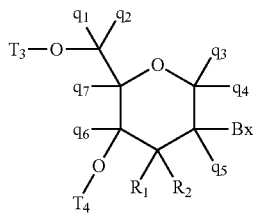

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a STAT3 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a STAT3 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Certain Antisense Compounds

In certain embodiments, antisense compounds useful for treating B-cell lymphoma at the doses and dosing regimens described above include any of the antisense oligonucleotides described in WO 2012/135736, which is incorporated by reference in its entirety herein. Examples of antisense compounds described in WO 2012/135736 suitable for treating B-cell lymphoma include, but are not limited to, those described in Tables 1 & 2 below:

TABLE 1 cEt and MOE chimeric antisense oligonucleotides targeted to STAT3 (SEQ ID NO: 1)

| ISIS NO | Human Start Site | Human Stop Site | Sequence | Motif | Wing Chem | SEQ ID NO |
|---|---|---|---|---|---|---|
| 481355 | 322 | 337 | ACTGCCGCAGCTCCAT | 3-10-3 | cEt | 3 |
| 481597 | 731 | 744 | GAGATTCTCTACCA | 2-10-2 | cEt | 4 |
| 481374 | 788 | 803 | AGATCTTGCATGTCTC | 3-10-3 | cEt | 5 |
| 481390 | 1305 | 1320 | ATAATTCAACTCAGGG | 3-10-3 | cEt | 6 |
| 481420 | 1948 | 1963 | ACTTTTTCACAAGGTC | 3-10-3 | cEt | 7 |
| 481431 | 2206 | 2221 | CCATGATCTTATAGCC | 3-10-3 | cEt | 8 |
| 481453 | 2681 | 2696 | GATAGCAGAAGTAGGA | 3-10-3 | cEt | 9 |
| 481463 | 3001 | 3016 | CAAGGTTAAAAAGTGC | 3-10-3 | cEt | 10 |
| 481688 | 3002 | 3015 | AAGGTTAAAAAGTG | 2-10-2 | cEt | 11 |
| 481464 | 3016 | 3031 | CTATTTGGATGTCAGC | 3-10-3 | cEt | 12 |
| 481689 | 3017 | 3030 | TATTTGGATGTCAG | 2-10-2 | cEt | 13 |
| 481465 | 3032 | 3047 | TAGATAGTCCTATCTT | 3-10-3 | cEt | 14 |
| 481690 | 3033 | 3046 | AGATAGTCCTATCT | 2-10-2 | cEt | 15 |
| 481466 | 3047 | 3062 | AAGAAACCTAGGGCTT | 3-10-3 | cEt | 16 |
| 481691 | 3048 | 3061 | AGAAACCTAGGGCT | 2-10-2 | cEt | 17 |
| 481467 | 3097 | 3112 | GCTGATACAGTGTTTT | 3-10-3 | cEt | 18 |
| 481692 | 3098 | 3111 | CTGATACAGTGTTT | 2-10-2 | cEt | 19 |
| 481468 | 3112 | 3127 | ATACAGAAAGGCTATG | 3-10-3 | cEt | 20 |
| 481693 | 3113 | 3126 | TACAGAAAGGCTAT | 2-10-2 | cEt | 21 |
| 481469 | 3127 | 3142 | GCTTAAGTTTCTTAAA | 3-10-3 | cEt | 22 |
| 481694 | 3128 | 3141 | CTTAAGTTTCTTAA | 2-10-2 | cEt | 23 |

TABLE 1-continued cEt and MOE chimeric antisense oligonucleotides targeted to STAT3 (SEQ ID NO: 1)

| ISIS NO | Human Start Site | Human Stop Site | Sequence | Motif | Wing Chem | SEQ ID NO |
|---|---|---|---|---|---|---|
| 481470 | 3461 | 3476 | AGCACCAAGGAGGCTG | 3-10-3 | cEt | 24 |
| 481695 | 3462 | 3475 | GCACCAAGGAGGCT | 2-10-2 | cEt | 25 |
| 481471 | 3476 | 3491 | AAGCTGAATGCTTAAA | 3-10-3 | cEt | 26 |
| 481696 | 3477 | 3490 | AGCTGAATGCTTAA | 2-10-2 | cEt | 27 |
| 481472 | 3491 | 3506 | TTACCAGCCTGAAGGA | 3-10-3 | cEt | 28 |
| 481697 | 3492 | 3505 | TACCAGCCTGAAGG | 2-10-2 | cEt | 29 |
| 481473 | 3506 | 3521 | CAGGGATTATATAAAT | 3-10-3 | cEt | 30 |
| 481698 | 3507 | 3520 | AGGGATTATATAAA | 2-10-2 | cEt | 31 |
| 481474 | 3521 | 3536 | ACCTGAAGCCCGTTTC | 3-10-3 | cEt | 32 |
| 481699 | 3522 | 3535 | CCTGAAGCCCGTTT | 2-10-2 | cEt | 33 |
| 481475 | 3536 | 3551 | TGTCTTAAGGGTTTGA | 3-10-3 | cEt | 34 |
| 481700 | 3537 | 3550 | GTCTTAAGGGTTTG | 2-10-2 | cEt | 35 |
| 481476 | 3551 | 3566 | GGTTGCAGCTTCAGAT | 3-10-3 | cEt | 36 |
| 481701 | 3552 | 3565 | GTTGCAGCTTCAGA | 2-10-2 | cEt | 37 |
| 481477 | 3567 | 3582 | TCAACACCAAAGGCCA | 3-10-3 | cEt | 38 |
| 481702 | 3568 | 3581 | CAACACCAAAGGCC | 2-10-2 | cEt | 39 |
| 481478 | 3585 | 3600 | TCCTTAAACCTTCCTA | 3-10-3 | cEt | 40 |
| 481703 | 3586 | 3599 | CCTTAAACCTTCCT | 2-10-2 | cEt | 41 |
| 481479 | 3600 | 3615 | AAAATGCTTAGATTCT | 3-10-3 | cEt | 42 |
| 481704 | 3601 | 3614 | AAATGCTTAGATTC | 2-10-2 | cEt | 43 |
| 481480 | 3628 | 3643 | AAATAAGTCTATTTAT | 3-10-3 | cEt | 44 |
| 481705 | 3629 | 3642 | AATAAGTCTATTTA | 2-10-2 | cEt | 45 |
| 481481 | 3648 | 3663 | GGCCAATACATTACAA | 3-10-3 | cEt | 46 |
| 481706 | 3649 | 3662 | GCCAATACATTACA | 2-10-2 | cEt | 47 |
| 481482 | 3670 | 3685 | TGCCCAGCCTTACTCA | 3-10-3 | cEt | 48 |
| 481707 | 3671 | 3684 | GCCCAGCCTTACTC | 2-10-2 | cEt | 49 |
| 481483 | 3685 | 3700 | GTTGTAAGCACCCTCT | 3-10-3 | cEt | 50 |
| 481708 | 3686 | 3699 | TTGTAAGCACCCTC | 2-10-2 | cEt | 51 |
| 481484 | 3700 | 3715 | AGAAAGGGAGTCAAGG | 3-10-3 | cEt | 52 |
| 481709 | 3701 | 3714 | GAAAGGGAGTCAAG | 2-10-2 | cEt | 53 |
| 481485 | 3717 | 3732 | GCAGATCAAGTCCAGG | 3-10-3 | cEt | 54 |
| 481710 | 3718 | 3731 | CAGATCAAGTCCAG | 2-10-2 | cEt | 55 |
| 481486 | 3730 | 3745 | AGCCTCTGAAACAGCA | 3-10-3 | cEt | 56 |
| 481711 | 3731 | 3744 | GCCTCTGAAACAGC | 2-10-2 | cEt | 57 |
| 481487 | 3746 | 3761 | CCCACAGAAACAACCT | 3-10-3 | cEt | 58 |
| 481712 | 3747 | 3760 | CCACAGAAACAACC | 2-10-2 | cEt | 59 |
| 481488 | 3761 | 3776 | AGCCCTGATAAGGCAC | 3-10-3 | cEt | 60 |

TABLE 1-continued cEt and MOE chimeric antisense oligonucleotides targeted to STAT3 (SEQ ID NO: 1)

| ISIS NO | Human Start Site | Human Stop Site | Sequence | Motif | Wing Chem | SEQ ID NO |
|---|---|---|---|---|---|---|
| 481713 | 3762 | 3775 | GCCCTGATAAGGCA | 2-10-2 | cEt | 61 |
| 481489 | 3776 | 3791 | AATCAGAAGTATCCCA | 3-10-3 | cEt | 62 |
| 481714 | 3777 | 3790 | ATCAGAAGTATCCC | 2-10-2 | cEt | 63 |
| 481490 | 3833 | 3848 | GCCTCTAGCAGGATCA | 3-10-3 | cEt | 64 |
| 481715 | 3834 | 3847 | CCTCTAGCAGGATC | 2-10-2 | cEt | 65 |
| 481491 | 3848 | 3863 | CACGCAAGGAGACATG | 3-10-3 | cEt | 66 |
| 481716 | 3849 | 3862 | ACGCAAGGAGACAT | 2-10-2 | cEt | 67 |
| 481492 | 3863 | 3878 | TGAGGGACCTTTAGAC | 3-10-3 | cEt | 68 |
| 481717 | 3864 | 3877 | GAGGGACCTTTAGA | 2-10-2 | cEt | 69 |
| 481493 | 3886 | 3901 | CAGGATTCCTAAAACA | 3-10-3 | cEt | 70 |
| 481718 | 3887 | 3900 | AGGATTCCTAAAAC | 2-10-2 | cEt | 71 |
| 481494 | 3901 | 3916 | ATGAGGTCCTGAGACC | 3-10-3 | cEt | 72 |
| 481719 | 3902 | 3915 | TGAGGTCCTGAGAC | 2-10-2 | cEt | 73 |
| 481495 | 3940 | 3955 | CATCATGTCCAACCTG | 3-10-3 | cEt | 74 |
| 481720 | 3941 | 3954 | ATCATGTCCAACCT | 2-10-2 | cEt | 75 |
| 481496 | 3955 | 3970 | GGGCCCCATAGTGTGC | 3-10-3 | cEt | 76 |
| 481721 | 3956 | 3969 | GGCCCCATAGTGTG | 2-10-2 | cEt | 77 |
| 481497 | 3977 | 3992 | AGCTCAACCAGACACG | 3-10-3 | cEt | 78 |
| 481722 | 3978 | 3991 | GCTCAACCAGACAC | 2-10-2 | cEt | 79 |
| 481498 | 3992 | 4007 | GAACCATATTCCCTGA | 3-10-3 | cEt | 80 |
| 481723 | 3993 | 4006 | AACCATATTCCCTG | 2-10-2 | cEt | 81 |
| 481499 | 4007 | 4022 | CAAGAAACTGGCTAAG | 3-10-3 | cEt | 82 |
| 481724 | 4008 | 4021 | AAGAAACTGGCTAA | 2-10-2 | cEt | 83 |
| 481500 | 4022 | 4037 | GCCACTGGATATCACC | 3-10-3 | cEt | 84 |
| 481501 | 4048 | 4063 | AACTGAATGAAGACGC | 3-10-3 | cEt | 85 |
| 481523 | 4489 | 4504 | GCTTATTATGTACTGA | 3-10-3 | cEt | 86 |
| 481748 | 4490 | 4503 | CTTATTATGTACTG | 2-10-2 | cEt | 87 |
| 481524 | 4530 | 4545 | GCCCAAGTCTCACCTT | 3-10-3 | cEt | 88 |
| 481749 | 4531 | 4544 | CCCAAGTCTCACCT | 2-10-2 | cEt | 89 |
| 481525 | 4541 | 4556 | CCCAATGGTAAGCCCA | 3-10-3 | cEt | 90 |
| 481750 | 4542 | 4555 | CCAATGGTAAGCCC | 2-10-2 | cEt | 91 |
| 481526 | 4543 | 4558 | AACCCAATGGTAAGCC | 3-10-3 | cEt | 92 |
| 481751 | 4544 | 4557 | ACCCAATGGTAAGC | 2-10-2 | cEt | 93 |
| 481527 | 4560 | 4575 | TAGGTCCCTATGATTT | 3-10-3 | cEt | 94 |
| 481752 | 4561 | 4574 | AGGTCCCTATGATT | 2-10-2 | cEt | 95 |
| 481528 | 4579 | 4594 | AAGCCCTGAACCCTCG | 3-10-3 | cEt | 96 |
| 481753 | 4580 | 4593 | AGCCCTGAACCCTC | 2-10-2 | cEt | 97 |
| 481529 | 4615 | 4630 | CCTAAGGCCATGAACT | 3-10-3 | cEt | 98 |
| 481754 | 4616 | 4629 | CTAAGGCCATGAAC | 2-10-2 | cEt | 99 |
| 481530 | 4630 | 4645 | ACCAGATACATGCTAC | 3-10-3 | cEt | 100 |
| 481755 | 4631 | 4644 | CCAGATACATGCTA | 2-10-2 | cEt | 101 |
| 481531 | 4646 | 4661 | TACAATCAGAGTTAAG | 3-10-3 | cEt | 102 |
| 481756 | 4647 | 4660 | ACAATCAGAGTTAA | 2-10-2 | cEt | 103 |
| 481532 | 4664 | 4679 | TCCTCTCAGAACTTTT | 3-10-3 | cEt | 104 |
| 481757 | 4665 | 4678 | CCTCTCAGAACTTT | 2-10-2 | cEt | 105 |
| 481533 | 4666 | 4681 | GCTCCTCTCAGAACTT | 3-10-3 | cEt | 106 |
| 481758 | 4667 | 4680 | CTCCTCTCAGAACT | 2-10-2 | cEt | 107 |
| 481534 | 4693 | 4708 | TTCTTTAATGGGCCAC | 3-10-3 | cEt | 108 |
| 481759 | 4694 | 4707 | TCTTTAATGGGCCA | 2-10-2 | cEt | 109 |
| 481535 | 4767 | 4782 | ACGGGATTCCCTCGGC | 3-10-3 | cEt | 110 |
| 481760 | 4768 | 4781 | CGGGATTCCCTCGG | 2-10-2 | cEt | 111 |
| 481536 | 4782 | 4797 | GTAGGTAAGCAACCCA | 3-10-3 | cEt | 112 |
| 481761 | 4783 | 4796 | TAGGTAAGCAACCC | 2-10-2 | cEt | 113 |
| 481537 | 4830 | 4845 | GAATTTGAATGCAGTG | 3-10-3 | cEt | 114 |
| 481762 | 4831 | 4844 | AATTTGAATGCAGT | 2-10-2 | cEt | 115 |
| 481538 | 4844 | 4859 | TGAAGTACACATTGGA | 3-10-3 | cEt | 116 |
| 481763 | 4845 | 4858 | GAAGTACACATTGG | 2-10-2 | cEt | 117 |
| 481539 | 4860 | 4875 | ATAAATTTTTACACTA | 3-10-3 | cEt | 118 |
| 481764 | 4861 | 4874 | TAAATTTTTACACT | 2-10-2 | cEt | 119 |
| 481765 | 4869 | 4882 | CAATAATATAAATT | 2-10-2 | cEt | 120 |
| 481541 | 4934 | 4949 | CTGGAAGTTAAAGTAG | 3-10-3 | cEt | 121 |
| 481766 | 4935 | 4948 | TGGAAGTTAAAGTA | 2-10-2 | cEt | 122 |

TABLE 2

Chimeric antisense oligonucleotides targeted to STAT3
(SEQ ID NO: 2)

| Human Start Site | Human Stop Site | ISIS No | Sequence | Chemistry | SEQ ID NO |
|---|---|---|---|---|---|
| 5701 | 5716 | GTACTCTTTCAGTGGT | 529962 | e-e-e-d(10)-k-k-k | 123 |
| 74784 | 74799 | ATGCTTAGATTCTCCT | 529979 | k-k-k-d(10)-e-e-e | 124 |
| 74905 | 74920 | AGCAGATCAAGTCCAG | 529982 | k-k-k-d(10)-e-e-e | 125 |
| 75423 | 75438 | AGGTGTTCCCATACGC | 529983 | k-k-k-d(10)-e-e-e | 126 |
| 75424 | 75439 | TAGGTGTTCCCATACG | 529984 | k-k-k-d(10)-e-e-e | 127 |
| 5701 | 5716 | GTACTCTTTCAGTGGT | 529999 | k-k-k-d(10)-e-e-e | 123 |
| 9878 | 9893 | GGTTCCTCCTGTTGGC | 530006 | k-k-k-d(10)-e-e-e | 128 |
| 12361 | 12376 | GGTTCCTCCTGTTGGC | 530006 | k-k-k-d(10)-e-e-e | 128 |
| 74783 | 74799 | ATGCTTAGATTCTCCTT | 530020 | e-e-k-d(10)-k-e-k-e | 129 |

Certain Combination Therapies

In certain embodiments, one or more pharmaceutical compositions provided herein are co-administered with one or more other pharmaceutical agents. In certain embodiments, such one or more other pharmaceutical agents are designed to treat the same disease, disorder, or condition as the one or more pharmaceutical compositions provided herein. In certain embodiments, such one or more other pharmaceutical agents are designed to treat a different disease, disorder, or condition as the one or more pharmaceutical compositions provided herein. In certain embodiments, such one or more other pharmaceutical agents are designed to treat an undesired side effect of one or more pharmaceutical compositions provided herein. In certain embodiments, one or more pharmaceutical compositions provided herein are co-administered with another pharmaceutical agent to treat an undesired effect of that other pharmaceutical agent. In certain embodiments, one or more pharmaceutical compositions provided herein are co-administered with another pharmaceutical agent to produce a combinational effect. In certain embodiments, one or more pharmaceutical compositions provided herein are co-administered with another pharmaceutical agent to produce a synergistic effect.

In certain embodiments, one or more pharmaceutical compositions provided herein and one or more other pharmaceutical agents are administered at the same time. In certain embodiments, one or more pharmaceutical compositions provided herein and one or more other pharmaceutical agents are administered at different times. In certain embodiments, one or more pharmaceutical compositions provided herein and one or more other pharmaceutical agents are prepared together in a single formulation. In certain embodiments, one or more pharmaceutical compositions provided herein and one or more other pharmaceutical agents are prepared separately. In certain embodiments, one or more other pharmaceutical agents include all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, valrubicin, vinblastine, vincristine, vindesine, or vinorelbine. In certain embodiments, one or more other pharmaceutical agents include a combination of cyclophosphamide, hydroxydanuorubicin, oncovin (vincristine), prednisone or prednisolone (CHOP). In certain embodiments, one or more other pharmaceutical agents include a combination of rituximab and CHOP (R-CHOP). In certain embodiments, one or more other pharmaceutical agents include another antisense oligonucleotide. In certain embodiments, another antisense oligonucleotide is a second STAT3 antisense oligonucleotide.

In certain embodiments, one or more other pharmaceutical agents include molecular targeted therapies. In certain embodiments, the molecular targeted therapy is an EGFR inhibitor, a mTOR inhibitor, a HER2 inhibitor, or a VEGF/VEGFR inhibitor. In certain embodiments, EGFR inhibitors include gefitinib, erlotinib, lapatinib, cetuximab, panitumumbo. In certain embodiments, mTOR inhibitors include everolimus and temsirolimus. In certain embodiments, HER2 inhibitors include trastuzumab and lapatinib. In certain embodiments, VEGF/VEGFR inhibitors include pazopanib, bevacizumab, sunitinib, and sorafenib.

In certain embodiments, one more pharmaceutical compositions provided herein are administered with radiation therapy. In certain embodiments, one or more pharmaceutical compositions are administered at the same time as radiation therapy. In certain embodiments, one or more pharmaceutical compositions are administered before radiation therapy. In certain embodiments, one or more pharmaceutical compositions are administered after radiation therapy. In certain embodiments, one or more pharmaceutical compositions are administered at various time points throughout a radiation therapy regimen.

In certain embodiments, radiation therapy is useful for inhibiting tumor growth. In certain embodiments, radiation therapy is useful for increasing overall survival. In certain embodiments, radiation therapy used in conjunction with administration of one or more pharmaceuticals provided herein is advantageous over using either therapy alone because both radiation therapy and administration with one or more pharmaceuticals can be limited to achieve effective antiproliferative response with limited toxicity.

In certain embodiments, a physician designs a therapy regimen including both radiation therapy and administration of one more pharmaceutical compositions provided herein. In certain embodiments, a physician designs a therapy regimen including radiation therapy, administration of one or more pharmaceutical compositions provided herein, and administration of one or more other chemotherapeutic agents.

EXAMPLES

Non-Limiting Disclosure and Incorporation by Reference

While certain compounds, compositions and methods described herein have been described with specificity in accordance with certain embodiments, the following examples serve only to illustrate certain embodiments described herein and are not intended to limit the same. Each of the references recited in the present application is incorporated herein by reference in its entirety.

Example 1

Phase 1, Open-Label, Study for Treating a Patient Having Advanced B Cell Lymphoma with a STAT3 Antisense Oligonucleotide The effect of intravenous infusion of the STAT3 antisense oligonucleotide, ISIS 481464, in patients with advanced B cell lymphomas was studied. Patients with diffuse large B-cell lymphomas (DLBCL) were recruited for this study.

The criteria for patient inclusion with respect to their tumor status was that the tumors should be relapsed or refractory to at least one prior anti-cancer systemic therapy, and/or for which no standard therapy exists; that their disease should be measurable or evaluable, according to RECIST version 1.1 for solid tumors, or according to the International Workshop Response Criteria for Non-Hodgkin's Lymphoma for NHL tumors (Cheson, B. D. et al., J. Clin. Oncol. 1999, 17: 1244; Cheson, B. D. et al., J. Clin. Oncol. 2007, 25(5):579-86), or according to appropriate criteria for other advanced cancers. RECIST (Response Evaluation Criteria in Solid Tumors) is an internationally accepted set of guidelines used in clinical trials for solid tumor disease.

One patient fitting the criteria above is a 63 year old female with DLBCL designated herein as Patient #1001. Prior to commencing therapy, Patient #1001 showed multiple areas of hypermetabolic adenopathy, both above and below the diaphragm, including the supraclavicular, left paratracheal, right internal mammary, pericardial, left intramammary, pre-hepatic, retroperitoneal, and mesenteric regions. In addition, the patient suffered from fatigue, nausea, night sweats, shortness of breath on exertion, and peripheral neuropathy. The patient also noted 5-6 days of right-sided abdominal fullness and associated pain. Patient therapy was commenced with a treatment period comprising administration during a first phase of 3 loading doses of ISIS 481464: a 3-hr intravenous infusion of 2 mg/kg ideal body weight of ISIS 481464 administered on days 1, 3, and 5 of cycle 0. The ideal body weight was determined using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet. Treatment was then continued in a second phase by once-weekly administrations (Cycle 1 and beyond) of 2 mg/kg ideal body weight of ISIS 481464 until disease progression, unacceptable toxicity, or patient discontinuation for any other reason occurred. Disease assessments were performed at the end of even cycles.

Tumor lesions were evaluated on each even-numbered cycle, starting with Cycle 2, day 15, by positron emission tomography (PET) scan. According to RECIST guidelines, a complete tumor response is achieved when all target lesions have disappeared. Partial response is achieved when the sum of the diameters of all tumor lesions is reduced at least 30% compared to the sum of the tumor lesion diameters at pre-dose. The sum of the lesion diameters, if any, was calculated, per RECIST guidelines (Eisenhauer, E. A. et al., Eur. J. Cancer 45: 228-247, 2009).

After 28 days of treatment with ISIS 481464, the patient reported reduced fatigue and night sweats, and was tolerating the treatment well.

After 49 days of treatment with ISIS 481464, a PET scan was performed and revealed a 55% reduction in tumor size. Tumors were reduced in all compartments, but most notably, in the supraclavicular, paratracheal, pericardial, and mesenteric regions.

After 91 days of treatment with ISIS 481464, Patient #1001 had a second PET scan and the partial response observed in the first scan was found to be maintained at a 55% reduction in tumor size.

After 133 days of treatment with ISIS 481464, Patient #1001 had a third PET scan and the partial response was found to be maintained at a 55% reduction in tumor size.

After 162 days of treatment with ISIS 481464, further treatment was paused for a month during which Patient #1001 had a fourth PET scan, and the partial response was maintained at a 55% reduction in tumor size. Patient #1001 is scheduled for further scans.

Example 2

Phase 1, Open-Label, Study for Treating a Patient Having Advanced/Metastatic Hepatocellular Carcinoma with a STAT3 Antisense Oligonucleotide The effect of intravenous infusion of the STAT3 antisense oligonucleotide, ISIS 481464, in patients with advanced/metastatic hepatocellular carcinoma is being studied in an on-going clinical trial.

In the study described in this protocol, AZD9150 will be administered to patients with advanced/metastatic hepatocellular carcinoma at a starting dose of 1 mg/kg intravenously 3× during week 1 followed by 1× weekly and dose intensity will be escalated or de-escalated in subsequent cohorts through modification of unit dose administered and/or interval of administration to determine a maximum tolerated dose and recommended phase II dose in patients with advanced/metastatic hepatocellular carcinoma (HCC).

Following the dose escalation phase of the study additional patients will be enrolled to a dose expansion phase to explore further the safety, tolerability, pharmacokinetics and biological activity at selected dose(s)/schedules. Patients included in the study are relapsed, refractory, intolerant or unlikely to benefit from first-line systemic therapy (sorafenib).

To date, the 1 mg/kg and 1.5 mg/kg cohorts have completed. From the 1 mg/kg cohort 4 patients remain on study with stable disease in excess of 3 months. Stable disease has also been seen in 1.5 mg/kg cohort. These patients and future patients will be monitored further for clinical activity as the trial progresses.

The invention claimed is:

1. A method of treating cancer in a subject comprising administering to the subject a weekly dose of an antisense compound complementary to a nucleic acid encoding human STAT3, wherein the antisense compound comprises a modified oligonucleotide consisting of 12 to 30 linked nucleosides having a nucleobase sequence comprising the sequence of SEQ ID NO: 12; and wherein the dose comprises about 1.5 to 3.5 milligrams of the antisense compound per kilogram of the subject's body weight per week (1.5 to 3.5 mg/kg/wk).

2. The method of claim 1, wherein the dose is 3.0 milligrams of the antisense compound per kilogram of the subject's body weight per week (3.0 mg/kg/wk).

3. The method of claim 1, wherein the dose is administered for at least 1 to 52 weeks.

4. The method of claim 1, wherein the dose is administered to the subject 1 to 6 times per week.

5. The method of claim 1, wherein the cancer is B-cell lymphoma or hepatocellular carcinoma (HCC).

6. The method of claim 5, wherein the B-cell lymphoma is a non-Hodgkin's B-cell lymphoma.

7. The method of claim 6, wherein the non-Hodgkin's B-cell lymphoma is diffuse large B cell lymphoma (DLBCL).

8. The method of claim 1, wherein the modified oligonucleotide is single-stranded consisting of 16 linked nucleosides having a nucleobase sequence consisting of SEQ ID NO: 12, comprising:
   a gap segment consisting of ten linked deoxynucleosides;
   a 5' wing segment consisting of 3 linked nucleosides; and
   a 3' wing segment consisting of 3 linked nucleosides;
   wherein the gap segment is positioned between the 5' wing segment and the 3' wing segment; wherein each nucleoside of each wing segment comprises a constrained ethyl nucleoside; wherein each internucleoside linkage of the modified oligonucleotide is a phosphorothioate linkage; and wherein each cytosine of the modified oligonucleotide is a 5-methylcytosine.

* * * * *